(12) United States Patent
Wu et al.

(10) Patent No.: US 7,078,403 B1
(45) Date of Patent: Jul. 18, 2006

(54) ANTIVIRAL AGENTS

(75) Inventors: Wen-Yang Wu, Mount Waverley (AU); Keith Watson, Surrey Hills (AU); Darryl McConnell, Mount Waverley (AU); Betty Jin, Mount Waverley (AU); Guy Krippner, Glen Waverley (AU)

(73) Assignee: Biota Scientific Management Pty Ltd., Melbourne (AU)

( * ) Notice: Subject to any disclaimer, the term of this patent is extended or adjusted under 35 U.S.C. 154(b) by 565 days.

(21) Appl. No.: 10/018,963

(22) PCT Filed: Jun. 16, 2000

(86) PCT No.: PCT/AU00/00680

§ 371 (c)(1),
(2), (4) Date: May 21, 2002

(87) PCT Pub. No.: WO00/78746

PCT Pub. Date: Dec. 28, 2000

(30) Foreign Application Priority Data

Jun. 18, 1999 (AU) .......................................... PQ 1054

(51) Int. Cl.
*A61K 31/53* (2006.01)

(52) U.S. Cl. ...................... 514/241; 514/247; 514/362; 514/363; 514/364; 514/365; 514/373; 514/374; 514/379; 514/277; 514/255; 514/256; 514/242; 514/430; 514/449; 544/224; 544/336; 544/242; 544/180; 544/182; 546/1; 546/348; 548/136; 548/143; 548/128; 548/131; 548/146; 548/215; 548/206; 548/240; 549/29; 549/506

(58) Field of Classification Search ................. 514/247, 514/362–365, 373–374, 379, 277, 255, 256, 514/241, 242, 430, 449; 544/224, 336, 242, 544/180, 182; 546/1, 348; 548/136, 143, 548/128, 131, 146, 215, 206, 240; 549/29, 549/506, 146, 215
See application file for complete search history.

(56) References Cited

U.S. PATENT DOCUMENTS

| 3,997,565 | A | 12/1976 | Kauer ...................... 260/340.3 |
|---|---|---|---|
| 4,268,678 | A | 5/1981 | Diana et al. ................. 548/247 |
| 4,451,476 | A | 5/1984 | Diana ......................... 424/272 |
| 4,472,416 | A | 9/1984 | Stetter et al. ............... 424/269 |
| 4,843,087 | A | 6/1989 | Diana ......................... 514/374 |
| 4,857,539 | A | 8/1989 | Diana et al. ................. 514/378 |
| 4,861,791 | A | 8/1989 | Diana et al. ................. 514/374 |
| 4,939,267 | A | 7/1990 | Diana ......................... 548/237 |
| 4,942,241 | A | 7/1990 | Diana et al. ................. 548/131 |
| 4,945,164 | A | 7/1990 | Diana ......................... 548/247 |
| 4,956,351 | A | 9/1990 | Mesens et al. ................ 514/58 |
| 4,992,433 | A | 2/1991 | Stokbroekx et al. ........ 514/212 |
| 5,001,125 | A | 3/1991 | Stokbroekx et al. ........ 514/252 |
| 5,002,960 | A | 3/1991 | Diana ......................... 514/378 |
| 5,051,437 | A | 9/1991 | Diana ......................... 514/365 |
| 5,070,090 | A | 12/1991 | Stokbroekx et al. ...... 514/236.5 |
| 5,100,893 | A | 3/1992 | Stokbroekx et al. ........ 514/252 |
| 5,106,973 | A | 4/1992 | Stokbroekx et al. ........ 544/238 |
| 5,110,821 | A | 5/1992 | Diana ......................... 514/364 |
| 5,112,825 | A | 5/1992 | Stokbroekx et al. ........ 514/253 |
| 5,175,178 | A | 12/1992 | Diana et al. ................. 514/364 |
| 5,196,535 | A | 3/1993 | Stokbroekx et al. ........ 546/209 |
| 5,231,184 | A | 7/1993 | Stokbroekx et al. ........ 546/209 |
| 5,242,924 | A | 9/1993 | Diana ......................... 514/252 |
| 5,349,068 | A | 9/1994 | Diana et al. ................. 548/131 |
| 5,364,865 | A | 11/1994 | Diana ......................... 514/318 |
| 5,453,433 | A | 9/1995 | Aldous et al. .............. 514/362 |
| 5,464,848 | A | 11/1995 | Diana et al. ................. 514/364 |
| 5,514,679 | A | 5/1996 | Aldous et al. .............. 514/247 |
| 5,514,692 | A | 5/1996 | Aldous et al. .............. 514/314 |

(Continued)

FOREIGN PATENT DOCUMENTS

| EP | 0 248 253 A2 | 12/1987 |
|---|---|---|
| EP | 0290906 | 11/1988 |
| EP | 0 398 425 B1 | 3/1994 |
| EP | 1070711 A2 | 1/2001 |
| JP | 5-320117 | 12/1993 |
| JP | 8-81314 | 3/1996 |
| WO | WO 90/01874 | 3/1990 |
| WO | WO 98/17631 | 4/1998 |
| WO | WO 01/19822 A1 | 3/2001 |

OTHER PUBLICATIONS

Andries, K., "Discovery of pirodavir, a broad–spectrum inhibitor of rhinoviruses," in *The search for antiviral drugs*. Adams, J. and Merluzzi, V.J., (eds) Berkhauser, Boston USA, 1993, pp. 179–209.

(Continued)

*Primary Examiner*—S. Anna Jiang
*Assistant Examiner*—L. E. Crane
(74) *Attorney, Agent, or Firm*—Seed IP Law Group PLLC

(57) ABSTRACT

Disclosed herein are compounds of formula II:

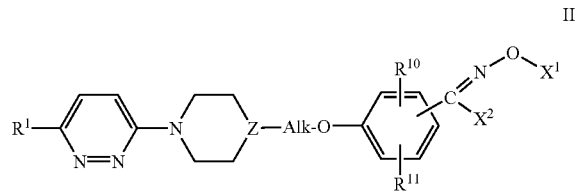

wherein Alk, Z, $X^1$, $X^2$, $R^1$, —$R^{10}$ and $R^{11}$ are defined herein, and their salts and pharmaceutically acceptable derivatives thereof, as well as other compounds of the general formula Het-A-Alk-W-Ar-C($X^2$)=NO-$X^2$ where Het, A, W and Ar are also defined herein. These compounds are useful in treating picornavirus infections in mammals. Novel intermediates of these compounds, as well as pharmaceutical compositions and methods of use, are also disclosed herein.

34 Claims, No Drawings

U.S. PATENT DOCUMENTS

| | | | |
|---|---|---|---|
| 5,523,312 | A | 6/1996 | Aldous et al. ............... 514/364 |
| 5,552,420 | A | 9/1996 | Aldous et al. ............... 514/364 |
| 5,567,717 | A | 10/1996 | Aldous et al. ............... 514/336 |
| 5,567,719 | A | 10/1996 | Aldous et al. ............... 514/342 |
| 5,618,821 | A | 4/1997 | Aldous et al. ............... 514/277 |
| 5,643,929 | A | 7/1997 | Diana et al. ................ 514/364 |
| 5,650,419 | A | 7/1997 | Aldous et al. ............... 514/363 |
| 5,665,763 | A | 9/1997 | Aldous et al. ............... 514/461 |
| 5,721,261 | A | 2/1998 | Aldous et al. ............... 514/364 |
| 5,750,527 | A | 5/1998 | Aldous et al. ............... 514/252 |
| 5,763,461 | A | 6/1998 | Aldous et al. ............... 514/340 |
| 5,821,257 | A | 10/1998 | Aldous et al. ............... 514/363 |
| 5,846,986 | A | 12/1998 | Aldous et al. ............... 514/364 |
| 6,048,880 | A | 4/2000 | Kawai et al. ................ 514/336 |
| 6,696,470 | B1 | 2/2004 | Kawai et al. ................ 514/333 |
| 2004/0054173 | A1 | 3/2004 | Kimura et al. ................ 544/60 |

OTHER PUBLICATIONS

Arruda, E and Hayden, FG., "Clinical studies of antiviral agents for picornaviral infections," in *Antiviral Chemotherapy*, Jeffries, DJ. and DeClercq, E. (ed). John Wiley & Sons Ltd., Sussex, England, 1995, pp. 321–355.

Rogers, JM et al., "Pleconaril. A broad spectrum antipicornavirus agent," in *Antiviral Chemotherapy 5*, Mills et al. (ed), Kluwer Academic/Plenum Publishers, NY, USA, 1999, pp. 69–76.

Rotbart, HA et al., "Treatment of human enterovirus infections," *Antiviral Research* 38: 1–14, 1998.

Schiff, GM and Sherwood, JR, "Clinical activity of Pleconaril in an experimentally induced Coxsackievirus A21 respiratory infection," *The Journal of Infectious Diseases*, 181:20–26, Jan. 2000.

Adams and Merluzzi (eds.), *The Search for Antiviral Drugs: Case Histories from Concept to Clinic*, Birkhouse, Boston, 1993, Chapter 8, pp. 179–209.

Diana et al., "Antipicornavirus drugs: current status," *Antiviral Chemistry and Chemotherapy* 8(5):401–408, 1997.

Hayden et al., "Intranasal pirodavir (R77,975) treatment of rhinovirus colds," *Antimicrobial Agents and Chemotherapy* 39(2):290–294, Feb. 1995.

Hayden et al., "Safety and efficacy of intranasal pirodavir (R77975) in experimental rhinovirus infection," *Antimicrobial Agents and Chemotherapy* 36(4):727–732, Apr. 1992.

Patani et al., "Bioisosterism: A Rational Approach in Drug Design," *Chemical Reviews* 96(8):3147–3176, Dec. 1996.

Sushil K. Starling, et al., "Anti–inflammatory & Anti–arrhythmic Activities of I–(Alkanoylphenoxy/Thiophenoxy)–3–($N^4$–phenylpiperazinyl)propanes," *Indian Journal of Chemistry 15B*:715–719, Aug. 1977.

Joseph T. Strupczewski et al., "3–[[Aryloxy)alkyl]piperidinyl]–1,2–benzisoxazoles as $D_2$/5–$HT_2$ Antagonists with Potential Atypical Antipsychotic Activity: Antipsychotic Profile of Iloperidone (HP 873)[1]," *J. Med Chem. 38*:1119–1131, 1995. (Mar. 1, 1995).

Michael S. Malamas et al., "Azole Phenoxy Hydroxyureas as Selective and Orally Active Inhibitors of 5–Lipoxygenase," *J. Med. Chem. 39*:237–425, 1995.(Dec. 15, 1995).

ANTIVIRAL AGENTS

This application is a national stage application filed under 35 U.S.C. 371 of International Application No. PCT/AU00/00680, accorded an International Filing Date of Jun. 16, 2000; which claims priority to Australian PQ1054, filed Jun. 18, 1999.

This invention relates to antiviral agents, in particular to compounds useful in the treatment of infections caused by Picornaviridae, such as human rhinovirus (HRV) and methods for their preparation. The invention also relates to the use of these compounds in the treatment of picornavirus infections and to intermediates useful in the preparation of these compounds. The compounds of the invention are especially suitable for use in the treatment of HRV and accordingly it will be convenient to describe the invention in connection with these viruses. However it is to be understood that the invention is also applicable to other viruses of the Picornavirus family.

Human rhinovirus are a member of the genus Rhinovirus of the picornavirus family and are believed to be responsible for between 40 and 50% of common cold infections. Human rhinoviruses comprise a group of over 100 serotypically distinct viruses and accordingly antiviral activity for multiple serotypes and potency are considered to be equally important factors in drug design.

Two cellular receptors have been identified to which almost all typed HRVs bind. The major group, which comprises 91 of the more than 100 typed serotypes, binds to the intracellular adhesion molecule-1 (ICAM-1) while the minor group, which comprises the rest of typed serotypes with the exception of HRV87, binds to the low density lipoprotein receptor family of proteins.

Another genus of the Picornaviridae family is represented by the Enteroviruses. This genus includes polioviruses 1–3, coxsackieviruses A (23 serotypes) and B (6 serotypes), echoviruses (31 serotypes) and numbered enteroviruses 68–71. The clinical syndromes caused by enteroviruses include poliomyelitis, meningitis, encephalitis, pleurodynia, herpangina, hand foot and mouth disease, conjunctivitis, myocarditis and neonatal diseases such as respiratory illnesses and febrile illnesses.

Viruses of the Picornavirus family are characterised by a single stranded (+) RNA genome encapsidated by a protein shell (or capsid) having pseudo icosahedral symmetry. The surface of the capsid contains "canyons" which surround each of the icosahedral fivefold axes and it is believed that the cellular receptors bind to residues on the canyon floor.

A hydrophobic pocket lies underneath the canyon within which a number of antiviral compounds are capable of binding, sometimes with consequential conformational changes. Some of these compounds have been shown to inhibit the uncoating of HRVs and, for some of the major receptor group viruses, inhibition of cell receptor binding has also been demonstrated. It has also been shown that when a compound is bound within the hydrophobic capsid pocket, HRVs are more stable to denaturation by heat or acids.

Examples of antipicornaviral compounds believed to act by binding within the hydrophobic pockets of the picornavirus capsid are described in U.S. Pat. Nos. 4,992,433, 5,100, 893, 5,070,090 and Australian Patent No. 628172. One compound which has been the subject of recent human clinical trials is ethyl 4-[2-[1-(6-methyl-3-pyridazinyl)-4-piperidinyl]-ethoxy]benzoate, otherwise known as "Pirodavir". ("Intranasal Pirodavir (R77,975) Treatment of Rhinovirus Colds" F. G. Hayden, et al., *Antimicrobial Agents and Chemotherapy*, 39, 290–294, 1995).

A novel class of antiviral compounds has now been discovered which has been found to exhibit particularly favourable antipicornaviral properties.

Accordingly the present invention provides a compound of formula I

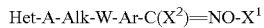

$$\text{Het-A-Alk-W-Ar-C}(X^2)=\text{NO-X}^1 \qquad \text{I}$$

its salts, and pharmaceutically acceptable derivatives thereof where

Het is an optionally substituted 5- or 6-membered monocyclic heterocyclic radical or an optionally substituted 9- or 10-membered bicyclic heterocyclic radical; A is O, S, NH, $N(C_{1-6}\text{alkyl})$, $CH_2O$, a direct bond or a bivalent heterocyclic radical of the formula

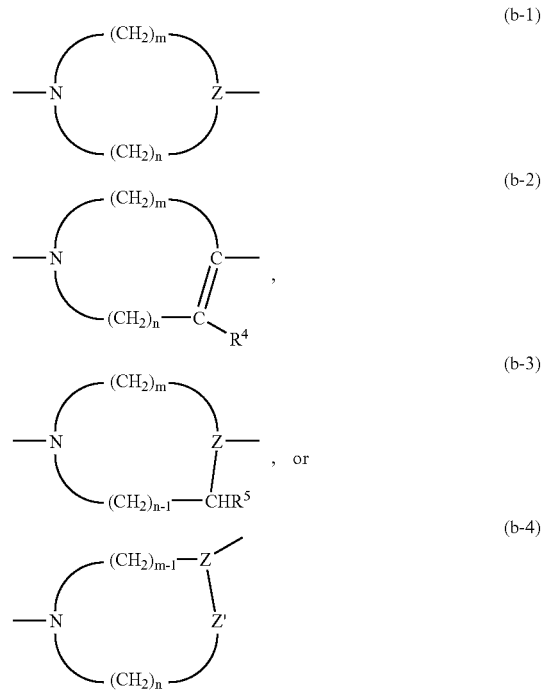

where one or more of the carbon atoms within the radicals (b-1) to (b-4) may be optionally substituted with $C_{1-6}$alkyl or two carbon atoms in the radicals (b-1) to (b-4) may be bridged with a $C_{2-4}$alkylene radical, m and n are each independently integers of 1 to 4 inclusive with the proviso that the sum of m and n in radicals (b-1) to (b-4) is 3, 4 or 5;

Z is N or $CR^6$ where $R^6$ is hydrogen, hydroxy, $C_{1-6}$alkyl, $C_{1-6}$alkoxy or amino;

Z' is O, S, $CHR^7$ or $NR^8$ where $R^7$ is hydrogen, hydroxy, $C_{1-6}$alkyl, $C_{1-6}$alkoxy or amino and $R^8$ is hydrogen or $C_{1-6}$alkyl;

$R^4$ is hydrogen or $C_{1-6}$alkyl; and $R^5$ is hydrogen, hydroxy, $C_{1-6}$alkyl or $C_{1-6}$alkoxy;

Alk is $C_{1-7}$alkylene or a direct bond;

W is O, S, $OCH_2$, a direct bond or $NR^9$ where $R^9$ is hydrogen or $C_{1-6}$alkyl;

Ar is an optionally substituted 5- or 6-membered monocyclic aryl radical or an optionally substituted 9- or 10-membered bicyclic aryl radical;

$X^1$ is $C_{1-6}$alkyl, $C_{3-6}$alkenyl, $C_{3-6}$haloalkenyl, $C_{3-6}$alkynyl, $C_{3-6}$haloalkynyl or $C_{1-6}$alkyl substituted by halo, cyano, nitro, hydroxy, aryl, $C_{1-4}$alkoxy, $C_{2-6}$alkoxyalkoxy, acyl or $C_{1-4}$alkylthio; and $X^2$ is hydrogen, cyano, F, Cl, $C_{1-4}$alkyl, $C_{1-4}$haloalkyl or a bivalent radical of formula —$CH_2)_2$—, —$(CH_2)_3$—, —$CH_2O$— or —$CH_2)_2O$— which forms a 5- or 6membered ring with a neighbouring carbon atom of Ar.

The oxime ether compounds of the present invention may be in cis or trans form, or a mixture of these forms.

As used herein the term "aryl" refers to aromatic rings or ring systems. The aromatic rings may be carbocyclic, heterocyclic or pseudo aromatic, and may be mono- or bi-cyclic ring systems. The aromatic rings or ring systems are generally composed of 5 to 10 carbon atoms and, in the case of heteroaromatic rings, may contain one or more heteroatoms selected from N, S and O. Examples of suitable aryl groups include but are not limited to phenyl, biphenyl, naphthyl, tetrahydronaphthyl, pyridinyl, thiophenyl, benzothiophenyl, furyl, isobenzofuranyl, pyrrolyl, imidazolyl, pyrazolyl, pyrazinyl, pyrimidinyl, pyridazinyl, indolyl, indolizinyl, isoindolyl, purinyl, oxazolyl, thiazolyl, isothiazolyl, isooxazolyl, triazinyl, triazolyl, tetrazolyl and the like, each of which may be optionally substituted with $C_{1-6}$alkyl, $C_{1-6}$alkoxy, $C_{3-6}$alkynyl, $C_{3-6}$-alkynyl, halo, hydroxy, mercapto, trifluoromethyl, amino, cyano or mono or di($C_{1-6}$alkyl) amino. The term "pseudoaromatic" refers to a ring system which is not strictly aromatic, but which is stabilized by means of delocalization of electrons and behaves in a similar manner to aromatic rings. Examples of pseudoaromatic rings include but are not limited to furan, thiophene, pyrrole and the like.

Preferred aryl groups include phenyl, pyridinyl, pyridazinyl, pyrazinyl, pyrimidinyl, 1,2,4-triazinyl, furyl, thiophenyl thiazolyl, isothiazolyl, isoxazolyl, 1,2,4-triazolyl, oxazolyl, imidazolyl, pyrazolyl, 1,4-benzothiazinyl, indolyl and benzofuranyl. Particular examples of bivalent monocyclic and bicyclic aryl radicals are radicals of formula (c-1) to (c-6) below:

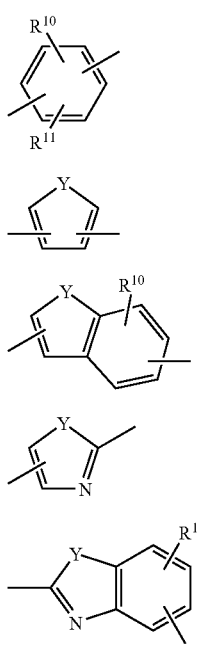

(c-1)

(c-2)

(c-3)

(c-4)

(c-5)

(c-6)

where Y is as defined above; and $R^{10}$ and $R^{11}$ are each independently hydrogen, $C_{1-6}$alkyl, hydroxy $C_{1-6}$alkyl, halo, amino, cyano, nitro, $C_{1-6}$alkoxy, hydroxy, $C_{1-6}$alkylthio, or trifluoromethyl.

Examples of Ar groups in combination with 5- or 6-membered rings formed by $X^2$ with the neighbouring carbon atom of Ar include indanones, tetralones, benzofuranones and benzopyranones.

The term "heterocyclic radical" as used herein refers to mono or bicyclic rings or ring systems which include one or more heteroatoms selected from N, S and O. The rings or ring systems generally include 1 to 14 carbon atoms in addition to the heteroatom(s) and may be saturated, unsaturated, aromatic or pseudoaromatic.

Examples of 5-membered monocyclic heterocycles include furyl, thienyl, pyrrolyl, oxazolyl, thiazolyl, isoxazolyl, isothiazolyl, pyrazolyl imidazolyl, triazolyl, tetrazolyl, oxadiazolyl, thiadiazolyl and examples of 6-membered monocyclic heterocycles include pyridyl, pyrimidinyl, pyridazinyl, pyrazinyl and triazinyl. Examples of 9 and 10-membered bicyclic heterocycles include indolyl, benzofuranyl, benzothienyl, benzoxazolyl, benzothiazolyl, benzisoxazolyl, benzisothiazolyl, indazolyl, isoquinolinyl, quinolinyl, quinoxalinyl, cinnolinyl, phthalazinyl, quinazolinyl, benzotriazinyl and the like. Examples of preferred heterocyclic ring systems include (optionally substituted) isoxazoles, isothiazoles, 1,3,4-oxadiazoles, 1,3,4-thiadiazoles, 1,2,4-oxadiazoles, 1,2,4-thiadiazoles, oxazoles, thiazoles, pyridines, pyridazines, pyrimidines, pyrazines, 1,3,5-triazines, benzoxazoles, benzothiazoles, benzisoxazoles, benzisothiazoles, quinolines and quinoxalines. Particular examples of the group Het are radicals of formula (a-1) to (a-14) below:

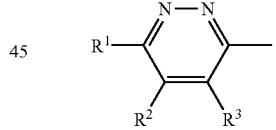

(a-1)

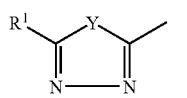

(a-2)

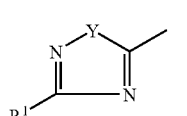

(a-3)

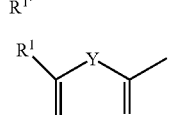

(a-4)

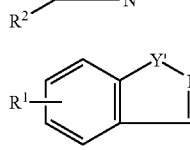

(a-5)

-continued

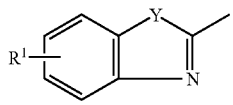
(a-6)

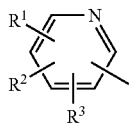
(a-7)

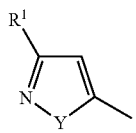
(a-8)

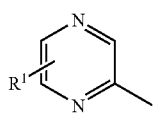
(a-9)

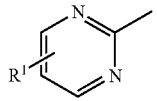
(a-10)

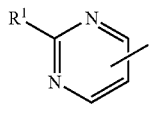
(a-11)

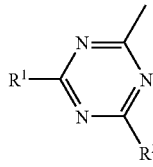
(a-12)

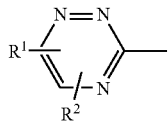
(a-13)

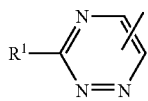
(a-14)

wherein $R^1$ is hydrogen, $C_{1-6}$ alkyl, halo, hydroxy, mercapto, halo$C_{1-6}$alkyl, amino, mono or di($C_{1-6}$alkyl)amino, cyano, formyl, $C_{1-6}$alkoxy, hydroxy$C_{1-4}$ alkyl, $C_{1-4}$alkoxy$C_{1-4}$ alkyl, $C_{1-6}$haloalkoxy, aryloxy, $C_{1-6}$alkylthio, arylthio, $C_{1-6}$alkylsulphinyl, $C_{1-6}$alkylsulphonyl, arylsulphinyl, arylsulphonyl, —CH=NO-$C_{1-4}$alkyl, $C_{1-6}$-alkyloxycarbonyl, $C_{1-6}$alkylcarbonyl or aryl;

$R^2$ and $R^3$ are each independently selected from hydrogen, $C_{1-6}$alkyl, $C_{1-6}$alkoxy, halo or, in radicals (a-1), (a-4), (a-7) and (a-13), $R^1$ and $R^2$, or $R^2$ and $R^3$ combined may represent a bivalent radical of formula —CH=CH—CH=CH— or $(CH_2)_p$ where p is an integer from 2 to 4;

Y is O or S; and

Y' is O, S, SO or $SO_2$.

In some preferred embodiments of the invention one or more of the following definitions apply:

Het is a radical of formula (a-1), (a-2) or (a-8);

$R^1$ is hydrogen, methyl, ethyl, chloro, methoxy or trifluoromethyl;

$R^2$ and $R^3$ are each independently hydrogen, chloro or methyl;

Y is O or S;

A is O, NH, NMe, a bond, or a radical of formula (b-1);

Z is CH or N;

Alk is $C_{1-6}$alkylene or a direct bond;

W is O;

Ar is a radical of formula (c-1), (c-2) or (c4);

$R^{10}$ and $R^{11}$ are each independently H, methyl, chloro, hydroxy, methoxy, cyano or nitro;

$X^1$ is $C_{1-4}$-alkyl, $C_{2-4}$alkoxyalkyl, $C_{3-4}$alkenyl, $C_{3-4}$alknyl, $C_{1-4}$haloalkyl, $C_{3-4}$haloalkenyl, $C_{3-4}$haloalkynyl or cyanomethyl;

$X^2$ is H, methyl or a bivalent radical of formula $(CH_2)_2$ or $(CH_2)_3$ which forms a 5- or 6-membered ring with the Ar group.

As used herein the term "$C_{1-6}$alkyl" as used alone or as part of a group such as "di($C_{1-6}$alkyl)amino" refers to straight chain, branched or cyclic alkyl groups having from 1 to 6 carbon atoms. Examples of such alkyl groups include methyl, ethyl, n-propyl, isopropyl, n-butyl, cyclopentyl and cyclohexyl. Similarly $C_{1-4}$ alkyl refers to such groups having from 1 to 4 carbon atoms.

As used herein the term "halo" as used alone or as part of a group such as "$C_{3-6}$halo alkenyl" refers to fluoro, chloro, bromo and iodo groups.

As used herein the terms "$C_{1-6}$alkoxy" and "$C_{1-6}$alkyloxy" refer to straight chain or branched alkoxy groups having from 1 to 6 carbon atoms. Examples of $C_{1-6}$alkoxy include methoxy, ethoxy, n-propoxy, isopropoxy, and the different butoxy isomers.

As used herein the term "$C_{3-6}$alkenyl" refers to groups formed from $C_{3-6}$ straight chain, branched or cyclic alkenes. Examples of $C_{3-6}$alkenyl include allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1,3-butadienyl, 1–4,pentadienyl, 1,3-cyclopentadienyl, 1,3-hexadienyl, 1,4-hexadienyl, 1,3-cyclohexadienyl and 1,4-cyclohexadienyl.

As used herein the term "$C_{3-6}$-alkynyl" refers to groups formed from $C_{3-6}$ straight chain or branched groups as previously defined which contain a triple bond. Examples of $C_{3-6}$alkynyl include 2,3-propynyl and 2,3- or 3,4-butynyl.

The term "optionally substituted" as used herein means that a group may include one or more substituents which do not interfere with the binding activity of the compound of formula I. In some instances the substituent may be selected to improve binding. Examples of optional substituents include halo, $C_{1-4}$alkyl, $C_{2-4}$alkenyl, $C_{2-4}$alkynyl, $C_{1-4}$alkoxy, halo$C_{1-4}$alkyl, hydroxy$C_{1-4}$alkyl, $C_{1-4}$alkoxy, $C_{1-4}$-alkyl, hydroxy, aryl, amino, cyano, mercapto, $C_{1-4}$alkylamino, $C_{1-4}$dialkylamino, aryloxy, formyl, $C_{1-4}$alkylcarbonyl and $C_{1-4}$alkoxycarbonyl.

A particular group of compounds of the invention has the formula II:

II

[Structure of Formula II: pyridazine with R¹ substituent connected to piperidine/piperazine (N, Z), linked via Alk-O to phenyl ring bearing R¹⁰, R¹¹, and C(=N-O-X¹)(X²)]

wherein:

R¹ is hydrogen, $C_{1-4}$alkyl, halo, hydroxy, mercapto, trifluoromethyl, amino, mono or di($C_{1-4}$alkyl)amino, cyano, formyl, —CH=NO—$C_{1-4}$ alkyl, $C_{1-4}$alkoxy, $C_{1-4}$haloalkoxy, aryloxy, $C_{1-4}$alkylthio, or aryl;

Z is CH or N;

Alk is $C_{1-6}$alkylene;

$R^{10}$ and $R^{11}$ are each independently hydrogen, $C_{1-4}$alkyl, $C_{1-4}$alkoxy, halo, hydroxy;

$X^1$ is $C_{1-6}$alkyl, $C_{3-6}$alkenyl, $C_{3-6}$haloalkenyl, $C_{3-6}$alkynyl, $C_{3-6}$haloalkynyl or $C_{1-6}$alkyl optionally substituted by halo, cyano, nitro, hydroxy, aryl, $C_{1-4}$alkoxy or $C_{1-4}$alkylthio; and $X^2$ is hydrogen, cyano, $C_{1-4}$alkyl, $C_{1-4}$haloalkyl or $X^2$ is —CH$_2$CH$_2$— or —CH$_2$CH$_2$CH$_2$— forming a 5- or 6-membered ring with a carbon atom on the phenyl ring.

Another particular set of compounds of the invention have the formula III:

III

[Structure of Formula III: isoxazole ring with R¹ substituent linked via A-Alk-O to phenyl ring bearing R¹⁰, R¹¹, and C(=N-O-X¹)(X²)]

wherein:

R¹ is hydrogen, $C_{1-4}$alkyl, halo, hydroxy, mercapto, trifluoromethyl, amino, mono or di($C_{1-4}$alkyl)amino, cyano, formyl, —CH=NO—$C_{1-4}$alkyl, $C_{1-4}$alkoxy, $C_{1-4}$haloalkoxy, aryloxy, $C_{1-4}$alkylthio, or aryl;

A is a bond or CH$_2$O;

Alk is $C_{1-7}$alkylene;

$R^{10}$ and $R^{11}$ are each independently hydrogen, $C_{3-6}$alkyl, $C_{1-4}$alkoxy, halo, hydroxy;

$X^1$ is $C_{1-6}$alkyl, $C_{3-6}$alkenyl, $C_{3-6}$haloalkenyl, $C_{3-6}$alkynyl, $C_{3-6}$haloalkynyl or $C_{1-6}$alkyl optionally substituted by halo, cyano, nitro, hydroxy, aryl, $C_{1-4}$alkoxy or $C_{1-4}$alkylthio; and $X^2$ is hydrogen, cyano, $C_{1-4}$alkyl, $C_{1-4}$haloalkyl or $X^2$ is —CH$_2$CH$_2$— or —CH$_2$CH$_2$CH$_2$— forming a 5- or 6-membered ring with a carbon atom on the phenyl ring.

A particular group of compounds of the invention has the formula IV

IV

[Structure of Formula IV: pyridazine with R¹ linked to piperidine (N, Z), connected via Alk-O to phenyl ring bearing R¹⁰, R¹¹, and C(=N-O-X¹)(X²)]

wherein:

R¹ is hydrogen, $C_{1-4}$ alkyl, halo, hydroxy, mercapto, trifluoromethyl, amino, mono or di($C_{1-4}$alkyl)amino, cyano, formyl, —CH=NO-$C_{1-4}$alkyl, $C_{1-4}$alkoxy, $C_{1-4}$haloalkoxy, aryloxy, $C_{1-4}$alkylthio, or aryl;

Z is CH or N;

Alk is $C_{1-6}$alkylene;

$R^{10}$ and $R^{11}$ are each independently hydrogen, $C_{1-4}$alkyl, $C_{1-4}$alkoxy, halo, hydroxy;

$X^1$ is $C_{1-6}$alkyl, $C_{3-6}$alkenyl, $C_{3-6}$haloalkenyl, $C_{3-6}$alkynyl, $C_{3-6}$haloalkynyl or $C_{1-6}$alkyl optionally substituted by halo, cyano, nitro, hydroxy, aryl, $C_{1-4}$alkoxy or $C_{1-4}$alkylthio; and $X^2$ is hydrogen, cyano, $C_{1-4}$alkyl, $C_{1-4}$haloalkyl or $X^2$ is —CH$_2$CH$_2$— or —CH$_2$CH$_2$CH$_2$— forming a 5- or 6-membered ring with a carbon atom on the phenyl ring.

A particular group of compounds of the invention has the formula V

V

[Structure of Formula V: Het-N piperidine/piperazine (Z) linked via Alk-O to phenyl ring bearing R¹⁰, R¹¹, and C(=N-O-X¹)(X²)]

wherein:

Het is pyridyl, pyrazinyl, thiadiazolyl, benzoxazolyl, 1,3,5-triazinyl, pyrimidinyl or quinoxalinyl, each of which may be optionally substituted with 1 to 3 substituents selected from halo, trifluoromethyl, $C_{1-4}$alkyl, $C_{1-4}$alkoxy or hydroxy;

Z is CH or N;

Alk is $C_{1-6}$-alkylene;

$R^{10}$ and $R^{11}$ are each independently hydrogen, $C_{1-4}$-alkyl, $C_{1-4}$alkoxy, halo, hydroxy;

$X^1$ is $C_{1-6}$alkyl, $C_{3-6}$alkenyl, $C_{3-6}$haloalkenyl, $C_{3-6}$alkynyl, $C_{3-6}$haloalkynyl or $C_{1-6}$alkyl optionally substituted by halo, cyano, nitro, hydroxy, aryl, $C_{1-4}$alkoxy or $C_{1-4}$alkylthio; and $X^2$ is hydrogen, cyano, $C_{1-4}$alkyl, $C_{1-4}$haloalkyl or $X^2$ is —CH$_2$CH$_2$— or —CH$_2$CH$_2$CH$_2$— forming a 5- or 6-membered ring with a carbon atom on the phenyl ring.

Another group of compounds of the invention has the formula VI

[Structure of Formula VI: Het-A—Alk-O— phenyl ring bearing R¹⁰, R¹¹, and C(=N-O-X¹)(X²)]

wherein:

Het is pyridyl, pyrazinyl, thiadiazolyl, benzoxazolyl, 1,3,5-triazinyl, pyrimidinyl or quinoxalinyl, each of which may be optionally substituted with 1 to 3 substituents selected from halo, trifluoromethyl, $C_{1-4}$alkyl, $C_{1-4}$alkoxy or hydroxy;

A is a direct bond, O, NH or NMe;

Alk is $C_{1-6}$ alkylene;

$R^{10}$ and $R^{11}$ are each independently hydrogen, $C_{1-4}$alkyl, $C_{1-4}$alkoxy, halo, hydroxy;

$X^1$ is $C_{1-6}$alkyl, $C_{3-6}$alkenyl, $C_{3-6}$haloalkenyl, $C_{3-6}$alkynyl, $C_{3-6}$haloalkynyl or $C_{1-6}$alkyl optionally substituted by halo, cyano, nitro, hydroxy, aryl, $C_{1-4}$alkoxy or $C_{1-4}$alkylthio; and $X^2$ is hydrogen, cyano, $C_{1-4}$alkyl, $C_{1-4}$haloalkyl or $X^2$ is —CH$_2$CH$_2$— or —CH$_2$CH$_2$CH$_2$— forming a 5- or 6-membered ring with a carbon atom on the phenyl ring.

Examples of specific compounds within the scope of the present invention are shown in Tables 1 to 8 below.

TABLE 1

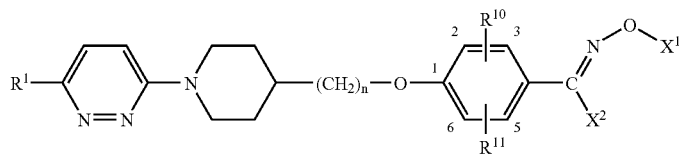

| Compd Number | $R^1$ | n | $R^{10}, R^{11}$ | $X^1$ | $X^2$ |
|---|---|---|---|---|---|
| 1 | Cl | 2 | H | CH$_2$CH$_3$ | H |
| 2 | Me | 2 | H | CH$_2$CH$_3$ | H |
| 3 | Cl | 2 | H | CH$_2$CH$_3$ | CH$_3$ |
| 4 | Me | 2 | H | CH$_2$CH$_3$ | CH$_3$ |
| 5 | Cl | 2 | 2-(OMe) | CH$_2$CH$_3$ | H |
| 6 | Cl | 2 | 2,6-(OMe)$_2$ | CH$_2$CH$_3$ | CH$_3$ |
| 7 | Me | 2 | H | CH$_3$ | H |
| 8 | Cl | 2 | H | CH$_3$ | H |
| 9 | Me | 2 | H | CH$_3$ | CH$_3$ |
| 10 | Cl | 2 | H | CH$_3$ | CH$_2$CH$_3$ |
| 11 | Cl | 2 | H | CH$_2$CH$_2$CH$_3$ | H |
| 12 | Cl | 2 | H | CH(CH$_3$)$_2$ | H |
| 13 | Cl | 2 | H | CH$_2$CH=CH$_2$ | H |
| 14 | Cl | 2 | H | CH$_2$CN | H |
| 15 | Cl | 2 | H | CH$_2$C$_6$H$_5$ | H |
| 18 | Cl | 2 | 2,6-(OMe)$_2$ | CH$_3$ | H |
| 19 | Cl | 2 | 2-(OMe) | CH$_3$ | CH$_3$ |
| 20 | Cl | 2 | H | (CH$_2$CH$_2$O)$_2$CH$_2$CH$_3$ | H |
| 21 | CF$_3$CH$_2$O | 2 | H | CH$_2$CH$_3$ | H |
| 26 | CH$_3$O | 2 | H | CH$_2$CH$_3$ | H |
| 29 | Cl | 1 | H | CH$_2$Phenyl | H |
| 30 | Cl | 1 | H | CH$_2$CH=CH$_2$ | H |
| 31 | Cl | 1 | H | CH$_2$CH$_3$ | H |
| 32 | Cl | 3 | H | CH$_2$CH$_3$ | H |
| 33 | Cl | 2 | 2-(OMe) | CH$_3$ | H |
| 34 | Cl | 2 | H | CH$_2$CH$_3$ | CH$_2$CH$_3$ |
| 35 | Cl | 2 | H | CH$_2$CH=CH$_2$ | CH$_2$CH$_3$ |
| 36 | Cl | 2 | 2-NO$_2$ | CH$_2$CH$_3$ | H |
| 37 | Cl | 2 | 3-OH | CH$_2$CH$_3$ | H |
| 42 | Cl | 2 | 2-Me | CH$_2$CH$_3$ | H |
| 43 | Cl | 2 | 2-Me | CH$_2$CH=CH$_2$ | H |
| 44 | Cl | 2 | 2-Me | CH$_3$ | H |
| 45 | Cl | 2 | 2,6-(Me)$_2$ | CH$_2$CH$_3$ | H |
| 49 | H | 2 | H | CH$_2$CH$_3$ | H |
| 50 | Cl | 2 | 3-OMe | CH$_2$CH$_3$ | H |
| 51 | Me | 2 | 2-Me | CH$_2$CH$_3$ | H |
| 52 | Me | 2 | 2-Me | CH$_3$ | H |
| 53 | Me | 2 | 2-Me | CH$_2$CH=CH$_2$ | H |
| 54 | Me | 2 | 2-Me | CH$_2$CH$_2$CH$_3$ | H |
| 55 | Cl | 0 | H | CH$_2$CH$_3$ | H |
| 56 | Phenyl | 2 | H | CH$_2$CH$_3$ | H |
| 57 | Cl | 2 | H | CH$_2$CH$_3$ (cis isomer) | H |
| 58 | CF$_3$ | 2 | H | CH$_2$CH$_3$ | H |
| 59 | Me | 2 | H | CH$_2$CF$_3$ | H |
| 63 | MeO | 2 | H | CH$_2$CH=CH$_2$ | H |
| 85 | Me | 2 | H | CH$_2$CH$_2$CH$_3$ | H |
| 86 | Me | 2 | R | CH$_2$CH$_2$OCH$_3$ | H |
| 87 | Me | 2 | H | CH$_2$CH=CH$_2$ | H |
| 88 | Me | 2 | H | CH$_2$C≡CH | H |
| 89 | Cl | 3 | H | CH$_3$ | H |
| 90 | Cl | 3 | H | CH$_2$CH=CH$_2$ | H |
| 94 | Me | 3 | H | CH$_3$ | H |
| 95 | Me | 3 | H | CH$_2$CH$_3$ | H |
| 96 | Me | 3 | H | CH$_2$CH=CH$_2$ | H |

TABLE 1-continued

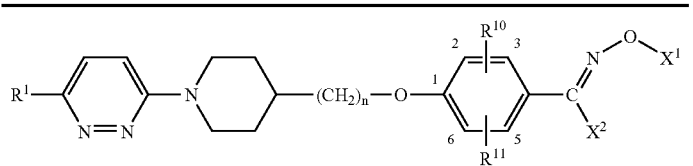

| Compd Number | R¹ | n | R¹⁰, R¹¹ | X¹ | X² |
|---|---|---|---|---|---|
| 100 | CF₃ | 3 | H | CH₃ | H |
| 102 | H | 3 | H | CH₃ | H |
| 103 | H | 3 | H | CH₂CH₃ | H |
| 104 | H | 3 | H | CH₂CH=CH₂ | H |
| 128 | O=CH | 2 | H | CH₂CH₃ | H |
| 129 | HOCH₂ | 2 | H | CH₂CH₃ | H |
| 143 | Me | 2 | H | CH₂CH₂F | H |
| 144 | Me (Pyridazine N-oxide) | 2 | H | CH₂CH₃ | H |
| 145 | Me | 2 | H | CH₂CH₃ | H |
| 146 | Me | 2 | 2-OH | CH₂CH₃ | H |
| 185 | Me | 2 | 3,5-(Me)₂ | CH₂CH₃ | H |
| 186 | Me | 2 | 3,5-(Me)₂ | CH₃ | H |
| 187 | Me | 2 | 3-OMe | CH₂CH₃ | H |
| 188 | Me | 2 | 3-Me | CH₂CH₃ | H |
| 189 | Me | 2 | 3-Me | CH₃ | H |
| 190 | Me | 2 | 2,5-(Me)₂ | CH₂CH₃ | H |
| 191 | Me | 2 | 2,5-(Me)₂ | CH₃ | H |
| 192 | ME | 2 | 2,3-(Me)₂ | CH₂CH₃ | H |
| 193 | Me | 2 | 2,3-(Me)₂ | CH₃ | H |
| 208 | MeON=CH— | 2 | H | CH₂CH₃ | H |

TABLE 2

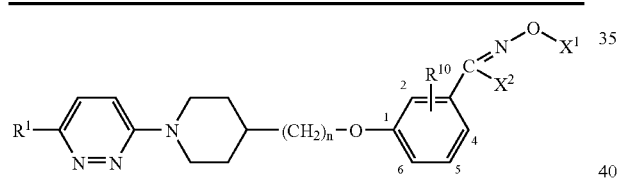

| Compound number | R¹ | n | R¹⁰ | X¹ | X² |
|---|---|---|---|---|---|
| 16 | Cl | 2 | H | CH₃ | H |
| 17 | Cl | 2 | 6-OMe | CH₃ | H |
| 38 | Cl | 2 | 5-OH | CH₃ | H |
| 39 | Cl | 2 | 5-OH | CH₂CH₃ | H |
| 40 | Cl | 2 | 5-OH | CH₂CH=CH₂ | H |
| 41 | Cl | 2 | H | CH₂CH₃ | H |
| 46 | Me | 2 | H | CH₂CH₃ | H |
| 47 | Me | 2 | H | CH₂CH=CH₂ | H |
| 48 | Me | 2 | H | CH₃ | H |
| 60 | Cl | 1 | H | CH₃ | H |
| 61 | Cl | 1 | H | CH₂CH₃ | H |
| 62 | Cl | 1 | H | CH₂CH=CH₂ | H |
| 91 | Cl | 3 | H | CH₃ | H |
| 92 | Cl | 3 | H | CH₂CH₃ | H |
| 93 | Cl | 3 | H | CH₂CH=CH₂ | H |
| 97 | Me | 3 | H | CH₃ | H |
| 98 | Me | 3 | H | CH₂CH₃ | H |
| 99 | Me | 3 | H | CH₂CH=CH₂ | H |
| 101 | CF₃ | 3 | H | CH₃ | H |
| 105 | H | 3 | H | CH₃ | H |
| 106 | H | 3 | H | CH₂CH₃ | H |
| 107 | H | 3 | H | CH₂CH=CH₂ | H |
| 213 | Me | 2 | H | CH₂CH₃ | —CH₂—CH₂— (2-position) |

TABLE 3

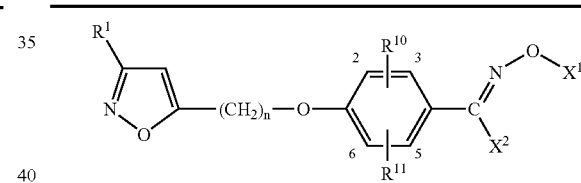

| Compd number | R¹ | n | R¹⁰, R¹¹ | X¹ | X² |
|---|---|---|---|---|---|
| 22 | Me | 3 | 2,6-(Me)₂ | CH₃ | H |
| 23 | Me | 3 | 2,6-(Me)₂ | CH₂CH=CH₂ | H |
| 24 | Me | 3 | 2,6-(Me)₂ | CH₂CH₃ | H |
| 25 | Me | 3 | 2,6-(Me)₂ | CH₂C₆H₅ | H |
| 108 | Me | 3 | H | CH₂CH₃ | H |
| 109 | Me | 3 | 2,6-(Me)₂ | CH₃ | Me |
| 110 | Me | 3 | 2,6-(Me)₂ | CH₂CH=CH₂ | Me |
| 111 | Me | 3 | 2,6-(Me)₂ | CH₂CH=CH₂ (cis-isomer) | Me |
| 112 | Me | 3 | 2,6-(Me)₂ | CH₂CH₂CH₃ | H |
| 113 | Me | 3 | 2,6-(Me)₂ | CH₃ | Et |
| 114 | Me | 3 | 2,6-(Me)₂ | CH₂CH₃ | Et |
| 115 | Me | 3 | 2,6-(Me)₂ | CH₂CH=CH₂ | Et |
| 116 | Me | 3 | 2,6-(Me)₂ | CH₂CH₃ | Me |
| 117 | Me | 3 | 2,6-(Me)₂ | CH(CH₃)₂ | H |
| 118 | Me | 3 | 2,6-(Me)₂ | CH₂CN | H |
| 119 | Me | 3 | 2,6-(Me)₂ | CH₂C≡CH | H |
| 120 | Me | 6 | 2,6-(Me)₂ | CH₂CH₃ | H |
| 121 | Me | 7 | 2,6-(Me)₂ | CH₂CH₃ | H |
| 122 | Me | 5 | 2,6-(Me)₂ | CH₂CH₃ | H |
| 123 | Me | 4 | 2,6-(Me)₂ | CH₂CH₃ | H |
| 124 | Me | 3 | 2,6-(Me)₂ | CH₂CF₃ | H |
| 125 | Me | 3 | 2,6-(Me)₂ | CH₂CH₂OCH₂CH₃ | H |
| 126 | Me | 3 | 2,6-(Me)₂ | CH₂COCH₃ | H |
| 127 | Phenyl | 3 | 2,6-(Me)₂ | CH₂CH₃ | H |
| 130 | Et | 3 | 2,6-(Me)₂ | CH₂CH₃ | H |
| 131 | n-Pr | 3 | 2,6-(Me)₂ | CH₂CH₃ | H |
| 132 | Et | 2 | 2,6-(Me)₂ | CH₂CH₃ | H |

TABLE 3-continued

Structure: R¹-isoxazole-(CH₂)n-O-phenyl(R¹⁰,R¹¹)-C(X²)=N-O-X¹

| Compd number | R¹ | n | R¹⁰, R¹¹ | X¹ | X² |
|---|---|---|---|---|---|
| 133 | n-Pr | 2 | 2,6-(Me)₂ | CH₂CH₃ | H |
| 134 | Me | 3 | 2,6-(Me)₂ | CH₂CH₂F | H |
| 137 | Cyclopropyl | 3 | 2,6-(Me)₂ | CH₂CH₃ | H |
| 138 | Et | 4 | 2,6-(Me)₂ | CH₂CH₃ | H |
| 139 | nPr | 4 | 2,6-(Me)₂ | CH₂CH₃ | H |

TABLE 4

Structure: R¹-pyridazinyl-piperazinyl-(CH₂)₂-O-phenyl-C(X²)=N-O-X¹

| Compd No | R¹ | Position of Oxime ether on phenyl ring | X¹ | X² |
|---|---|---|---|---|
| 27 | Cl | 4 | CH₂CH₃ | H |
| 64 | H | 4 | CH₂CH₃ | H |
| 65 | H | 3 | CH₂CH₃ | H |
| 66 | H | 4 | CH₂CH=CH₂ | H |
| 67 | Me | 4 | CH₃ | H |
| 68 | Me | 4 | CH₂CH₃ | H |
| 69 | Me | 4 | CH₂CH=CH₂ | H |
| 70 | Me | 3 | CH₃ | H |
| 71 | Me | 3 | CH₂CH₃ | H |
| 72 | Me | 3 | CH₂CH=CH₂ | H |
| 73 | Cl | 4 | CH₃ | H |
| 74 | Cl | 4 | CH₂CH=CH₂ | H |
| 75 | Cl | 3 | CH₃ | H |
| 76 | Cl | 3 | CH₂CH₃ | H |
| 77 | Cl | 3 | CH₂CH=CH₂ | H |
| 78 | CF₃ | 4 | CH₃ | H |
| 79 | CF₃ | 4 | CH₂CH₃ | H |
| 80 | CF₃ | 4 | CH₂CH=CH₂ | H |
| 81 | CF₃ | 3 | CH₃ | H |
| 82 | CF₃ | 3 | CH₂CH₃ | H |
| 83 | CF₃ | 3 | CH₂CH=CH₂ | H |
| 135 | Me | 4 | CH₂CH₂CH₃ | H |
| 136 | Me | 3 | CH₂CH₂CH₃ | H |
| 148 | Cl | 4 | CH₂CH₂CH₃ | H |
| 149 | Cl | 3 | CH₂CH₂CH₃ | H |

TABLE 5

Structure: R¹-pyridazinyl-piperidinyl-(CH₂)n-O-phenyl-CH=N-O-X¹

| Compd No | R¹ | n | Position of Oxime ether on Phenyl ring | X¹ |
|---|---|---|---|---|
| 28 | Cl | 1 | 4 | CH₂CH₃ |
| 140 | Cl | 2 | 4 | CH₃ |
| 141 | Cl | 2 | 4 | Allyl |
| 142 | Cl | 2 | 4 | Ethyl |
| 150 | Cl | 3 | 4 | Ethyl |
| 151 | Cl | 3 | 4 | Allyl |
| 164 | CF₃ | 3 | 4 | Methyl |
| 165 | CF₃ | 3 | 4 | Ethyl |
| 166 | CF₃ | 3 | 4 | Allyl |
| 167 | CF₃ | 3 | 3 | Methyl |
| 168 | CF₃ | 3 | 3 | Ethyl |
| 169 | CF₃ | 3 | 3 | Allyl |
| 170 | Me | 3 | 4 | Allyl |
| 171 | Me | 3 | 3 | Methyl |
| 172 | Me | 3 | 3 | Ethyl |
| 173 | Me | 3 | 3 | Allyl |
| 174 | Cl | 1 | 4 | Methyl |
| 175 | Cl | 1 | 4 | Allyl |
| 176 | Cl | 1 | 3 | Methyl |
| 177 | Cl | 1 | 3 | Ethyl |
| 178 | Cl | 1 | 3 | Allyl |
| 179 | CF₃ | 1 | 4 | Methyl |
| 180 | CF₃ | 1 | 4 | Ethyl |
| 181 | CF₃ | 1 | 4 | Allyl |
| 182 | CF₃ | 1 | 3 | Methyl |
| 183 | CF₃ | 1 | 3 | Ethyl |
| 184 | CF₃ | 1 | 3 | Allyl |

TABLE 6

Structure: Het-N-piperidinyl(Z)-(CH₂)₂-O-phenyl-CH=N-O-X¹

| Compound No | Het | Z | X¹ |
|---|---|---|---|
| 84 | 5-CF₃-2-Pyridyl | CH | Ethyl |
| 152 | 5-Chloro-2-Pyrazinyl | N | Ethyl |
| 153 | 5-CF₃-1,3,4-thiadiazol-2-yl | CH | Methyl |
| 154 | 5-CF₃-1,3,4-thiadiazol-2-yl | CH | Ethyl |
| 157 | 5-Methyl-1,3,4-thiadiazol-2-yl | CH | Methyl |
| 158 | 5-Methyl-1,3,4-thiadiazol-2-yl | CH | Ethyl |
| 159 | 5-Chloro-2-Pyrazinyl | CH | Methyl |
| 160 | 5-Chloro-2-Pyrazinyl | CH | Ethyl |
| 196 | 6-Methyl-2-Pyridyl | CH | Ethyl |
| 197 | 4-EtO₂C-Thiazol-2-yl | CH | Methyl |
| 198 | 4-Ethoxycarbonyl-2-Thiazolyl | CH | Ethyl |
| 199 | 6-Chloro-2-Pyrazinyl | CH | Methyl |
| 200 | Benzoxazol-2-yl | CH | Methyl |
| 201 | Benzoxazol-2-yl | CH | Ethyl |
| 202 | 4,6-Dimethoxy-1,3,5-Triazin-2-yl | CH | Methyl |
| 203 | 4,6-Dimethoxy-1,3,5-Triazin-2-yl | CH | Ethyl |
| 204 | 5-Ethyl-2-Pyrimidin-2-yl | CH | Methyl |
| 205 | 5-Ethyl-2-Pyrimidin-2-yl | CH | Ethyl |
| 206 | Benzothiazol-2-yl | CH | Methyl |
| 207 | Benzothiazol-2-yl | CH | Ethyl |
| 210 | 6-Chloro-2-quinoxalinyl | CH | Ethyl |
| 212 | 6-Chloro-5-Methyl-3-Pyridazinyl | CH | Ethyl |

TABLE 7

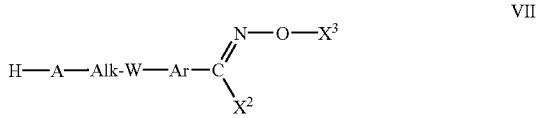

| Compd No | Het | A | n | $X^1$ |
|---|---|---|---|---|
| 147 | 6-Cl-3-Pyridazinyl | NH | 5 | Ethyl |
| 161 | 6-Cl-3-Pyridazinyl | NMe | 5 | Ethyl |
| 162 | 6-Cl-3-Pyridazinyl | NH | 6 | Ethyl |
| 163 | 6-Cl-3-Pyridazinyl | NH | 4 | Ethyl |
| 194 | 6-Cl-3-Pyridazinyl | NMe | 6 | Methyl |
| 195 | 6-Cl-3-Pyridazinyl | NMe | 4 | Ethyl |
| 209 | 6-Cl-3-Pyridazinyl | O | 5 | Ethyl |
| 211 | 6-Cl-2-Quinoxalinyl | Direct bond | 0 | Ethyl |

TABLE 8

| Compound No | $R^1$ | n | $X^1$ |
|---|---|---|---|
| 155 | Me | 2 | Ethyl |
| 156 | Me | 2 | Methyl |

The compounds of the present invention may be prepared using methods analogous to those described in the prior art. For example, compounds in which the Het radical is of formula (a-1) may be prepared using methodology analogous to the processes described in U.S. Pat. Nos. 4,992,433, 5,112,825 and 5,100,893. Similarly, compounds in which Het is (a-2), (a-3), (a-4), (a-5) or (a-6) may be prepared using methodology similar to that described in U.S. Pat. No. 5,070,090 and Australian patent No. 629172, and compounds in which Het is (a-7) or (a-8) may be prepared in accordance with methodology similar to that described in U.S. Pat. No. 5,364,865.

In one method the compounds of the present invention are prepared via an intermediate of formula VII:

where A, Alk, W, Ar and $X^2$ are as described above, and $X^3$ is $X^1$ or an oxime protecting group.

This intermediate may be prepared using methodology similar to that described in U.S. Pat. No. 5,231,184. In one example intermediates of formula VII, when W is O, are prepared by the reaction of compounds of the formula P-A-Alk-OH or P-A-Alk-L with hydroxy aromatic compounds of formula VIII.

HO-Ar-C($X^2$)=NO-$X^3$    VIII where Ar, $X^1$, $X^2$ and $X^3$ are as defined above, P is H or a protecting group, and L is a leaving group. Removal of the protecting group P in the reaction product affords the reactive intermediates of formula VII.

Examples of suitable protecting groups P in compounds of formula P-A-Alk-OH or P-A-Alk-L include benzyl or acyl moieties which can be introduced and removed by standard methods (see "Protective Groups in Organic Synthesis" Theodora Green, Wiley Interscience, 1981).

The intermediate of formula VII may be reacted with a compound of formula Het-L, where Het is as defined above and L is a suitable leaving group, optionally followed by deprotection and/or conversion of $X^3$ to $X^1$, to afford a compound of formula I. This N-alkylation reaction can be conducted using procedures known to the art, such as under the conditions described in U.S. Pat. No. 5,231,184 for performing analogous N-alkylations.

The intermediates of formula VII are novel and represent a further aspect of the present invention.

Examples of suitable leaving groups include halogen, such as fluoro, chloro, bromo and iodo, and halogen-like groups such as p-toluenesulphonyloxy and methanesulphonyloxy.

Another method for the preparation of the compounds of formula I involves the addition of an alkoxyamine $H_2NOX^1$ to an aldehyde or ketone of formula IX Het-A-Alk-W-Ar-C(=O)$X^2$    IX where Het, A, Alk, W, Ar $X^1$ and $X^2$ are as defined for formula I above. This reaction is carried out using standard conditions, such as in an aqueous or alcoholic solvent at ambient temperature or with warming.

A further method of forming the compounds of the invention involves reaction of a carbonyl compound of formula IX with hydroxylamine to give of an oxime of formula X, Het-A-Alk-W-Ar-C(50 NOH)$X^2$    X which is then O-alkylated with a compound L-$X^1$, where L is a leaving group and $X^1$ is as defined for formula I.

An additional method of preparing certain compounds of the invention of formula Ia (Compounds for formula I where W=O) involves condensing an oxime ether of formula XI with a suitable precursor of formula (XII)

HO-Ar-C($X^2$)=NO-$X^1$+Het-A-Alk-OH→Het-A-Alk-O-Ar-C($X^2$)=N-O-$X^1$    (XI) (XII) (Ia)

using Mitsunobu Reaction conditions (see Chemical Syntheses, Vol. 42, p 335, 1992) and where Het, A, Alk, Ar, $X^1$ and $X^2$ are as defined for formula I.

Methods for the preparation of intermediate carbonyl compounds of formulae IX have been described in the chemical literature (U.S. Pat. Nos. 4,992,433, 4,451,476). Compounds of formula XI are well known in the chemical literature (eg German Patent DE 3,601,564). Several references, including U.S. Pat. Nos. 5,112,825 and 5,242,924 describe methods for the preparation of various compounds of formula XII.

The compounds of the present invention are useful in the prevention or treatment of picornoviral infections in mammals, particularly humans.

Accordingly in a further aspect the invention provides a method for the treatment or prophylaxis of a picornaviral infection in a mammal including the step of administering an effective amount of a compound of formula I.

The picornavirus infection may be caused by any virus of the family Picornaviridae. Representative family members include human rhinoviruses, polioviruses, enteroviruses including coxsackieviruses and echoviruses, hepatovirus, cardioviruses, apthovirus, hepatitis A and other picornaviruses not yet assigned to a particular genus, including one or more of the serotypes of these viruses. Preferably the invention is used in the prevention or treatment of infection caused by one or more serotypes of rhinovirus.

Without wishing to be limited by theory it is believed that the oxime ether moiety of the compound of formula I may be involved in hydrogen bonding with an asparagine residue generally present near the opening of the hydrophobic pocket and that this interaction enhances the binding of the compounds in the capsid pocket, relative to the prior art compounds. It is further believed that the oxime ether bond may be more resistant to hydrolysis and esterase activity than the ester bond of pirodavir, and that this may allow more flexibility in the methods of administration of the compound to the site of activity, than available for readily hydrolysable pirodavir. In particular it may allow oral administration of the compounds or reduce metabolism in the nasal mucosa following topical administration.

The salts of the compound of formula I are preferably pharmaceutically acceptable, but it will be appreciated that non-pharmaceutically acceptable salts also fall within the scope of the present invention, since these are useful as intermediates in the preparation of pharmaceutically acceptable salts. The pharmaceutically acceptable salts may include conventional non-toxic salts or quarternary ammonium salts of these compounds, which may be formed, e.g. from organic or inorganic acids or bases. Examples of such acid addition salts include, but are not limited to, those formed with pharmaceutically acceptable acids such as acetic, propionic, citric, lactic, methanesulphonic, toluenesulphonic, benzenesulphonic, salicyclic, ascorbic, hydrochloric, orthophosphoric, sulphuric and hydrobromic acids. Base salts includes, but is not limited to, those formed with pharmaceutically acceptable cations, such as sodium, potassium, lithium, calcium magnesium, ammonium and alkylammonium. Also, basic nitrogen-containing groups may be quaternised with such agents as lower alkyl halides, such as methyl, ethyl, propyl, and butyl chlorides, bromides and iodides; dialkyl sulfates like dimethyl and diethyl sulfate; and others.

The compounds of the invention may be in crystalline form or as solvates (e.g. hydrates) and it is intended that both forms are within the scope of the present invention. Methods of solvation are generally known within the art.

Pharmaceutically acceptable derivatives may include any pharmaceutically acceptable salt, hydrate or any other compound or prodrug which, upon administration to a subject, is capable of providing (directly or indirectly) a compound of formula I or an antivirally active metabolite or residue thereof.

Any compound that is a prodrug of a compound of formula I is within the scope and spirit of the invention. The term "pro-drug" is used in its broadest sense and encompasses those derivatives that are converted in vivo to the compounds of the invention. Such derivatives would readily occur to those skilled in the art, and include, for example, compounds where a free hydroxy group is converted into an ester derivative or a ring nitrogen atom is converted to an N-oxide. Examples of ester derivatives include alkyl esters, phosphate esters and those formed from amino acids, preferably valine.

It will be appreciated that some derivatives of the compound of formula I may have an asymmetric centre, and therefore are capable of existing in more than one stereoisomeric form. The invention extends to each of these forms individually and to mixtures thereof, including racemates. The isomers may be separated conventionally by chromatographic methods or using a resolving agent. Alternatively the individual isomers may be prepared by asymmetric synthesis using chiral intermediates.

The invention also provides the use of a compound of formula I in the manufacture of a medicament for the treatment or prophylaxis of picornavirus infection.

While it is possible that, for use in therapy, a compound of the invention may be administered as the neat chemical, it is preferable to present the active ingredient as a pharmaceutical formulation.

In view of the general lipophilic nature of the compounds they are particularly suitable to oral forms of administration, however other forms of administration are also envisaged.

The invention thus further provides pharmaceutical formulations comprising a compound of the invention or a pharmaceutically acceptable salt or derivative thereof together with one or more pharmaceutically acceptable carriers therefor and, optionally, other therapeutic and/or prophylactic ingredients. The carrier(s) must be acceptable" in the sense of being compatible with the other ingredients of the formulation and not deleterious to the recipient thereof.

The compounds of this invention may also be useful in combination with known anti-viral or anti-retroviral agents or other pharmaceuticals used in the treatment of viral infections.

Representative examples of these additional pharmaceuticals include immunomodulators, immunostimulants, antibiotics and anti-inflammatory agents. Exemplary anti-viral agents include zanamivir, rimantidine, amantidine, ribavirin, AZT, 3TC, (−) FrC, acyclovir, famciclovir, penciclovir, ddI, ddC, ganciclovir, saquanivir, loviride, other non-nucleotide reverse transcriptase (RT) inhibitors and protease inhibitors, antiviral and antireceptor antibodies and receptor analogues, such as ICAM-1. Exemplary immunomodulators and immunostimulants include various interleukins, cytokines and antibody preparations. Exemplary antibiotics includes antifungal agents and antibacterial agents. Exemplary anti-inflammatory agents include glucocorticoids and non-steroidal anti-inflammatory compounds.

Pharmaceutical formulations include those suitable for oral, rectal, nasal, topical (including buccal and sub-lingual), vaginal or parenteral (including intramuscular, subcutaneous and intravenous) administration or in a form suitable for administration by inhalation or insufflation. The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing ten (10) milligrams of active ingredient or, more broadly, 0.1 to two hundred (200) milligrams, per tablet, are accordingly suitable representative unit dosage forms. The compounds of the present invention can be administrated in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomising spray pump. To improve nasal delivery and retention the compounds according to the invention may be encapsulated with cyclodextrins, or formulated with their agents expected to enhance delivery and retention in the nasal mucosa.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP).

Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size for example of the order of 1 to 10 microns or less. Such a particle size may be obtained by means known in the art, for example by micronization.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Liquids or powders for intranasal administration, tablets or capsules for oral administration and liquids for intravenous administration are preferred compositions.

The invention will now be described with reference to the following examples which illustrate some preferred aspects of the present invention. However it is to be understood that the particularity of the following description of the invention is not to supersede the generality of the preceding description of the invention.

EXAMPLES

Example 1

Preparation of 4-{2-[1-(6-Chloro-3-pyridazinyl)4-piperidinyl]ethoxy}benzaldehyde O-ethyloxime (Compound 1)

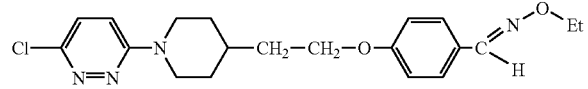

4-{2-[1-(6-Chloro-3-pyridazinyl)piperidinyl]ethoxy}benzaldehyde (Intermediate IIa) was prepared from 4-hydroxybenzaldehyde and 2-[1-(6-Chloro-3-pyridazinyl)-4-piperidinyl]ethanol using a Mitsunobu Reaction and following the general methods described in U.S. Pat. No. 4,992,433. The aldehyde (60 mg, 0.17 mmol) was dissolved in ethanol (5 ml) with stirring at room temperature and a solution of ethoxyanine in water (0.5 ml, 50% EtONH$_2$) was added. The reaction was stirred at room temperature for 2 days and then concentrated on a rotary evaporator and the residue was purified by chromatography (silica gel 18g) using chloroform as eluent. The first compound to elute was the O-ethyloxime (1) which was obtained as a pale cream solid (30mg, 44%).

$^1$H nmr spectrum (CDCl$_3$) δ (ppm): 1.20–1.40 (m, 5H); 1.65–1.95 (m, 5H); 2.95 (bt, 2H); 4.05 (t, 2H); 4.18 (q, 2H); 4.35 (bd, 2H); 6.87 (d, 2H); 6.90 (d, 1H); 7.16 (d, 1H); 7.52 (d, 2H); 8.02 (s, 1H).

Mass Spectrum (ESI) 389 (M+1)$^+$

Example 2

Preparation of 4-{2-[1-(6-Methyl-3-pyridazinyl)-4-piperidinyl]ethoxy}benzaldehyde O-ethyloxime (Compound 2)

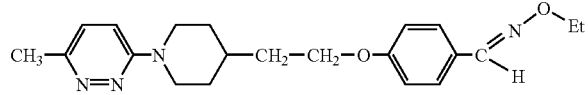

(a) A solution of 4-hydroxybenzaldehyde (100 mg, 0.88 mmol) and 50% O-ethylhydroxylamine aqueous solution (0.6 ml, 4.9 mmol) in dioxane (2 ml) was stirred under an atmosphere of argon at room temperature for 16 hours and then heated at 90–100° for 3 hours when thin layer chromatography (silica, dichloromethane) indicated the reaction was complete. The solution was evaporated to dryness and the residue partitioned between ethyl acetate (20 ml) and water (5 ml). The organic layer was washed with water, dried (Na$_2$SO$_4$) and evaporated to afford 4-hydroxybenzaldehyde O-ethyloxime (125 mg, 92.5%).

(b) To a solution of 4-hydroxybenzaldehyde O-ethyloxime (49 mg, 0.4 mmol), 2-[1-6-methyl-3-pyridazinyl)-4-piperidinyl]ethanol (88 mg, 0.4 mmol) and triphenylphosphine (115 mg, 0.44 mmol) in dry tetrahydrofuran (THF) (5 ml) under argon at room temperature was added dropwise diisopropylazodicarboxylate (89 mg, 0.44 mmol) in dry THF. The resulting solution was stirred at 20° for 24 hours and the solvent was then removed on a rotary evaporator. The residue was chromatographed on silica gel, using firstly ethyl acetatehexane (1:1) as eluent to give the product (Compound 2) as a white solid (103 mg, 70%).

$^1$H nmr spectrum (CDCl$_3$) δ (ppm): 1.20–1.40 (m, 5H); 1.65–1.95 (m, 5H); 2.53 (s, 3H); 2.95 (bt, 2H); 4.05 (t, 2H); 4.18 (q, 2H); 4.35 (bd, 2H); 6.88 (d, 2H); 6.90 (d, 1H); 7.05 (d, 1H); 7.52 (d, 2H); 8.02 (s, 1H).

Mass Spectrum (ESI) 369 (M+1)$^+$

Example 3

The Compound No's 5, 8, 11, 12, 13, 14, 15, 20, 21 and 22–25 from Tables 1 and 3 of the invention were prepared following essentially the same method as described in Example 1 for Compound 1, using the appropriate carbonyl compound (Het-A-Alkylene-O-Aryl-C(X$^2$)=O and alkoxyamine (H$_2$NO-X$^1$). The compounds were purified by chromatography on silica gel and characterised by their nuclear magnetic resonance (nmr) spectra and Mass Spectral (MS) data. For convenience the nmr and MS data are recorded in Table 9 below.

TABLE 9

| Compd Number | MS data (ESI) | NMR data: Proton Chemical Shift, δ in ppm (CDCl$_3$) |
|---|---|---|
| 5 | 419 (M+1) | 1.20–1.40(m, 5H); 1.65–1.95(m, 5H); 3.0(bt, 2H); 3.89(s, 3H); 4.08(t, 2H); 4.21(q, 2H); 4.35(bd, 2H); 6.85(d, 1H); 6.92(d, 1H); 7.0(dd, 1H); 7.15(d, 2H); 7.24(d, 1H); 8.02(s, 1H) |
| 8 | 375 (M+1) | 1.30(m, 2H); 1.65–1.95(m, 5H); 2.95(t, 2H); 3.93(s, 3H); 4.05(t, 2H); 4.40(d, 2H); 6.88(d, 2H); 7.0(d, 1H); 7.24(d, 1H); 7.51(d, 2H); 8.02(s, 1H) |
| 11 | 403 (M+1) | 0.95(t, 3H); 1.30(m, 2H); 1.65–1.95(m, 5H); 1.77(t, 2H); 2.95(t, 2H); 3.92–4.20(m, 4H); 4.35(d, 2H); 6.85(d, 2H); 6.90(d, 1H); 7.20(d, 1H); 7.50(d, 2H); 8.07(s, 1H) |
| 12 | 403 (M+1) | 1.25(d, 6H); 1.30(m, 2H); 1.65–1.95(m, 5H); 2.95(t, 2H); 4.05(t, 2H); 4.35(d, 2H); 4.42(m, 1H); 6.85(d, 2H); 6.90(d, 1H); 7.20(d, 1H); 7.51(d, 2H); 8.05(s, 1H). |
| 13 | 401 (M+1) | 1.30(m, 2H); 1.65–1.95(m, 5H); 2.95(t, 2H); 4.05 (t, 2H); 4.35(d, 2H); 4.66(d, 2H); 5.25(dd, 1H); 5.38(dd, 1H); 6.08(m, 1H); 6.85(d, 2H); 6.90(d, 1H); 7.20(d, 1H); 7.50(d, 2H); 8.13(s, 1H) |
| 14 | 400 (M+1) | 1.30(m, 2H); 1.65–1.95(m, 5H); 2.95(t, 2H); 4.05 (t, 2H); 4.35(d, 2H); 4.75(s, 2H); 6.85(d, 2H); 6.90(d, 1H); 7.20(d, 1H); 7.50(d, 2H); 8.07(s, 1H) |
| 15 | 451 (M+1) | 1.30(m, 2H); 1.65–1.95(m, 5H); 2.95(t, 2H); 4.05 (t, 2H); 4.35(d, 2H); 5.20(s, 2H); 6.85(d, 2H); 6.88(d, 1H); 7.20(d, 1H); 7.41(s, 5H); 7.50(d, 2H); 8.08(s, 1H) |
| 20 | Not recorded | 1.15–1.45(m, 5H); 1.65–1.95(m, 5H); 2.95(bt, 2H); 3.50(q, 2H); 3.55–3.80(m, 6H); 4.05(t, 2H); 4.3(t, 4H); 4.36(d, 2H); 6.85(d, 2H); 6.90(d, 2H); 7.2(d, 1H); 7.45(d, 2H); 8.05(s, 1H) |
| 21 | Not recorded | 1.15–1.45(m, 5H); 1.65–1.95(m, 5H); 3.0(bt, 2H); 4.05(t, 2H); 4.22(q, 2H); 4.30(bd, 2H); 4.83(q, 2H); 6.90(d, 2H); 7.04(d, 1H); 7.20(d, 1H); 7.53(d, 2H); 8.05(s, 1H) |

TABLE 9-continued

| Compd Number | MS data (ESI) | NMR data: Proton Chemical Shift, δ in ppm (CDCl₃) |
|---|---|---|
| 22 | 303 (M+1) | 2.2(m, 2H); 2.26(2xs, 9H); 2.99(t, 2H); 3.81(t, 2H); 3.94(s, 3H); 5.87(s, 1H); 7.23(s, 2H); 7.95(s, 1H) |
| 23 | 329 (M+1) | 2.2(m, 2H); 2.26(2xs, 9H); 2.99(t, 2H); 3.81(t, 2H); 4.65(m, 2H); 5.2–5.4(m, 2H); 6.0–6.15 (m, 1H); 5.87(s, 1H); 7.23(s, 2H); 8.01(s, 1H) |
| 24 | Not recorded | 1.3(t, 3H); 2.2(m, 2H); 2.27(2xs, 9H); 2.99(t, 2H); 3.81(t, 2H); 4.18(q, 2H); 5.87(s, 1H); 7.23(s, 2H); 7.96(s, 1H) |
| 25 | 401 (M+23) | 2.2(m, 2H); 2.26(2xs, 9H); 2.99(t, 2H); 3.81(t, 2H); 5.19(s, 2H); 5.87(s, 1H); 7.23(s, 2H); 7.3–7.45(m, 5H); 8.04(s, 1H) |

Example 4

The Compound No's 3, 4, 6, 7, 9, 10, 16, 17, 18, 19 from Tables 1 and 2 of the invention were prepared using essentially the same method as described in Example 2 for Compound 2 and were obtained in yields of 61–73%. The compounds were purified by column chromatography on silica gel and characterised by their nuclear magnetic resonance (nmr) spectra and Mass Spectral (MS) data. For convenience the nmr and MS data are recorded in Table 10 below.

TABLE 10

| Compound Number | MS data (ESI) | NMR data: Proton Chemical Shift, δ in ppm (CDCl₃) |
|---|---|---|
| 3 | 403 (M+1) | 1.20–1.40(m, 5H); 1.65-1.95(m, 5H); 2.15(s, 3H); 2.95(t, 2H); 4.05(t, 2H); 4.23(q, 2H); 4.35(d, 2H); 6.85(d, 2H); 6.94(d, 1H); 7.18(d, 1H); 7.60(d, 2H) |
| 4 | 383 (M+1) | 1.20–1.40(m, 5H); 1.65–1.95(m, 5H); 2.15(s, 3H); 2.53(s, 3H); 2.95(t, 2H); 4.05(t, 2H); 4.18(q, 2H); 4.35(d, 2H); 6.89–6.90(2xd, 3H); 7.12(d, 1H); 7.61(d, 2H) |
| 6 | 463 (M+1) | 1.20–1.40(m, 5H); 1.65–1.95(m, 5H); 2.15(s, 3H); 2.95(t, 2H); 3.90(s, 6H); 4.05(t, 2H); 4.22(q, 2H); 4.35(d, 2H); 6.85(s, 2H); 6.90(d, 1H); 7.14(d, 1H) |
| 7 | 355 (M+1) | 1.30(m, 2H); 1.65–1.95(m, 5H); 2.53(s, 3H); 2.95(t, 2H); 3.93(s, 3H); 4.05(t, 2H); 4.35(d, 2H); 6.88(d, 2H); 6.90(d, 1H); 7.05(d, 1H); 7.51(d, 2H); 8.05(s, 1H) |
| 9 | 369 (M+1) | 1.32(m, 2H); 1.65–1.95(m, 5H); 2.15(s, 3H); 2.49(s, 3H); 2.95(t, 2H); 3.93(s, 3H); 4.06(t, 2H); 4.35(d, 2H); 6.88(d, 2H); 7.15(d, 1H); 7.25(d, 1H); 7.55(d, 2H) |
| 10 | 403 (M+1) | 1.02–1.40(m, 5H); 1.65–1.95(m, 5H); 2.70(q, 2H); 2.95(t, 2H); 3.91(s, 3H); 4.05(t, 2H); 4.35(d, 2H); 6.82(d, 2H); 6.88(d, 1H); 7.15(d, 1H); 7.55(d, 2H) |
| 16 | 375 (M+1) | 1.30(m, 2H); 1.65–1.95(m, 5H); 2.95(t, 2H); 3.93(s, 3H); 4.03(t, 2H); 4.35(d, 2H); 6.85(d, 2H); 7.03(d, 1H); 7.12(d, 1H); 7.18(d, 1H); 7.28 (d, 1H); 8.03(s, 1H) |
| 17 | 405 (M+1) | 1.30(m, 2H); 1.65–1.95(m, 5H); 2.95(t, 2H); 3.85(s, 3H); 3.93(s, 3H); 4.15(t, 2H); 4.35(d, 2H); 6.85(d, 1H); 6.90(d, 1H); 6.98(dd, 1H); 7.16(d, 1H); 7.23(d, 1H); 8.0(s, 1H) |
| 18 | 403 (M+1) | 1.30(m, 2H); 1.65–1.95(m, 5H); 2.25(s, 6H); 3.0(t, 2H); 3.85(t, 2H); 3.91(s, 3H); 4.35(d, 2H); 6.92(d, 1H); 7.10(d, 1H); 7.26(s, 2H); 8.0(s, 1H) |
| 19 | 419 (M+1) | 1.30(m, 2H); 1.65–1.95(m, 5H); 2.15(s, 3H); 2.95(t, 2H); 3.90(s, 3H); 3.95(s, 3H); 4.07(t, 2H); 4.35(d, 2H); 6.82(d, 2H); 6.90(d, 1H); 6.99 (dd, 1H); 7.14(d, 1H); 7.26(d, 1H) |

Example 5

Preparation of 3,5-Dimethyl-[4-{3-(3-Phenyl-5-isoxazolyl)propoxy)]benzaldehyde O-ethyloxime (Compound 127)

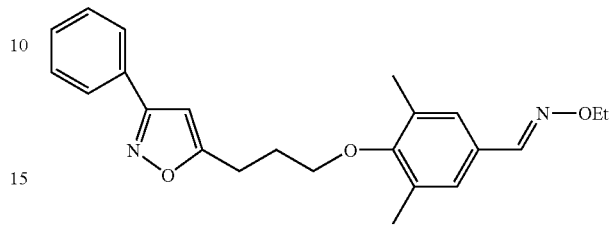

(a) Condensation of 4-pentyn-1-ol and 4-hydroxy-3,5-dimethylbenzaldehyde O-ethyloxime using Mitsunobu Reaction conditions (see for example J. Med. Chem., 36, 3240, 1993 and references cited therein) gave 3,5-dimethyl4-(4-pentyn-1-yloxy)benzaldehyde O-ethyl oxime in good yield.

(b) Isoxazole ring formation (also see J. Med. Chem., 38, 1355, 1995)

A solution of benzaldehyde oxime (45 mg, 0.372 mmol) in DMF (0.5 ml) was added dropwise to a solution of N-chlorosuccinimide (50 mg, 0.374 mmol) and pyridine (1 drop) in DMF (0.5 ml), keeping the temperature between 25–30° C. The resulting solution was allowed to stir at room temperature for 90 minutes. To this was added a solution of 3,5-dimethyl-4-(4-pentyn-1-yloxy)benzaldehyde O-ethyl oxime (49 mg, 0.189 mmol) in DMF (0.5 mL, the resulting solution was then heated at 85–90° C. for 10 minutes. To this was added, dropwise over 10 minutes, a solution of triethylamine (54 µl, 0.386 mmol) in DMF (0.5 ml), the resulting solution was then heated at 85–90° C. for 1 hour. The reaction was cooled and the solvent removed in vacuo. The residue was partitioned between ethyl acetate (50 ml) and water (15 ml). The organic phase was washed with brine (15 mL), dried (MgSO₄), filtered and concentrated in vacuo. Purification by flash chromatography (Ethyl acetate/Hexane 5%) gave the product (Compound 127) as a clear oil (23 mg, 32%). The structure was confirmed by the ¹H nmr spectrum which is given in Table 11 below.

Example 6

The Compound No's 130, 131, 132, 133, 137, 138, and 139 from Table 3 of the invention were prepared using the appropriate oxime and essentially the same method as described in Example 5 for Compound 127. The compounds were purified by column chromatography on silica gel and characterised by their nuclear magnetic resonance (nmr) spectra and Mass Spectral (MS) data which are summarised in Table 11 below.

Example 7

Preparation of 2-(1-(6 methyl-3-pyridazinyl)-4-piperidinylethoxy)-thiazole-4-carboxaldehyde O-ethyl oxime (Compound No.155)

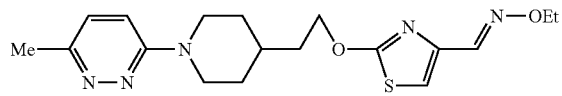

(a) Sodium borohydride (690 mg, 18 mmol) was added as a single portion to a solution of ethyl 2-chloro-4-thiazolecarboxylate (1.6 g, 9 mmol) in ethanol (70 ml) at 0° C., then the mix was allowed to warm to room temperature with stirring overnight. The reaction was acidified to pH 5 with IN HCl and concentrated under vacuum, then the white residue was partitioned between water (125 ml) and ethyl acetate (3×300 ml). The organic phase was washed with brine and dried ($Na_2SO_4$), then the solvents were removed. Chromatography of the residue on silica gel (15 g, eluent 15%/–30% hexane/ethyl acetate) gave 2-chloro-4-hydroxymethylthiazole (850 mg, 5.5 mmol) in 63% yield as a clear oil, $^1$H nmr, 4.72 (s, 2H), 7.11 (s, 1H).

(b) Tert-butyldimethylsilylchloride (1.07 g, 7.1 mmol) was added as a single portion to a solution of the hydroxymethylthiazole (840 mg, 5.6 mmol) and imidazole (500 mg, 7.34 mmol) in anhydrous DMF (20 ml). The solution was stirred overnight under an argon atmosphere. Solvents were removed under vacuum and the residue was partitioned between water (100 ml) and ethyl acetate (500 ml). The organic layer was washed with brine, dried ($MgSO_4$) and concentrated under reduced pressure. The residue was chromatographed on silica gel (200 g; eluent 5%/50%DCM/hexane) to give 2-chloro-4-t-butyldimethylsilyloxymethylthiazole (1.29 g, 4.9 mmol) in 87% yield, $^1$H nmr 0.11 (s, 6H), 0.94 (s, 9H), 4.78 (s, 2H), 7.08 (s, 1H).

(c) A suspension of sodium hydride (60%, 135 mg, 3.4 mmol) and 1-(6-methyl-3-pyridazinyl)-4-(2-hydroxyethyl)-piperidine (250 mg, 1.1 mmol) in dimethoxyethane (DME; 4 ml) was stirred at room temperature for 2 hr. A solution of 2-chloro-4-t-butyldimethylsilyloxymethylthiazole (385 mg, 1.46 mmol) in DME (1 ml) was added and the mixture stirred at reflux under argon for 5 hr then at room temperature overnight. The mixture was diluted with ether, filtered and then concentrated. The residue was chromatographed on silica gel (25 g; eluent 30%–50% ethyl acetate/hexane) to give 2-1 -(6-methyl-3-pyridazinyl)-4-piperidinylethyl-1-oxy)-4t-butyldimethylsilyloxymethylthiazole (274 mg, 54%), $^1$H nmr, 0.11 (s, 6H), 0.94 (s, 9H), 1.3–1.87 (m, 7H), 2.58 (s, 3H), 2.93 (t, 2H), 4.31–4.35 (m, 2H), 4.48 (t, 2H), 4,64 (s, 2H), 6.51 (s, 1H), 6.93 (d, 1H), 7.11 (d, 1H).

(d) A solution of tetrabutylammonium fluoride (1 M in THF, 0.6 ml, 0.6 mmol) was added dropwise to a solution of 2-(1-6-methyl-3-pyridazinyl)-4-piperidinylethyl-1-oxy)-4-t-butyldimethylsilyloxymethylthiazole (274 mg, 0.6 mmol) in THF (10 ml) and the reaction was stirred under argon overnight. The mixture was partitioned between water (10 ml) and ethyl acetate (40 ml) then the organic layer was washed with brine, dried ($MgSO_4$) and concentrated. The residue was chromatographed on silica gel (25 g; eluent 0%–10% isopropanol/ethyl acetate) to give 2-(1-(6-methyl-3-pyridazinyl)-4-piperidinylethoxy)-4-hydroxymethylthiazole (157 mg, 0.47 mmol) in 76% yield, $^1$H nmr, 1.78–1.9 (m, 5H), 2.51 (s, 3H), 2.96 (t, 2H), 4.31 4.37 (m, 4H), 4.58 (s, 2H), 6.02 (s, 1H), 7.22 (d, 1H), 7.30 (d, 1H).

(e) A solution of anhydrous DMSO (80 μl, 1.13 mmol) in DCM (1 ml) was added to a solution of oxalyl chloride (45 μl, 0.5 mmol) in DCM (1 ml) at –60° C. After 15 min a solution of 2-(1-(3-methyl-6-pyridazinyl)-4-piperidinylethyl-1-oxy)-4-hydroxymethylthiazole (157 mg, 0.5 mmol) in DCM (2 ml) was added. The reaction was stirred at –50° C. for 10 min then triethylamine (325 μl, 2.33 mmol) was added and the reaction allowed to warm to room temperature. The mixture was partitioned between DCM (150 ml) and dilute sodium bicarbonate solution (75 ml) then washed with brine, dried ($MgSO_4$) and concentrated. The residue was adsorbed onto silica gel and chromatographed on silica gel (15 g; eluent 65% ethyl acetate/hexane) to give 2-(1-(6-methyl-3-pyridazinyl)-4-piperidinylethoxy) thiazole-4-carboxaldehyde (103 mg, 66%), $^1$H nmr; 1.3–1.9 (m, 7H), 2.63 (s, 3H), 2.94 (m, 2H), 4.34 4.38 (m, 2H), 4.59 (t, 2H), 7.04 (d, 1H), 7.20 (d, 1H), 7.61 (s, 1H), 9.74 (s, 1H).

(f) The O-ethyl oxime ether (Compound 155) of the aldehyde in part (e) was prepared from by reaction with ethoxyamine following similar conditions to those described in Example 1 and the spectra for Compound 155 are given in Table 11 below.

Example 8

Preparation of 4-{N-6-Chloropyridazinyl)-N-methyl-5-aminopentan-1-oxy}benzaldehyde O-ethyloxime (Compound No. 161)

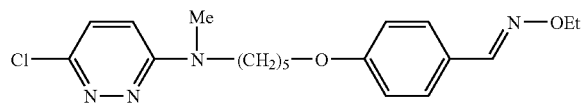

(a) A mixture of 5-amino-1-pentanol (433 mg, 4.2 mmol), dichloropyridazine (1.25 g, 8.39 mmol) and sodium carbonate (890 mg, 8.39 mmol) was stirred in 1,4-dioxane (40 ml) and heated at 70–80° for 3 days under an atmosphere of argon. The solvent was removed under reduced pressure and the residue was partitioned between dichloromethane (300 ml) and water (38 ml). The organic layer was separated, dried and concentrated to give an orange solid which was chromatographed on silica, using hexane/ethyl acetate (1:1). The product, 5-(6chloro-3-pyridazinyl)amino-1-pentanol was isolated as a pale yellow solid (202 mg, 22%).

(b) 5-(6Chloro-3-pyridazinyl)amino-1-pentanol was coupled to 4-hydroxybenzaldehyde using the Mitsunobu Reaction and following essentially the same method as described in Example 2, part (b). The product, 4-{N-6-Chloro-3-pyridazinyl)-5-aminopentan-1-oxy}benzaldehyde, was isolated by chromatography and characterised by its nmr spectrum in $CDCl_3$; 1.65 (m, 2H); 1.76 (m, 2H); 1.90 (m, 2H); 3.45 (t, 2H); 4.15 (t, 2H); 6.92 (d, 1H); 7.10 (d, 2H); 7.30 (d, 1H); 7.89 (d, 2H); 9.86 (s, 1H).

(c) Sodium hydride (10 mg, 0.24 mmol) was added to a solution of 4-{N-(6-Chloro-3-pyridazinyl)-5-aminopentan-1-oxy}benzaldehyde (51 mg, 0.16 mmol) in THF (3.5 ml) and the mixture was stirred at room temperature for 30 minutes. Methyl iodide (50 μl, 0.8 mmol) was added to the reaction mixture and the suspension was stirred at room temperature for 48 hours. The reaction mixture was poured into water (1.5 ml) and concentrated under reduced pressure. The residue was partitioned between water (2 ml) and ethyl acetate (40 ml), shaken thoroughly and the organic layer was separated, dried and evaporated to give a yellow solid.

Purification by chromatography on silica gel (6 g, 30% ethyl acetate/hexane) gave 4-{N-(6-Chloro-3-pyridazinyl)-N-methyl-5-aminopentan-1-oxy}benzaldehyde (16 mg, 30%) as a pale yellow oil.

(d) Reaction of 4-{N-(6-Chloro-3-pyridazinyl)-N-methyl-5-aminopentan-1-oxy}benzaldehyde with ethoxyamine following similar conditions to those in Example 1 gave 4-{N-(6-Chloro-3-pyridazinyl)-N-methyl-5-aminopentan-1-oxy}benzaldehyde O-ethyloxime (Compound 161) as a colourless oil. The nmr and mass spectral data are given below in Table 11.

Example 9

Preparation of 4-{2-[1-{5-Methyl-2-1,3,4-thiadiazinyl}]-4-piperidinyl]ethoxy}benzaldehyde O-ethyloxime (Compound 158)

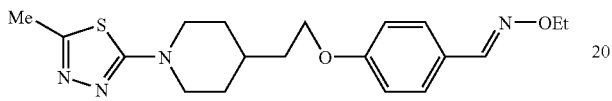

(a) A suspension containing 2-bromo-5-methyl-1,3,4-thiadiazole (Modarai, B., et al. J. Heterocyclic Chem. (1974) 11, 343–5) (100 mg, 0.56 mmol), 4-piperidine ethanol (87 mg, 0.67 mmol) and potassium carbonate (77 mg, 0.56 mmol) was heated overnight at 120° C. The reaction was cooled and the mixture partitioned between water (10 ml) and ethyl acetate (30 ml), then the organic layer was washed with brine, dried (Na$_2$SO$_4$) and concentrated. Chromatography of the residue on silica gel (8 g; eluent 2.5% methanol/DCM) gave 1-(5-methyl-1,3,4-thiadiazol-2-yl)-4-(2-hydroxyethyl)piperidine (41 mg, 32%), $^1$H nmr; 1.33 (m, 2H), 1.54 (q, 2H), 1.7 (m, 1H), 1.79 (m, 2H), 2.54 (s, 3H), 3.08 (m, 2H), 3.71 (t, 2H), 3.88 (m, 2).

(b) 1-(5-methyl-2-[1,3,4-thiadiazolyl])-4-piperidineethanol from part (a) was converted into the oxime ether Compound No. 158 by reaction with 4-hydroxybenzaldehyde and ethoxyamine following a similar method to that described in Example 1. The spectral data are recorded below in Table 11.

Example 10

The Compound No's 84, 152–154, 157, 159–160, 196–207, 210 and 212 from Table 6 above were prepared using the appropriate heterocycle and essentially the same method as described in Example 9 for Compound 158. The compounds were purified by column chromatography on silica gel and characterised by their nuclear magnetic resonance (nmr) spectra and Mass Spectral (MS) data which are summarised in Table 11 below.

Example 11

Most of the compounds in Tables 1–8 were prepared from the appropriate heterocyclic alcohol derivative (Het-A-Alk-OH) by reaction with the appropriate hydroxyaromatic carbonyl compound (HO-Ar-C(X$^2$)=O) or hydroxy aromatic oxime ether (HO-Ar-C(X$^2$)=NO-X$^2$) following similar conditions to those described in Examples 1 and 2. An alternative method which was used for some compounds is the reaction of the heterocyclic alkyl halide (Het-A-Alk-Cl) with the appropriate hydroxyaromatic carbonyl compound (HO-Ar-C(X$^2$)=O) or hydroxy aromatic oxime ether (HO-Ar-C(X$^2$)=NO-X$^1$). The compounds were generally purified by column chromatography on silica gel and character-ised by their nuclear magnetic resonance (nmr) spectra and Mass Spectral (MS) data. For convenience the nmr data are recorded in Table 11 below.

TABLE 11

| Compd Number | MS data (ESI) | NMR data: Proton Chemical Shift, δ in ppm (CDCl$_3$ unless otherwise noted) |
|---|---|---|
| 26 | — | 1.20–1.40(m, 5H); 1.65–1.95(m, 5H); 2.95 (bt, 2H); 4.0(s, 3H); 4.05(t, 2H); 4.17(q, 2H); 4.27(bd, 2H); 6.85–6.95(2xd, 3H); 7.10(d, 1H); 7.52(d, 2H); 8.03(s, 1H) |
| 27 | — | 1.31(t, 3H); 2.78(m, 4H); 3.72(m, 4H); 4.22 (m, 6H); 6.91(m, 4H); 7.52(d, 2H); 8.02(s, 1H) |
| 28 | — | 1.31(t, 3H); 1.86(m, 5H); 3.19(m, 2H); 3.92 (m, 2H); 4.20(m, 4H); 6.89(m, 3H); 7.01(d, 1H); 7.50(d, 2H); 8.01(s, 1H) |
| 31 | 397 (M+Na) | 1.32(t, 3H); 1.35–1.51(m, 2H); 1.95–2.17 (m, 3H); 3.01(t, 2H); 3.86(d, 2H); 4.22(q, 2H); 4.38–4.45(m, 2H); 6.91(m, 3H); 7.17(d, 1H); 7.48(d, 2H); 8.02(s, 1H) |
| 32 | 425 (M+Na) | 1.25–1.35(m, 7H); 1.45–1.50(m, 2H); 1.65–1.87 (m, 5H); 3.01(m, 2H); 4.00(bt, 2H); 4.21(q, 2H); 4.37–4.40(m, 2H); 6.89(d, 3H); 7.21(d, 1H); 7.53 (d, 2H); 8.04(s, 1H) |
| 33 | 405.1693 (M+1) | 1.30(m, 2H); 1.75–1.95(m, 5H); 2.97(t, 2H); 3.87 (s, 3H); 3.99(s, 3H); 4.10(t, 2H); 4.35(d, 2H); 6.85(d, 1H), 6.90(d, 1H); 7.00(dd, 1H); 7.15(d, 1H); 7.25(d, 1H); 8.00(s, 1H) |
| 36 | 434 (M+1) | 1.20–1.40(m, 5H); 1.65–1.95(m, 5H); 2.98 (bt, 2H); 4.21(t, 2H); 4.28(q, 2H); 4.33(bd, 2H); 6.87(d, 1H); 7.06(d, 1H); 7.16(d, 1H); 7.73 (dd, 1H); 8.02(s, 1H); 8.05(d, 1H) |
| 37 | 405 (M+1) | 1.20–1.40(m, 5H); 1.65–1.95(m, 5H); 2.95(bt, 2H); 4.05(t, 2H); 4.22(q, 2H); 4.30(bd, 2H); 6.40–6.55(m, 3H); 6.93(dd, 1H); 7.01(d, 1H); 8.02(s, 1H); 10.05(bs, 1H) |
| 40 | 417 (M+1) | 1.20–1.40(m, 2H); 1.65–1.95(m, 5H); 2.95 (bt, 2H); 4.0(t, 2H); 4.25(bd, 2H); 4.65(m, 2H); 5.10(d, 1H); 5.22(d, 1H); 5.35(bs, 1H); 5.98(m, 1H); 6.30(d, 1H); 6.55(m, 2H); 6.79(d, 1H); 7.02(d, 1H); 7.95(s, 1H) |
| 41 | 389 (M+1) | 1.20–1.40(m, 5H); 1.65–1.95(m, 5H); 2.95 (bt, 2H); 4.05(t, 2H); 4.18(q, 2H); 4.38(bd, 2H); 6.90(bd, 2H); 7.05–7.30(m, 4H); 8.02(s, 1H) |
| 42 | 403 (M+1) | 1.20–1.40(m, 5H); 1.65–1.95(m, 5H); 2.15(s, 3H); 2.95(bt, 2H); 3.95(t, 2H); 4.18(q, 2H); 4.32 (bd, 2H); 6.77(d, 1H); 6.86(d, 1H); 7.13(d, 1H); 7.29(d, 1H); 7.41(s, 1H); 8.01(s, 1H) |
| 43 | 415 (M+1) | 1.30(m, 2H); 1.65–1.95(m, 5H); 2.20(s, 3H); 2.95(t, 2H); 4.08(t, 2H); 4.35(d, 2H); 4.65(d, 2H); 5.17(dd, 1H); 5.33(dd, 1H); 6.05(m, 1H); 6.75(d, 1H); 6.87(d, 1H); 7.13(d, 1H); 7.27(d, 1H); 7.41(s, 1H); 8.07(s, 1H) |
| 44 | 389 (M+1) | 1.30(m, 2H); 1.65–1.90(m, 5H); 2.18(s, 3H); 2.95(t, 2H); 3.88(s, 3H); 3.95(t, 2H); 4.29(d, 2H); 6.75(d, 1H); 6.85(d, 1H); 7.08(d, 1H); 7.28(d, 1H); 7.34(s, 1H); 7.90(s 1H) |
| 45 | 417 (M+1) | 1.20–1.40(m, 5H); 1.65–1.95(m, 5H); 2.28(s, 6H); 2.95(bt, 2H); 3.82(t, 2H); 4.18(q, 2H); 4.32(bd, 2H); 6.87(d, 1H); 7.13(d, 1H); 7.24(s, 2H); 7.98(s, 1H) |
| 46 | 369 (M+1) | 1.20–1.40(m, 5H); 1.65–1.95(m, 5H); 2.53(s, 3H); 2.95(bt, 2H); 4.05(t, 2H); 4.21 (q, 2H); 4.35(bd, 2H); 6.82–6.95(m, 2H); 7.05–7.30(m, 4H); 8.01(s, 1H) |
| 48 | 355 (M+1) | 1.30(m, 2H); 1.65–1.95(m, 5H); 2.50(s, 3H); 2.92(t, 2H); 3.98(s, 3H); 4.05(t, 2H); 4.32(d, 2H); 6.86–6.89(m, 2H); 7.05(d, 1H); 7.10(d, 1H); 7.16(d, 1H); 7.28(dd, 1H); 8.02(s, 1H) |
| 49 | 355 (M+1) | 1.20–1.40(m, 5H); 1.65–1.95(m, 5H); 2.91(bt, 2H); 4.05(t, 2H); 4.18(q, 2H); 4.38(bd, 2H); 6.85–6.95(m, 3H); 7.12(dd, 1H); 7.49(d, 2H); 8.01(s, 1H); 8.50(d, 1H) |
| 50 | 419 (M+1) | 1.20–1.40(m, 5H); 1.65–1.95(m, 5H); 2.95 (bt, 2H); 3.78(s, 3H); 3.95(t, 2H); 4.18(q, 2H); 4.32(bd, 2H); 6.42(dd, 1H); 6.48(dd, 1H); 6.88 (d, 1H); 7.15(d, 1H); 7.18(dd, 1H); 8.35(s, 1H) |

TABLE 11-continued

| Compd Number | MS data (ESI) | NMR data: Proton Chemical Shift, δ in ppm (CDCl₃ unless otherwise noted) |
|---|---|---|
| 51 | 383 (M+1) | 1.20–1.40(m, 5H); 1.65–1.95(m, 5H); 2.25 (s, 3H); 2.57(s, 3H); 2.95(bt, 2H); 4.08(t, 2H); 4.23(q, 2H); 4.35(bd, 2H); 6.83 (d, 2H); 6.87(d, 1H); 7.09(d, 1H); 7.33(d, 1H); 7.44(bs, 1H); 8.01(s, 1H) |
| 52 | 369 (M+1) | 1.20–1.45(m, 2H); 1.70–1.90(m, 5H); 2.20 (s, 3H); 2.53(s, 3H); 2.90(t, 2H); 3.90(s, 3H); 4.08(t, 2H); 4.31(d, 2H); 6.75(d, 1H); 6.85 (d, 1H); 7.04(d, 1H); 7.30(dd, 1H); 7.42(d, 1H); 7.95(s, 1H) |
| 54 | 397 (M+1) | 0.97(t, 3H); 1.30(m, 2H); 1.60–1.95(m, 7H); 2.18(s, 3H); 2.55(s, 3H); 2.92(t, 2H); 4.00–4.22 (m, 4H); 4.33(d, 2H); 6.78(d, 1H); 6.87(d, 1H); 7.08(d, 1H); 7.32(dd, 1H); 7.45(d, 1H); 8.02(s, 1H) |
| 55 | — | 1.31(t, 3H); 1.8–2.2(m, 4H); 3.55–3.7 (m, 2H); 3.80–3.98(m, 2H); 4.22(q, 2H); 4.61(m, 1H); 6.85–6.98(dd, 3H); 7.21(d, 1H); 7.50(d, 2H); 8.01(s, 1H) |
| 56 | — | 1.20–1.40(m, 5H); 1.65–1.95(m, 5H); 2.95(bt, 2H); 4.05(t, 2H); 4.18(q, 2H); 4.46(bd, 2H); 6.89(d, 2H); 6.92(d, 1H); 7.4–7.6 (m, 5H); 7.65(d, 1H); 7.96–8.05(m, 3H) |
| 57 | 389 (M+1) | 1.20–1.40(m, 5H); 1.65–1.95(m, 5H); 2.95(bt, 2H); 4.05(t, 2H); 4.22(q, 2H); 4.33(bd, 2H); 6.87 (bd, 1H); 7.16(d, 1H); 7.21(s, 1H); 7.88(d, 2H) |
| 58 | 423 (M+1) | 1.20–1.40(m, 5H); 1.65–1.95(m, 5H); 3.05(bt, 2H); 4.05(t, 2H); 4.20(q, 1.7H, trans); 4.26(q, 0.3H, cis); 4.55(m, 2H); 6.87(d, 2H); 6.93(d, 1H); 7.21(d, 0.3H, cis); 7.44(d, 1H); 7.51(d, 1.70H, trans); 7.87(s, 0.15H, cis); 8.02(s, 0.85H, trans) |
| 59 | — | (d⁶-DMSO)1.20–1.40(m, 2H); 1.65–1.95(m, 5H); 2.49(s, 3H); 2.91(bt, 2H); 4.15(t, 2H); 4.37(bd, 2H); 4.78(q, 2H); 7.08(d, 1H); 7.25(d, 1H); 7.29 (d, 1H); 7.64(d, 1H); 8.41(s, 1H) |
| 61 | 375 (M+1) | Not recorded |
| 67 | 356 (M+1) | Not recorded |
| 68 | 370 (M+1) | Not recorded |
| 70 | 356 (M+1) | Not recorded |
| 71 | 370 (M+1) | Not recorded |
| 73 | 376 (M+1) | Not recorded |
| 75 | 376 (M+1) | Not recorded |
| 76 | 390 (M+1) | Not recorded |
| 77 | 402 (M+1) | |
| 84 | 422 (M+1) | 1.20–1.40(m, 5H); 1.65–1.95(m, 5H); 2.89(bt, 2H); 4.03(t, 2H); 4.17(q, 2H); 4.39(bd, 2H); 6.65 (d, 1H); 6.87(d, 2H); 7.45(d, 2H); 7.58(dd, 1H); 8.02(s, 1H); 8.38(bs, 1H) |
| 85 | 383 (M+1) | 0.97(t, 3H); 1.32–1.34(m, 1H); 1.69–1.88(m, 8H); 2.52(s, 3H); 2.88–2.95(m, 2H); 4.02–4.10 (m, 2H); 4.31–4.34(m, 4H); 6.84–6.88(m, 3H); 7.03(d, 1H); 7.49(d, 2H); 8.02(s, 1H) |
| 86 | 399 (M+1) | 1.25–1.34(m, 1H); 1.74–1.90(m, 6H); 2.65(s, 3H); 3.05(m, 2H); 3.41(s, 3H); 3.69(t, 2H); 4.05 (t, 2H); 4.29(t, 2H); 4.32–4.40(m, 2H); 6.87(m, 3H); 7.10(d, 1H); 7.52(d, 2H); 8.08(s, 1H) |
| 88 | 379 (M+1) | 1.29–1.38(m, 2H); 1.73–1.86(m, 6H); 2.52(s, 3H); 2.88–2.94(m, 2H); 4.06(t, 2H); 4.31–4.34 (m, 2H); 4.74(s, 2H); 6.85–6.91(m, 3H); 7.06(d, 1H); 7.51(d, 2H); 8.06(s, 1H) |
| 89 | 389 (M+1) | Not recorded |
| 91 | 389 (M+1) | Not recorded |
| 92 | 403 (M+1) | Not recorded |
| 94 | 369 (M+1) | Not recorded |
| 95 | 383 (M+1) | Not recorded |
| 97 | 369 (M+1) | Not recorded |
| 98 | 383 (M+1) | Not recorded |
| 106 | 369 (M+1) | Not recorded |
| 108 | 311 (M+Na) | 1.52(t, 3H); 2.16(m, 2H); 2.20(s, 3H); 2.82(t, 2H); 4.01(t, 2H); 4.20(q, 2H); 5.84(s, 1H); 6.85(d, 2H); 7.51(d, 2H); 8.01(s, 1H) |
| 109 | — | 2.16–2.21(m, 4H); 2.22(s, 9H); 2.99(t, 2H); 3.81 (t, 2H); 3.97(s, 3H); 5.87(s, 1H); 7.28(s, 2H) |
| 112 | 331 (M+1) | 0.97(t, 3H); 1.70–1.76(m, 2H); 2.16–2.20 (m, 2H); 2.20–2.27(m, 9H); 2.99(t, 2H); 3.82(t, 2H); 4.10(t, 2H); 5.87(s, 1H); 7.23(s, 2H); 7.97(s, 1H) |
| 118 | 328 (M+1) | 2.17–2.23(m, 2H); 2.27(s, 9H); 2.99(t, 2H); 3.83(t, 2H); 4.77(s, 2H); 5.87(s, 1H); 7.27(s, 2H); 8.03(s, 1H) |
| 119 | 349 (M+Na) | 2.17–2.20(m, 2H); 2.27(s, 9H); 2.48(t, 1H); 2.99(t, 2H); 3.82(t, 2H); 4.75(d, 2H); 5.87(s, 1H); 7.26(s, 2H); 8.02(s, 1H) |
| 120 | 381 (M+Na) | 0.92–1.3(m, 7H); 1.71–1.82(m, 4H); 2.26(s, 9H); 2.72(t, 2H); 3.75(t, 2H); 4.20(q, 2H); 5.81(s, 1H); 7.24(s, 2H); 7.91(s, 1H) |
| 121 | 395 (M+Na) | 1.26–1.33(m, 5H); 1.39–1.43(m, 4H); 1.67–1.81(m, 4H); 2.25(s, 3H); 2.26(s, 6H); 2.70(t, 2H); 3.75(t, 2H); 4.20(q, 2H); 5.79(s, 1H); 7.23 (s, 2H); 7.97(s, 1H) |
| 122 | 367 (M+Na) | 1.31(t, 3H); 1.53–1.60(m, 2H); 1.81(m, 4H); 2.26(s, 9H); 2.75(t, 2H); 3.76(t, 2H); 4.21(q, 2H); 7.23(s, 2H); 7.97(s, 1H) |
| 123 | 353 (M+Na) | 1.29(t, 3H); 1.86–1.95(m, 4H); 2.27(s, 9H); 2.82 (t, 2H); 3.78(t, 2H); 4.19(q, 2H); 5.85(s, 1H); 7.23(s, 2H); 7.98(s, 1H) |
| 124 | 393 (M+Na) | 2.19(m, 2H); 2.27(s, 9H); 2.99(t, 2H); 3.83(t, 2H); 4.49(q, 2H); 5.87(s, 1H); 7.24(s, 2H); 8.03(s, 1H) |
| 125 | 383 (M+Na) | 1.24(t, 3H); 2.17(m, 2H); 2.26–2.27(m, 9H); 2.98(t, 2H); 3.56(q, 2H); 3.71–3.73(m, 2H); 3.80(t, 2H); 4.29(t, 2H); 5.86(s, 1H); 7.19(s, 2H); 8.02(s, 1H) |
| 126 | 367 (M+Na) | 2.16–2.29(m, 14H); 2.99(t, 2H); 3.81(t, 2H); 4.62(s, 2H); 5.87(s, 1H); 7.23(s, 2H); 8.10(s, 1H) |
| 127 | — | 1.31(t, 3H); 2.24–2.28(m, 8H); 3.12(t, 2H); 3.86(t, 2H); 4.20(q, 2H); 6.36(s, 1H); 7.41–7.43 (m, 3H); 7.78–7.81(m, 2H); 7.97(s, 1H) |
| 128 | 383 (M+1) | 1.20–1.40(m, 5H); 1.65–1.95(m, 5H); 3.05(bt, 2H); 4.05(t, 2H); 4.18(q, 2H); 4.35(bd, 2H); 6.88(d, 2H); 6.90(d, 1H); 7.52(d, 2H); 7.72(d, 1H); 8.02(s, 1H); 10.11(s, 1H) |
| 129 | 385 (M+1) | 1.20–1.40(m, 5H); 1.65–1.95(m, 5H); 2.95(bt, 2H); 4.05(t, 2H); 4.18(q, 2H); 4.35(bd, 2H); 4.80(s, 2H); 6.87(d, 1H); 6.95(d, 1H); 7.05(d, 1H); 7.52(d, 2H); 8.02(s, 1H) |
| 130 | 331 (M+1) | 1.25–1.34(m, 6H); 2.21(m, 2H); 2.25(s, 6H); 2.70(q, 2H); 2.99(t, 2H); 3.83(t, 2H); 4.21(q, 2H); 5.89(s, 1H); 7.23(s, 2H); 7.96(s, 1H) |
| 131 | 345 (M+1) | 0.96(t, 3H); 1.31(t, 3H); 1.72(m, 2H); 2.18(m, 2H); 2.27(s, 6H); 2.64(t, 2H); 2.99(t, 2H); 3.81(t, 2H); 4.20(q, 2H); 5.88(s, 1H); 7.23(s, 2H); 7.96(s, 1H) |
| 132 | 317 (M+1) | 1.24–1.33(m, 6H); 2.22(s, 6H); 2.69(q, 2H); 3.22(t, 2H); 4.06(t, 2H); 4.20(q, 2H); 6.04(s, 1H); 7.26(s, 2H); 7.96(s, 1H) |
| 134 | 335 (M+1) | 2.20(m, 2H); 2.27(s, 6H); 2.99(t, 2H); 3.82(t, 2H); 4.31–4.34(m, 1H); 4.41–4.43(m, 1H); 4.59–4.62(m, 1H); 4.75–4.78(m, 1H); 5.87(s, 1H); 7.23(s, 2H); 8.03(s, 1H) |
| 135 | 384 (M+1) | Not recorded |
| 136 | 384 (M+1) | Not recorded |
| 138 | | 1.22–1.33(m, 6H); 1.86–1.97(m, 4H); 2.27(s, 6H); 2.67(q, 2H); 2.81(t, 2H); 3.79(t, 2H); 4.20(q, 2H); 5.78(s, 2H); 7.24(s, 2H); 7.97(s, 1H) |
| 139 | 359 (M+1) | 0.98(t, 3H); 1.32(t, 3H); 1.65(m, 2H); 1.85–1.98(m, 4H); 2.27(s, 6H); 2.62(t, 2H); 2.82(t, 2H); 3.79(t, 2H); 4.22(q, 2H); 5.85(s, 1H); 7.24(s, 2H); 7.98(s, 1H) |
| 145 | 385.2229 (M+1) | 120–1.40(m, 5H); 1.65–1.95(m, 5H); 2.52(s, 3H); 2.90(t, 2H); 4.03(t, 2H); 4.19(q, 2H); 4.32 (d, 2H); 6.40–6.50(m, 2H); 6.85(d, 1H); 7.03 (d, 1H); 7.05(d, 1H); 8.05(m, 1H); 10.12(s, 1H) |
| 146 | 385.2246 (M+1) | 1.20–1.40(m, 5H); 1.70–1.90(m, 5H); 2.53(s, 3H); 2.91(t, 2H); 4.12(t, 2H); 4.20(q, 2H); 4.30(d, 2H); 5.75(brs, 1H); 6.82(d, 1H); 6.86 (d, 1H); 7.02(dd, 1H); 7.06(d, 1H); 7.28(d, 1H); 7.96(s, 1H) |

TABLE 11-continued

| Compd Number | MS data (ESI) | NMR data: Proton Chemical Shift, δ in ppm (CDCl₃ unless otherwise noted) |
|---|---|---|
| 147 | 363 (M+1) | (CD₃OD)1.32(t, 3H); 1.64(m, 2H); 1.75 (m, 2H); 1.88(m, 2H); 3.44(t, 2H); 4.06(t, 2H); 4.20(q, 2H); 6.94(m, 3H); 7.30(d, 1H); 7.54(m, 2H); 8.05(s, 1H) |
| 149 | 404 (M+1) | Not recorded |
| 150 | 403 (M+1) | Not recorded |
| 152 | Not recorded | 1.31(t, 3H); 2.81–2.97(m, 6H); 3.68(m, 4H); 4.21(q, 2H); 4.21–4.26(m, 2H); 6.90(d, 2H); 7.51(d, 2H); 7.86(s, 1H); 8.02(s, 1H); 8.07(s, 1H) |
| 153 | 415 (M+1) | 1.38–1.45(m, 2H); 1.88–1.92(m, 3H); 1.79(t, 2H); 3.17–3.27(m, 2H); 3.93(s, 3H); 3.97–4.05(m, 2H); 4.05(t, 2H); 6.86(d, 2H); 7.51(d, 2H); 7.99(s, 1H). F19 −60.05 ppm |
| 154 | 429 (M+1) | 1.31(t, 3H); 1.4–1.5(m, 2H); 1.78(t, 2H); 1.89–1.93(m, 3H); 3.19–3.27(m, 2H); 3.99–4.05(m, 2H); 4.07(t, 2H); 4.21(q, 2H); 6.87(d, 2H); 7.52(d, 2H); 8.01(s, 1H) |
| 155 | 376 (M+1) | 1.24–1.37(m, 5H); 1.73–1.85(m, 5H); 2.52(s, 3H); 2.89(t, 2H); 4.20(q, 2H); 4.33–4.40(m, 2H); 4.52(t, 2H); 6.87–6.90(m, 2H); 7.05(d, 1H); 7.95(s, 1H) |
| 156 | 362 (M+1) | 1.23–1.37(m, 5H); 1.73–1.85(m, 5H); 2.52(s, 3H); 2.88(t, 2H); 3.95(s, 3H); 4.28–4.33(m, 2H); 4.52(t, 2H); 6.87–6.89(m, 2H); 7.05 (d, 1H); 7.93(s, 1H) |
| 157 | 361 (M+1) | 1.39–1.43(m, 2H); 1.77–2.04(m, 5H); 2.57(s, 3H); 3.12(t, 2H); 3.92–3.95(m, 2H); 3.95 (s, 3H); 4.04(t, 2H); 6.88(d, 2H); 7.50(d, 2H); 8.01(s, 1H) |
| 158 | 375 (M+1) | 1.31(t, 3H); 1.39–1.43(m, 2H); 1.76–2.03 (m, 5H); 2.56(s, 3H); 3.11(t, 2H); 3.91–3.94(m, 2H); 4.04(t, 2H); 4.20(q, 2H); 6.88(d, 2H); 7.52(d, 2H); 8.02(s, 1H) |
| 159 | Not recorded | 1.25–1.33(m, 2H); 1.75–1.88(m, 5H); 2.88–2.94(m, 2H); 3.95(s, 3H); 4.05(t, 2H); 4.23–4.27 (m, 2H); 6.89(d, 2H); 7.49(d, 2H); 7.86(s, 1H); 8.01(s, 1H); 8.04(s, 1H) |
| 160 | Not recorded | 1.29–1.36(m, 5H); 1.74–1.88(m, 5H); 2.88–2.95 (m, 2H); 4.05(t, 2H); 4.17–4.24(m, 4H); 6.88(d, 2H); 7.52(d, 2H); 7.86(s, 1H); 8.02(s, 1H); 8.04(s, 1H) |
| 161 | 377 (M+1) | (CD₃OD)1.32(t, 3H); 1.57(m, 2H); 1.74(m, 2H); 1.87(m, 2H); 3.15(s, 3H); 3.65(t, 2H); 4.05(t, 2H); 4.18(q, 2H); 6.94(m, 2H); 7.15 (d, 1H); 7.38(d, 1H); 7.54(m, 2H); 8.05(s, 1H) |
| 162 | 377 (M+1) | 1.32(t, 3H); 1.51(m, 4H); 1.72(m, 2H); 1.81 (m, 2H); 3.40(m, 2H); 3.98(t, 2H); 4.20(q, 2H); 5.94(bs, 1H); 6.80(bd, 1H); 6.88(m, 2H); 7.22 (m, 1H); 7.50(m, 2H); 8.02(s, 1H) |
| 163 | 349 (M+1) | 1.32(t, 3H); 1.90(m, 4H); 3.50(m, 2H); 4.04(m, 2H); 4.20(q, 2H); 5.93(bs, 1H); 6.80 (m, 1H); 6.88(m, 2H); 7.22(d, 1H); 7.51(m, 2H); 8.02(s, 1H) |
| 167 | 423 (M+1) | Not recorded |
| 168 | 437 (M+1) | Not recorded |
| 171 | 369 (M+1) | Not recorded |
| 172 | 383 (M+1) | Not recorded |
| 177 | 375 (M+1) | Not recorded |
| 180 | 409 (M+1) | Not recorded |
| 182 | 395 (M+1) | Not recorded |
| 183 | 409 (M+1) | Not recorded |
| 185 | 397.2584 (M+1) | 1.25–1.45(m, 5H); 1.70–1.90(m, 5H); 2.35(s, 6H); 2.50(s, 3H); 2.90(t, 2H); 4.02 (t, 2H); 4.19(q, 2H); 4.30(d, 2H); 6.60(s, 2H); 6.85(d, 1H); 7.03(d, 1H); 8.36(s, 1H) |
| 186 | 383.2448 (M+1) | 1.30(m, 2H); 1.70–1.90(m, 5H); 2.40(s, 6H); 2.52(s, 3H); 2.90(t, 2H); 3.94(s, 1H); 4.02(t, 2H); 4.32(d, 2H); 6.60(s, 2H); 6.88(d, 1H); 7.02(d, 1H); 8.32(s, 1H) |
| 187 | 399.4 (M+1) | 1.20–1.40(m, 5H); 1.70–1.95(m, 5H); 2.52 (s, 3H); 2.92(t, 2H); 3.85(s, 3H); 4.03(t, 2H); 4.15(q, 2H); 4.31(d, 2H); 6.42(d, 1H); 6.47(dd, 1H); 6.86(d, 1H); 7.05(d, 1H); 7.71(d, 1H); 8.39(s, 1H) |
| 188 | 383.2435 (M+1) | 1.20–1.45(m, 5H); 1.70–1.90(m, 5H); 2.38(s, 3H); 2.51(s 3H); 2.90(t, 2H); 4.05 (t, 2H); 4.22(q, 2H); 4.32(d, 2H); 6.69(d, 1H); 6.72(dd, 1H); 6.83(d, 1H); 7.06(d, 1H); 7.65(dd, 1H); 8.28(s, 1H) |
| 189 | 369.2272 (M+1) | 1.30(m, 2H); 1.70–1.90(m, 5H); 2.38(s, 3H); 2.51(s, 3H); 2.90(t, 2H); 3.98(s, 3H); 4.05(t, 2H); 4.31(d, 2H); 6.71(d, 1H); 6.72(dd, 1H); 6.82(d, 1H); 7.05(d, 1H); 7.63(dd, 1H); 8.26(s, 1H) |
| 190 | 397.2602 (M+1) | 120–1.45(m, 5H); 1.70–1.90(m, 5H); 2.16(s, 3H); 2.32(s, 3H); 2.52(s, 3H); 2.90(t, 2H); 4.09(t, 2H); 4.21(q, 2H); 4.32(d, 2H); 6.59(s, 1H); 6.85(d, 1H); 7.03(d, 1H); 7.51(s, 1H); 8.23(s, 1H) |
| 191 | 383.2436 (M+1) | 1.32(m, 2H); 1.72–1.90(m, 5H); 2.18(s, 3H); 2.38(s, 3H); 2.54(s, 3H); 2.89(t, 2H); 3.98(s, 3H); 4.05(t, 2H); 4.32(d, 2H); 6.59 (s, 1H); 6.87(d, 1H); 7.05(d, 1H); 7.52(s, 1H); 8.28(s, 1H) |
| 192 | 397.2583 (M+1) | 1.20–1.45(m, 5H); 1.70–1.90(m, 5H); 2.15(s, 3H); 2.30(s, 3H); 2.53(s, 3H); 2.92(t, 2H); 4.06(t, 2H); 4.22(q, 2H); 4.32(d, 2H); 6.78(d, 1H); 6.84(d, 1H); 7.08(d, 1H); 7.52(d, 1H); 8.38(s, 1H) |
| 193 | 383.4 (M+1) | 1.30(m, 2H); 1.72–1.90(m, 5H); 2.15(s, 3H); 2.30 (s, 3H); 2.52(s, 3H); 2.90(t, 2H); 3.95(s, 3H); 4.03(t, 2H); 4.33(d, 2H); 6.71(d, 1H); 6.85 (d, 1H); 7.04(d, 1H); 7.53(d, 1H); 8.35(s, 1H) |
| 194 | 377 (M+1) | 1.42–1.85(m, 8H); 3.14(s, 3H); 3.63 (t, 2H); 3.93(s, 3H); 4.02(m, 3H); 6.94(m, 2H); 7.14(d, 1H); 7.38(d, 1H); 7.54(m, 2H); 8.05(s, 1H) |
| 195 | 363 (M+1) | (CD₃OD)1.32(t, 3H); 1.85(m, 4H); 3.16(s, 3H); 3.70(m, 2H); 4.09(m, 2H); 4.18(q, 2H); 6.95(m, 2H); 7.16(d, 1H); 7.39(d, 1H); 7.54(m, 2H); 8.05(s, 1H) |
| 196 | 368.2343 (M+1) | 1.20–1.40(m, 5H); 1.70–1.90(m, 5H); 2.39(s, 3H); 2.80(t, 2H); 4.05(t, 2H); 4.21(q, 2H); 4.32(d, 2H); 6.45(d, 2H); 6.88(d, 1H); 7.35(d, 1H); 7.51(d, 2H); 8.03(s, 1H) |
| 197 | 418 (M+1) | 1.30–1.34(m, 5H); 1.70–1.95(m, 5H); 3.0–3.15(m, 2H); 3.94(s, 3H); 4.05(m, 4H); 4.33(q, 2H); 6.87(s, 2H); 7.41(s, 1H); 7.50(d, 2H); 8.01(s, 1H) |
| 198 | 432 (M+1) | 1.29–1.39(m, 8H); 1.76–1.88(m, 5H); 3.00–3.09(m, 2H); 4.06–4.07(m, 4H); 4.20 (q, 2H); 4.33(q, 2H); 6.87(d, 2H); 7.41(s, 1H); 7.50(d, 2H); 8.02(s, 1H) |
| 199 | 375 (M+1) | Not recorded |
| 200 | 380 (M+1) | Not recorded |
| 202 | 402 (M+1) | Not recorded |
| 204 | 369 (M+1) | Not recorded |
| 206 | 396 (M+1) | Not recorded |
| 207 | 410 (M+1) | Not recorded |
| 208 | Not recorded | 1.31(t, 3H); 1.2–1.5(m, 2H); 1.7–2.0(m, 5H); 3.05(t, 2H); 3.9–4.1(m, 5H); 4.20(q, 2H); 4.55(bd, 2H); 6.87(d, 2H); 7.03(d, 1H); 7.52(d, 2H); 7.82(d, 1H); 8.02(s, 1H); 8.32(s, 1H) |
| 209 | 364 (M+1) | 1.31(t, 3H); 1.5–1.85(m, 6H); 3.98(t, 2H); 4.19(q, 2H); 6.88(m, 3H); 7.16(d, 1H); 7.50 (d, 2H); 8.02(s, 1H) |
| 210 | Not recorded | 1.2–1.45(m, 5H); 1.7–1.95(m, 5H); 3.02(t, 2H); 4.03(t, 2H); 4.16(q, 2H); 4.55(bd, 2H); 6.89 (d, 2H); 7.45–7.65(m, 4H); 7.80(d, 1H); 8.02 (s, 1H); 8.58(s, 1H) |
| 211 | Not recorded | 1.30(t, 3H); 4.24(q, 2H); 7.30(d, 2H); 7.55–7.75(m, 4H); 8.09(d, 1H); 8.14(s, 1H); 8.58(s, 1H) |
| 212 | Not recorded | 1.25–1.40(m, 5H); 1.70–1.95(m, 5H); 2.30(s, 3H); 2.45(t, 2H); 4.08(t, 2H); 4.20(q, 2H); 4.36 (bd, 2H); 6.80(s, 1H); 6.88(d, 2H); 7.51(d, 2H); 8.06(s, 1H) |

TABLE 11-continued

| Compd Number | MS data (ESI) | NMR data: Proton Chemical Shift, δ in ppm (CDCl₃ unless otherwise noted) |
|---|---|---|
| 213 | Not recorded | 1.25–1.45(m, 5H); 1.75–1.95(m, 5H); 2.65(s, 3H); 2.75–3.05(m, 6H); 4.07(t, 2H); 4.20(q, 2H); 4.36(d, 2H); 6.78(d, 1H); 7.07(d, 1H); 7.17–7.25(m, 2H); 7.29(d, 1H) |

Example 12

Preparation of 4-(2-[1-(6-Formyl-3-pyridazinyl)-4-piperidinyl]ethoxy)benzaldehyde O-ethyloxime (Compound 128)

A solution of 4-{2-[1-(6-Methyl-3-pyridazinyl)-4-piperidinyl]ethoxy}benzaldehyde O-ethyloxime (200 mg, 0.54 mmol, Compound 2) and selenium dioxide (70 mg, 0.63 mmol) in 1,4-dioxane (5 ml) was stirred and heated at 70–80° for 60 hr. The reaction mixture was filtered to remove most of the black selenium powder and then the filtrate was concentrated and applied to a column of silica gel (20g). Elution with chloroform gave the aldehyde product (55 mg, 26%, Compound 128) as the fastest running component (see Table 11 for the nmr and mass spectral data).

Compounds No. 129 and 208 were prepared from Compound No. 128 by standard reactions with sodium borohydride and methoxyamine.

Example 13

Anti-HRV activity in mammalian cell culture assays

Inhibition of viral cytopathic effect (CPE) and measurement of cytotoxicity

The ability of compounds to suppress virus replication and thereby protect cells from HRV-induced CPE was measured using human embryo lung (MRC-5) and human epidermoid carcinoma of the mouth (KB) cells infected with HRV type 1A and HRV type 2, respectively. Cells grown in 96 well tissue culture plates using conventional mammalian tissue culture medium (such as minimum essential medium) supplemented with fetal calf serum were used in an assay essentially similar to that described by Sidwell and Huffman (Applied Microbiology, 22, 797–801(1971)). Test compounds were dissolved in 100% anhydrous dimethyl sulfoxide and serially diluted in tissue culture medium. The antiviral potency of the test compounds was assessed by exposing replicate tissue culture wells to a selected dilution series of between 6 and 7 compound concentrations in the presence of sufficient test virus to invoke significant CPE over the course of the assay. Control cells were also exposed to identical concentrations of compounds in the absence of virus or were infected with virus under the same conditions but in the absence of compounds. Compounds of established anti-HRV efficacy (enviroxime, ribavirin and pirodavir) were assayed by identical procedures in parallel to the test compounds. Tissue culture media were identically supplemented to maintain cell viability and support viral growth while suppressing bacterial growth over the period of the assay (supplements: 2% fetal calf serum, 0.01% sodium bicarbonate, 50 µg/ml gentamicin, 5 µM magnesium chloride, 10 mM of zinc chloride). The assays were incubated at 37° C. in a 5% $CO_2$ atmosphere until significant CPE was observed by microscopic examination of the untreated, HRV infected control cells (generally between 5 and 8 days). At this time all infected cultures were examined by eye using a light microscope and CPE scored on a scale of 0 (no CPE) to 4 (maximum CPE). Uninfected treated cultures were similarly scored for cytotoxic effects (eg. cell enlargement, granularity, rounding, detachment). These scores were used to generate $EC_{50}$ (concentration of compound yielding 50% antiviral efficacy) and $CC_{50}$ (concentration of compound yielding 50% cytotoxicity) values by line regression analysis from plots of compound concentration versus % CPE or % cytotoxicity, respectively. As an alternative to a $CC_{50}$ value, cytotoxicity in some cases was expressed as the Minimum Toxic Concentration (MTC). The MTC corresponds to the lowest compound concentration at which cytotoxic effects were observed.

In some cases the visual scoring system described above was validated by vital dye staining to measure cell viability. The vital dye technique used was a modification of the method described by McManus (Appl. Environment. Microbiol., 31, 35–38,1976). After the assay had been scored by eye with the aid of a microscope, 100 µl of neutral red (NR) solution (0.34% NR in phosphate buffered saline (PBS)) was added to each well and mixed gently. The assays were returned to the 37° C. incubator for 2 hours to facilitate uptake of the NR by viable cells. The medium/NR mixture was then aspirated from the surface of the cells, which were washed twice with PBS. 0.25 ml of absolute ethanol containing Sorensen's citrate buffer I, was added with gentle mixing and the assays incubated at room temperature in the dark for 30 minutes to dissolve the NR. NR staining of viable cells was then quantified spectrophotometrically by measuring the colour density of the NR solution using a BioTek EL-309 microplate reader at dual wavelengths of 540 and 405 min. The differences in the two readings were automatically determined to eliminate background errors. $EC_{50}$ and $CC_{50}$ values were determined by regression analysis matching compound concentration to NR staining.

The results are shown in the Table 12 below. Selectivity indices (SI) are the $CC_{50}$ or MTC divided by the $EC_{50}$.

TABLE 12

| Compound No. | Activity on Rhinovirus Type 2[a] | | | Activity on Rhinovirus Type 1A | | |
|---|---|---|---|---|---|---|
| | $EC_{50}$ (µg/ml) | $CC_{50}$ | SI | $EC_{50}$ (µg/ml) | MTC | SI |
| 1 | <0.001 | >1 | >1000 | 0.0002 | >10.0 | >37317 |
| 1 | | | | 0.003 | >1 | >312 |
| 2 | 0.0002 | 10 | 50,000 | <0.000156 | >50 | >320000 |
| 3 | 0.01 | >1 | >100 | 0.005 | >10.0 | 1841 |
| 4 | 0.5 | >1 | >2 | 0.39 | 10.00 | 25.55 |
| 5 | 0.009 | >1 | >111 | <0.0032 | >1 | >312 |
| 6 | 0.1 | >50 | >500 | 0.06 | >10.00 | >167.09 |

TABLE 12-continued

| Compound | Activity on Rhinovirus Type 2[a] | | | Activity on Rhinovirus Type 1A | | |
|---|---|---|---|---|---|---|
| No. | EC$_{50}$ (μg/ml) | CC$_{50}$ | SI | EC$_{50}$ (μg/ml) | MTC | SI |
| 7 | 0.15 | >1 | >7 | <0.0032 | >1 | >312 |
| 8 | 0.03 | >1 | >33 | <0.0032 | >1 | >312 |
| 9 | 0.08 | >1 | >13 | <0.0032 | >1 | >312 |
| 10 | 0.4 | >1 | >3 | 0.0142 | >1 | >70.54 |
| 11 | 0.004 | >1 | >250 | <0.0032 | >1 | >312 |
| 12 | 0.02 | 1 | 50 | 0.00355 | >1 | >273.7 |
| 13 | 0.006 | 0.5 | 83 | <0.0032 | >1 | >312 |
| 14 | 0.046 | 0.6 | 13 | <0.0032 | >1 | >312 |
| 15 | 0.9 | 0.6 | <1 | >1.0 | >1.0 | NA |
| 16 | <0.001 | 1 | >1000 | <0.0032 | >1 | >312 |
| 17 | >1 | >1 | NA | 0.00612 | >1 | >163.2 |
| 18 | 0.09 | >1 | >11 | 0.0063 | >1 | >158.6 |
| 19 | 0.019 | >1 | >53 | <0.0032 | >1 | >312 |
| 20 | 3 | 2 | 1 | 3.28 | >50.00 | >15.24 |
| 21 | 0.3 | >1 | >3 | >1 | >1 | NA |
| 22 | <0.05 | 20 | >400 | <0.16 | 36.0 | >320 |
| 23 | <0.05 | 17 | >340 | <0.16 | >50 | >320 |
| 24 | <0.05 | 25 | >500 | <0.16 | >50 | >320 |
| 25 | 0.5 | 17 | 34 | 0.36 | >50 | >139.4 |
| 26 | 0.16 | >1 | >6 | 0.077 | >1 | >13.0 |
| 27 | 0.1 | >1 | >10 | 0.017 | >1 | >59.6 |
| 28 | 0.06 | >1 | >17 | 0.180 | >1 | >5.5 |
| 30 | | | | 0.036 | >1 | >28 |
| 31 | 0.003 | >1 | >333 | 0.017 | >1 | >59.6 |
| 32 | 0.014 | >1 | >70 | 0.222 | >1 | >4.5 |
| 33 | 0.04 | >1 | >25 | 0.014 | >1 | >72.4 |
| 34 | 0.7 | >1 | >1 | 0.627 | >1 | >1.59 |
| 36 | 0.03 | >1 | >33 | 0.009 | 0.89 | 99.4 |
| 37 | 0.048 | >1 | >21 | 0.010 | >1 | >96.0 |
| 38 | | | | 0.69 | >1 | >1.45 |
| 40 | 0.4 | >1 | >3 | 0.583 | >1 | >1.72 |
| 41 | <0.001 | >1 | >1000 | 0.016 | >1 | >63.5 |
| 42 | 0.006 | >1 | >167 | 0.006 | >1 | >177.8 |
| 43 | 0.01 | >1 | >100 | 0.006 | >1 | >170 |
| 44 | 0.026 | >1 | >38 | <0.003 | >1 | >312 |
| 45 | 0.03 | >1 | >32 | 0.029 | >1 | >34.0 |
| 46 | NT | | | 0.062 | >1 | >16.0 |
| 47 | NT | | | 0.066 | >1 | >15 |
| 48 | NT | | | 0.016 | >1 | >62 |
| 49 | NT | | | 0.056 | >1 | >17.8 |
| 50 | NT | | | 0.008 | >1 | >121.7 |
| 51 | NT | | | <0.003 | 0.663 | >207.3 |
| 52 | NT | | | <0.003 | >1 | >312 |
| 53 | NT | | | <0.003 | 0.667 | >208 |
| 54 | NT | | | 0.007 | 0.663 | 91 |
| 55 | NT | | | 2.68 | >10 | >3 |
| 56 | NT | | | 2.31 | >10 | >3 |
| 57 | 0.00025 | >0.1 | >400 | 0.001 | >0.1 | >56.3 |
| 58 | NT | | | 0.498 | >1 | >2 |
| 59 | NT | | | 0.162 | 0.56 | 3.4 |
| 60 | NT | | | 0.183 | >1 | >17 |
| 61 | NT | | | 0.058 | >1 | >14 |
| 62 | NT | | | 0.067 | >1 | >14 |
| 63 | NT | | | 0.06 | >1 | >15 |
| 64 | NT | | | 0.05 | >1 | >17 |
| 65 | NT | | | 0.21 | >1 | >4.5 |
| 66 | NT | | | 0.05 | >1 | >18 |
| 67 | NT | | | 0.04 | >1 | >20 |
| 68 | NT | | | 0.04 | >1 | >25 |
| 69 | NT | | | 0.18 | >1 | >5 |
| 70 | NT | | | 0.05 | >1 | >16 |
| 71 | NT | | | 0.05 | >1 | >18 |
| 72 | NT | | | 0.16 | >1 | >6 |
| 73 | NT | | | 0.003 | >1 | >312 |
| 74 | NT | | | 0.02 | >1 | >46 |
| 75 | NT | | | 0.01 | >1 | >98 |
| 76 | NT | | | 0.01 | >1 | >98 |
| 77 | NT | | | 0.003 | >1 | >279 |
| 84 | NT | | | 0.05 | >1 | >19.6 |
| 85 | NT | | | 0.08 | >1 | >12 |
| 87 | NT | | | 0.01 | >1 | >51 |
| 88 | NT | | | 0.005 | >1 | >172 |
| 89 | NT | | | 0.005 | >1 | >174 |
| 91 | NT | | | 0.02 | >1 | >46 |
| 92 | NT | | | 0.20 | >1 | >5 |

TABLE 12-continued

| Compound | Activity on Rhinovirus Type 2[a] | | | Activity on Rhinovirus Type 1A | | |
|---|---|---|---|---|---|---|
| No. | EC$_{50}$ (µg/ml) | CC$_{50}$ | SI | EC$_{50}$ (µg/ml) | MTC | SI |
| 94 | NT | | | 0.024 | >1 | >41 |
| 95 | NT | | | 0.30 | >1 | >3 |
| 98 | NT | | | 0.255 | >1 | >3 |
| 99 | NT | | | 0.205 | >1 | >4 |
| 102 | NT | | | 0.059 | >1 | >17 |
| 103 | NT | | | 0.266 | >1 | >3 |
| 105 | NT | | | 0.126 | >1 | >8 |
| 107 | NT | | | 0.062 | >1 | >16 |
| 108 | 0.6 | >1 | >1 | >1 | >1 | NA |
| 109 | NT | | | 0.053 | >1 | >18.8 |
| 119 | NT | | | 0.046 | >1 | >21.4 |
| 120 | NT | | | 0.04 | >1 | >20 |
| 121 | NT | | | 0.05 | >1 | >16 |
| 122 | NT | | | 0.181 | >1 | >5 |
| 123 | NT | | | 0.060 | >1 | >16 |
| 124 | NT | | | 0.719 | >1 | >1 |
| 125 | NT | | | | | |
| 126 | NT | | | NT | | |
| 127 | NT | | | 0.329 | >1 | >3 |
| 128 | NT | | | 0.063 | >1 | >15 |
| 129 | NT | | | 0.048 | >1 | >20 |
| 136 | NT | | | 0.598 | >1 | >1 |
| 137 | NT | | | 0.054 | >1 | >18 |
| 138 | NT | | | 0.07 | >1 | >15 |
| 139 | NT | | | 0.19 | >1 | >5 |
| 140 | NT | | | 0.016 | >1 | >61 |
| 141 | NT | | | 0.166 | >1 | >6 |
| 142 | NT | | | 0.055 | >1 | >18 |
| 143 | NT | | | 0.020 | >1 | >50 |
| 144 | NT | | | <0.0032 | >1 | >312 |
| 145 | NT | | | <0.0032 | >1 | >312 |
| 146 | NT | | | 0.051 | >1 | >19 |
| 147 | NT | | | 0.194 | >1 | >5 |
| 210 | NT | | | 3.96 | >10 | >2.5 |
| 211 | NT | | | 0.07 | >10 | >151 |
| Comparative compound: | | | | | | |
| Compound No. 110 of U.S. Pat. 4,992,433[a] | 2 | 30 | 15 | 12.06 | >50.00 | >4.14 |
| Controls: | | | | | | |
| Pirodavir | 0.003 | >1 | >300 | 0.02 | >10.00 | 555.74 |
| Ribavirin | NT | | | 1.93 | 98.3 | 51.03 |
| Enviroxime | NT | | | 0.006 | 0.49 | 75.91 |

[a]The comparative compound is the aldehyde intermediate IIa in Example 1 of this invention.

Example 14

Activity against Enteroviruses in Mammalian cell culture assays

Compounds No 1 and 2 of the invention were tested against other picornaviruses using similar cell based assays to those described in Example 5 above and results are shown in Table 13 below.

TABLE 13

| Compound | Activity on Enterovirus 70 | | | Activity on Coxsackie A21 | | |
|---|---|---|---|---|---|---|
| Number | EC$_{50}$(µg/ml) | CC$_{50}$ | SI | EC$_{50}$(µg/ml) | CC$_{50}$ | SI |
| 1 | 0.03 | >50 | >1582 | <0.000156 | >50 | >320000 |
| 2 | 0.00698 | 4.48 | 6409 | <0.000156 | 3.43 | >21927 |

TABLE 13-continued

| Compound | Activity on Enterovirus 70 | | | Activity on Coxsackie A21 | | |
|---|---|---|---|---|---|---|
| Number | $EC_{50}$(µg/ml) | $CC_{50}$ | SI | $EC_{50}$(µg/ml) | $CC_{50}$ | SI |
| Controls: | | | | | | |
| Ribavirin | >100 | >100 | — | >100 | >100 | — |
| Enviroxime | 0.21 | 4.11 | 19.35 | 0.39 | 9.55 | 24.25 |

Example 15

Following a similar method to that described in Example 13 above, the anti-HRV-14 activity in mammalian cell culture assay was determined for the compounds of the invention listed in Table 14 below.

TABLE 14

| Compound | Activity on Rhinovirus Type 14 | | |
|---|---|---|---|
| No. | $EC_{50}$ (µg/ml) | $CC_{50}$ | SI |
| 2 | 0.0018/0.0009 | >0.1 | >55 |
| 5 | 0.0077 | >0.1 | >13 |
| 7 | 0.0068 | >0.1 | >14 |
| 8 | 0.0072 | >0.1 | >13 |
| 11 | 0.0077 | >0.1 | >13 |
| 13 | 0.0078 | >0.1 | >12 |
| 33 | 0.0138 | >0.1 | >7 |
| 42 | 0.0111 | >0.1 | >9 |
| 44 | 0.0194 | >0.1 | >5 |
| 51 | 0.0093 | >0.1 | >10 |
| 52 | 0.0054 | >0.1 | >18 |
| 145 | 0.0072 | >0.1 | >13 |
| 146 | 0.0084 | >0.1 | >11 |
| 154 | 0.0514 | >0.5 | >9 |
| 155 | 0.0138 | >0.5 | >36 |
| 158 | 0.00095 | >0.5 | >526 |
| 160 | 0.0502 | >0.5 | >9 |
| 161 | 0.0348 | >0.5 | >14 |
| 185 | 0.0697 | >1 | >14 |
| 186 | 0.0349 | >1 | >28 |
| 187 | 0.0103 | >1 | >97 |
| 188 | 0.0032 | >1 | >311 |
| 189 | 0.0011 | >1 | >872 |
| 190 | 0.0593 | >1 | >16 |
| 191 | 0.0256 | >1 | >39 |
| 192 | 0.0258 | >1 | >38 |
| 193 | 0.0308 | >1 | >32 |
| 195 | 0.038 | >0.5 | >13 |
| 196 | 0.0424 | >1 | >23 |
| 198 | 0.125 | >0.5 | >4 |
| 199 | 0.0402 | >0.1 | >2.5 |
| 200 | 0.021 | >0.1 | >4.8 |
| 201 | 0.0261 | >0.1 | >3.8 |
| 202 | 0.0593 | >0.1 | >1.7 |
| 203 | 0.060 | >0.1 | >1.7 |
| 204 | 0.0554 | >0.1 | >1.8 |
| 205 | 0.0638 | >0.1 | >1.6 |
| 206 | 0.0233 | >0.1 | >4.3 |
| 209 | 0.0157 | >0.5 | >31 |
| 212 | 0.0107 | >0.5 | >46 |
| Comparative compound: Pleconaril | 0.0608 | >0.1 | >1.6 |

Example 16

The Inhibitory Concentrations of several compounds of the present invention against Human Rhinovirus strains 1B, 3, 4, 5, 6, 8, 9, 11, 12, 13, 16, 17, 21, 25, 30, 32, 33, 38, 39, 40, 42, 43, 45, 48, 52, 54, 56, 57, 59, 60, 63, 67, 68, 69, 72, 73, 85, 86, 89, 91, 92 and 100 were determined by a standard CPE reduction assay similar to that described in Example 13. From these assays it was found that compounds 1 and 2 of the invention showed superior activity to Pirodavir on nearly all HRV strains tested and compound 24 of the invention showed superior activity to Pleconaril.

Example 17

The Inhibitory Concentrations of several compounds of the present invention against the Enterovirus strains Poliovirus 2, Echoviruses 2, 3, 9, 21 and 30 and Coxsackie B3 were determined by a standard CPE reduction assay similar to that described in Example 13. From these assays it was found that compounds 1 and 2 of the invention showed superior activity to Pirodavir on all strains tested.

Example 18

Comparison of Compound 2 of the invention with Pirodavir in a time of addition study using HRV-2

The CPE inhibition assay used in this study was performed as described by Sidwell and Huffman (Appl. Microbiol., 22, 7979, 1971) with slight modifications. For most time of addition experiments virus at a multiplicity of infection (MOI)=0.001 was added to the monolayers (1×10$^5$ cells/well) in each plate and incubated at 37° C. At the appropriate time after virus exposure (0, 1, 2, 4, 6, 8, 24 hr post-virus exposure) Compound 2 or Pirodavir was added to the cells at varying concentrations without removal of the virus and without significantly altering the volume in the wells. The plates were incubated for 5 days at 37° C.

When a pre-treatment was done (−1 hr) compound was added to the wells and incubated for 1 hr at 37° C. Following the 1 hr incubation of the compound, virus was added to each well in a volume that did not significantly alter the concentration of the drug and the plate was incubated for 5 days. For all other treatment times the two compounds were also added within 5 minutes of virus exposure (0 time) and incubated for 5 days.

The assay was stopped at the end of the fifth day when the virus CPE in the virus infected, untreated, control cells was seen in all cells. Both compounds were assayed for virus inhibition in quadruplicate cups in a 96-well microplate; duplicate wells were used for cytotoxicity controls at each compound dosage. For each compound, two wells were set aside as uninfected, untreated cell controls per test and four wells per test received virus only and represented controls for virus replication. Changes due to CPE were graded on a scale of 1–4, grade 4 representing a scenario in which the entire (100%) monolayer in a well showed viral CPE. For all CPE-based assays the 50% effective concentration ($EC_{50}$) was calculated by regression analysis using the means of the CPE ratings at each concentration of compound.

Results: Neither compound was cytotoxic at the doses used in the study (up to 0.1 µg/ml). The $EC_{50}$ values for the two compounds at the various time points are shown in the Table below.

TABLE 19

Effects of the time of addition of Compound 2 and Pirodavir to infected KB cells on the inhibition of HRV-2 replication

| Time of addition of Compound (hr) | $EC_{50}$ (µg/ml) for Compound 2 (visual assay) | $EC_{50}$ (µg/ml) for Pirodavir (visual assay) |
|---|---|---|
| −1 | 0.002 | 0.023 |
| 0 | 0.002 | 0.004 |
| 1 | 0.008 | 0.1 |
| 2 | 0.02 | >0.1 |
| 4 | 0.02 | >0.1 |
| 6 | 0.02 | >0.1 |
| 8 | 0.02 | >0.1 |
| 24 | 0.1 | >0.1 |

The results confirm that Compound 2 is more active than Pirodavir when added at the same time as virus (0 hr). More significantly the results show that Compound 2 has a much stronger effect than Pirodavir when added prior to virus (−1 hr) and that Compound 2 has much more activity than Pirodavir when added several hours after cells have been exposed to virus. The data indicate that Compound 2 may have a different mode of action to Pirodavir and the data is also consistent with Compound 2 being more stable and therefore having a longer lasting activity against HRV.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

What is claimed is:

1. A compound of formula I

Het-A-Alk-W-Ar-C($X^2$)=NO-$X^1$  I, or a salt or pharmaceutically acceptable derivative thereof, where: Het is a radical of the formula:

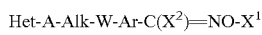
(a-1)

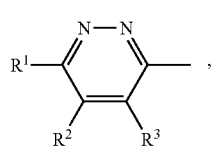
(a-2)

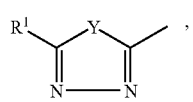

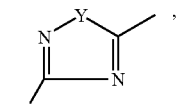
(a-3)

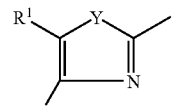
(a-4)

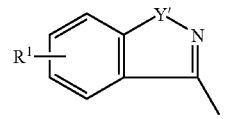
(a-5)

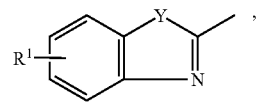
(a-6)

(a-7)

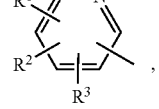
(a-8)

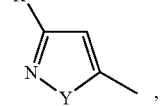
(a-9)

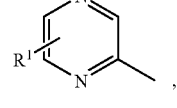
(a-10)

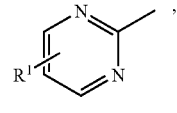
(a-11)

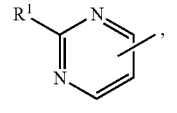
(a-12)

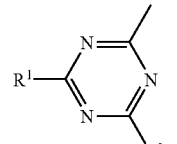
(a-13)

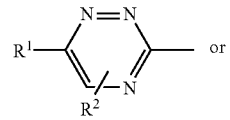
or

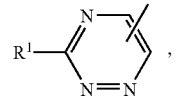
(a-14)

wherein each $R^1$ is independently selected from the group consisting of hydrogen, di($C_{1-6}$alkyl)amino, cyano, formyl, $C_{1-6}$alkoxy, hydroxy$C_{1-4}$alkyl, $C_{1-4}$alkoxy$C_{1-4}$alkyl, $C_{1-6}$haloalkoxy, aryloxy, $C_{1-6}$-alkylthio, arylthio, $C_{1-6}$alkylsulphinyl, $C_{1-6}$alkylsulphonyl, arylsulphinyl, arylsulphonyl, —CH=NO-$C_{1-4}$alkyl, $C_{1-6}$alkoxycarbonyl, $C_{1-6}$alkylcarbonyl and aryl;

$R^2$ and $R^3$ are each independently selected from the group consisting of hydrogen, $C_{1-6}$alkyl, $C_{1-6}$alkoxy and halo;

or $R^1$ and $R^2$ or $R^2$ and $R^3$ combined in radicals (a-1), (a-4), (a-7) and (a-13) may represent a bivalent radical of formula —CH=CH—CH=CH— or $(CH_2)_p$ where p is an integer from 2 to 4;

each Y is independently O or S; and each Y' is O, SO or $SO_2$;

A is O, S, NH, N($C_{1-6}$alkyl), $CH_2O$, a direct bond or a bivalent heterocyclic radical of the formula:

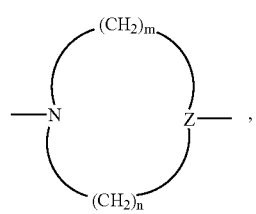

(b-1)

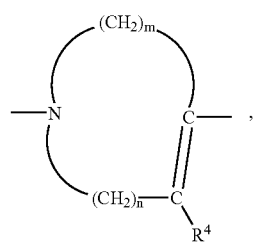

(b-2)

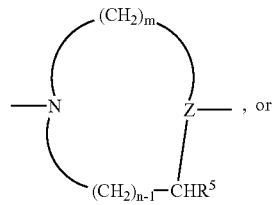

(b-3)

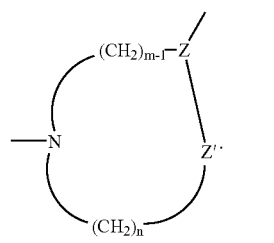

(b-4)

where one or more of the carbon atoms within the radicals (b-1) to (b-4) may be optionally substituted with $C_{1-6}$ alkyl or two carbon atoms in the radicals (b-1) to (b-4) may be bridged with a divalent $C_{2-4}$alkyl radical, m and n are each independently integers of 1 to 4 inclusive with the proviso that the sum of m and n in radicals (b-1) to (b-4) is 3, 4 or 5;

Z is N or $CR^6$ where $R^6$ is hydrogen, hydroxy, $C_{1-6}$ alkyl, $C_{1-6}$ alkoxy or amino;

Z' is O, S, $CHR^7$ or $NR^8$ where $R^7$ is hydrogen, hydroxy, $C_{1-6}$ alkyl, $C_{1-6}$ alkoxy or amino and $R^8$ is hydrogen or $C_{1-6}$ alkyl;

$R^4$ is hydrogen or $C_{1-6}$ alkyl; and $R^5$ is hydrogen, hydroxy, $C_{1-6}$ alkyl or $C_{1-6}$ alkoxy;

Alk is divalent $C_{1-7}$alkyl or a direct bond;

W is O, S, $OCH_2$, a direct bond or $NR^9$ where $R^9$ is hydrogen or $C_{1-6}$ alkyl;

Ar is a radical of the formula:

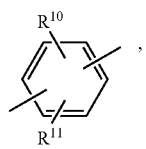

(c-1)

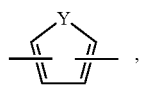

(c-2)

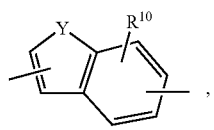

(c-3)

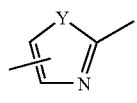

(c-4)

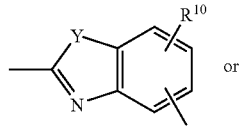

(c-5)

or

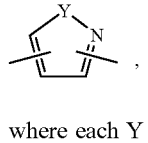

(c-6)

where each Y is independently O or S, and $R^{10}$ and $R^{11}$ are each independently hydrogen, $C_{1-6}$alkyl, hydroxy, $C_{1-6}$alkyl, halo, amino, cyano, nitro, $C_{1-6}$alkoxy, hydroxy $C_{1-6}$alkylthio, or trifluoromethyl;

$X^1$ is $C_{1-6}$ alkyl, $C_{3-6}$ alkenyl, $C_{3-6}$ haloalkenyl, $C_{3-6}$ alkynyl, $C_{3-6}$ haloalkynyl or $C_{1-6}$ alkyl substituted by halo, cyano, nitro, hydroxy, aryl, $C_{1-4}$alkoxy, $C_{2-6}$ alkoxyalkoxy, acyl or $C_{1-4}$alkylthio; and $X^2$ is hydrogen, cyano, F, Cl, $C_{1-4}$ alkyl, $C_{1-4}$ haloalkyl or a bivalent radical of formula —$(CH_2)_2$—, —$(CH_2)_3$—, —$CH_2)_2O$— or —$(CH_2)_2O$— which forms a 5- or 6-membered ring with a neighbouring carbon atom of Ar;

with the proviso that when Alk is a direct bond and A is O, S, $CH_2O$ or a direct bond, then W is not O, S, $OCH_2$ or a direct bond.

2. A compound according to claim 1 wherein Het is a radical of formula (a-1), (a-2) or (a-8).

3. A compound according claim 1 wherein $R^1$ is selected from hydrogen, methyl, ethyl, chloro, methoxy and trifluoromethyl.

4. A compound according to claim 1 wherein $R^2$ and $R^3$ are independently hydrogen, chloro or methyl.

5. A compound according to claim 1 wherein Y is O or S.

6. A compound according to claim 1 wherein A is O, NH, NMe, a bond or a radical of formula (b-1).

7. A compound according to claim 1 wherein Z is CH or N.

8. A compound according to claim 1 wherein Alk is divalent $C_{1-6}$alkyl or a direct bond.

9. A compound according to claim 1 wherein W is O.

10. A compound according to claim 1 wherein Ar is a radical of formula (c-1), (c-2) or (c-4).

11. A compound according to claim 1 wherein $R^{10}$ and $R^{11}$ are each independently H, methyl chloro, hydroxy, methoxy, cyano or nitro.

12. A compound according to claim 1 wherein Y is O or S.

13. A compound according to claim 1 wherein $X^1$ is $C_{1-4}$alkyl, $C_{2-4}$alkoxyalkyl, $C_{3-4}$alkenyl, $C_{3-4}$alkynyl, $C_{1-4}$haloalkyl, $C_{3-4}$haloalkenyl, $C_{3-4}$haloalkyl or cyanomethyl.

14. A compound according to claim 1 wherein $X^2$ is H, methyl or a bivalent radical of formula $(CH_2)_2$ or $(CH_2)_3$ which forms a 5- or 6-membered ring with the Ar group.

15. A compound of formula II:

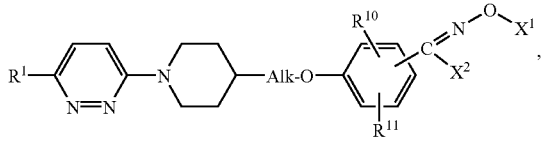

II or a salt or pharmaceutically acceptable derivative thereof, wherein:

$R^1$ is hydrogen, $C_{1-4}$ alkyl, halo, hydroxy, mercapto, trifluoromethyl, amino, mono($C_{1-4}$alkyl)amino, di($C_{1-4}$alkyl)amino, cyano, formyl —CH=NO—$C_{1-4}$alkyl, $C_{1-4}$alkoxy, $C_{1-4}$haloalkoxy, aryloxy, $C_{1-4}$alkylthio, or aryl;

Z is CH or N;

Alk is divalent $C_{1-6}$-alkyl;

$R^{10}$ and $R^{11}$ are cache independently hydrogen, $C_{1-4}$alkyl, $C_{1-4}$alkoxy, halo, hydroxy;

$X^1$ is $C_{1-6}$ alkyl $C_{3-6}$ alkenyl, $C_{3-6}$haloalkenyl, $C_{3-6}$alkynyl, $C_{3-6}$haloalkynyl or $C_{1-6}$alkyl optionally substituted by halo, cyano, nitro, hydroxy, aryl, $C_{1-4}$alkoxy or $C_{1-4}$alkylthio; and $X^2$ is hydrogen, cyano, $C_{1-4}$alkyl, $C_{1-4}$haloalkyl or $X^2$ is —CH$_2$CH$_2$— or —CH$_2$CH$_2$CH$_2$— forming a 5- or 6-membered ring with a carbon atom on the phenyl ring.

16. A compound of formula III:

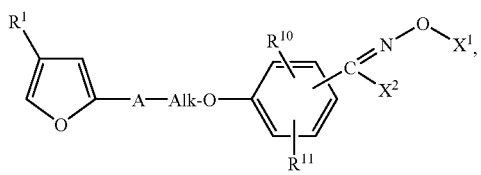

III or a salt or pharmaceutically acceptable derivative thereof, wherein:

$R^1$ is hydrogen, $C_{1-4}$ alkyl halo, hydroxy, mercapto, trifluoromethyl, amino, mono($C_{1-4}$alkyl)amino, di($C_{1-4}$alkyl)amino, cyano, formyl, —CH=NO—$C_{1-4}$alkyl, $C_{1-4}$alkoxy, $C_{1-4}$haloalkoxy, aryloxy, $C_{1-4}$alkylthio, or aryl;

A is a bond or $CH_2O$;

Alk is divalent $C_{1-7}$alkyl;

$R^{10}$ and $R^{11}$ are each independently hydrogen, $C_{1-4}$alkyl, $C_{1-4}$alkoxy, halo, hydroxy;

$X^1$ is $C_{1-6}$alkyl, $C_{3-6}$alkenyl, $C_{3-6}$haloalkenyl, $C_{3-6}$-alkynyl, $C_{3-6}$haloalkynyl or $C_{1-6}$-alkyl optionally substituted by halo, cyano, nitro, hydroxy, aryl, $C_{1-4}$alkoxy or $C_{1-4}$alkylthio; and $X^2$ is hydrogen, cyano, $C_{1-4}$alkyl, $C_{1-4}$haloalkyl or $X^2$ is —CH$_2$CH$_2$— or —CH$_2$CH$_2$CH$_2$— forming a 5- or 6 membered ring with a carbon atom on the phenyl ring.

17. A compound of formula IV

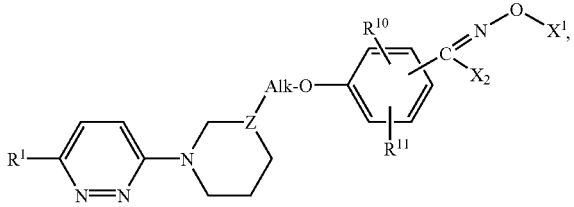

IV or a salt or pharmaceutically acceptable derivative thereof wherein:

$R^1$ is hydrogen, $C_{1-4}$ alkyl, halo, hydroxy, mercapto, trifluoromethyl, amino, mono($C_{1-4}$alkyl)amino, di($C_{1-4}$alkyl)amino, cyano, formyl, —CH=NO—$C_{1-4}$alkyl, $C_{1-4}$alkoxy, $C_{1-4}$haloalkoxy, aryloxy, $C_{1-4}$alkylthio, or aryl;

Z is CH or N;

Alk is divalent $C_{1-6}$alkyl;

$R^{10}$ and $R^{11}$ are each independently hydrogen, $C_{1-4}$alkyl, $C_{1-4}$alkoxy, halo, hydroxy;

$X^1$ is $C_{1-6}$alkenyl, $C_{3-6}$alkenyl, $C_{3-6}$haloalkenyl, $C_{3-6}$alkynyl, $C_{3-6}$haloalkynyl or $C_{1-6}$alkyl optionally substituted by halo, cyano, nitro, hydroxy, aryl, $C_{1-4}$alkoxy or $C_{1-4}$alkylthio; and $X^2$ is hydrogen, cyano, $C_{1-4}$alkyl, $C_{1-4}$haloalkyl or $X^2$ is —CH$_2$CH$_2$— or —CH$_2$CH$_2$CH$_2$— forming a 5- or 6 membered ring with a carbon atom on the phenyl ring.

18. A compound of formula V

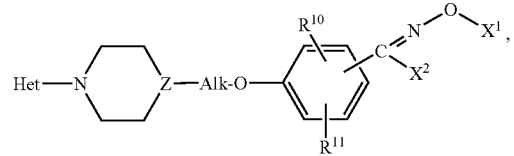

V or a salt or pharmaceutically acceptable derivative thereof, wherein:

Het is pyridyl, pyrazinyl, thiadiazolyl, benzoxazolyl, 1,3,5-triazinyl, pyrimidinyl or quinoxalinyl, each of which may be optionally substituted with 1 to 3 substituents selected from halo, trifluoromethyl, $C_{1-4}$alkyl, $C_{1-4}$alkoxy and hydroxy;

Z is CH or N;

Alk is divalent $C_{1-6}$alkyl;

$R^{10}$ and $R^{11}$ are each independently hydrogen, $C_{1-4}$alkyl, $C_{1-4}$alkoxy, halo, hydroxy;

$X^1$ is $C_{1-6}$alkyl, $C_{3-6}$alkenyl, $C_{3-6}$haloalkenyl, $C_{3-6}$alkynyl, $C_{3-6}$haloalkynyl or $C_{1-6}$alkyl optionally substituted by halo, cyano, nitro, hydroxy, aryl, $C_{1-4}$alkoxy or $C_{1-4}$alkylthio; and $X^2$ is hydrogen, cyano, $C_{1-4}$alkyl, $C_{1-4}$haloalkyl or $X^2$ is —CH$_2$CH$_2$— or —CH$_2$CH$_2$CH$_2$— forming a 5- or 6-membered ring with a carbon atom on the phenyl ring.

19. A compound of formula VI

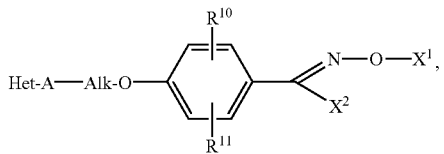

or a salt or pharmaceutically acceptable derivative thereof.
wherein:
Het is pyridyl, pyrazinyl, thiadiazolyl, benzoxazolyl, 1,3,5-triazinyl, pyrimidinyl or quinoxalinyl, each of which may be optionally substituted with 1 to 3 substituents selected from halo, trifluoromethyl, $C_{1-4}$alkyl, $C_{1-4}$alkoxy and hydroxy;
A is a direct bond, O, NH or NMe;
Alk is divalent $C_{1-6}$alkyl;
$R^{10}$ and $R^{11}$ are each independently hydrogen, $C_{1-4}$alkyl, $C_{1-4}$alkoxy, halo, hydroxy,
$X^1$ is $C_{1-6}$alkyl, $C_{3-6}$alkenyl, $C_{3-6}$haloalkenyl $C_{3-6}$alkynyl, $C_{3-6}$-haloalkynyl or $C_{1-6}$alkyl optionally substituted by halo, cyano, nitro, hydroxy, aryl, $C_{1-4}$alkoxy or $C_{1-4}$alkylthio; and
$X^2$ is hydrogen, cyano, $C_{1-4}$alkyl, $C_{1-4}$haloalkyl or $X^2$ is —CH$_2$CH$_2$— or —CH$_2$CH$_2$CH$_2$— forming a 5- or 6-membered ring with a carbon atom on the phenyl ring.

20. A compound of formula VII:

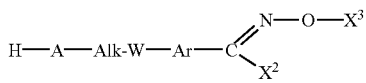

where A, Alk, W, Ar and $X^2$ are as defined in claim 1, and $X^3$ is $X^1$ or an oxime protecting group.

21. A compound of formula X

Het-A-Alk-W-Ar-C(=NOH)X$^2$    X where Het, A, Alk, W, Ar and $X^2$ are as defined in claim 1.

22. A pharmaceutical composition comprising a compound of formula I according to claim 1, or a salt or pharmaceutically acceptable derivative thereof, and a pharmaceutically acceptable carrier.

23. A pharmaceutical composition comprising a compound of formula I according to claim 1, or a salt or pharmaceutically acceptable derivative thereof,
a pharmaceutically acceptable carrier and a known anti-viral or anti-retroviral agent or other pharmaceutical.

24. A method for the treatment of a picornavirus infection in a mammal including the step of administering an effective amount of a compound of formula I according to claim 1, or a salt or pharmaceutically acceptable derivative thereof, 25. A method of claim 24 wherein the picornaviral infection is caused by one or more serotypes of rhinovirus.

26. A method for preparing a pharmaceutical composition comprising admixing a compound of formula I according to claim 1, or a salt or pharmaceutically acceptable derivative thereof:
with one or more pharmaceutically acceptable carriers therefore.

27. A compound selected from the group consisting of the following:

4-{2-[1-(6-Chloro-pyridazin-3-yl)-piperidin-4-yl-ethoxy-benzaldehyde O-ethyl-oxime;
4-{2-[1-(6-Methyl-pyridazin-3-yl)-piperidin-4-yl]-ethoxy}-benzaldehyde O-ethyl-oxime;
1-(4-{2-[1-(6-Chloro-pyridazin-3-yl)piperidin-4-yl]-ethoxy}-phenyl)-ethanone O-ethyl-oxime;
1-(4-{2-[1-(6-Methyl-pyridazin-3-yl)-piperidin-4-yl]-ethoxy}-phenyl)-ethanone O-ethyl-oxime;
4-{2-[1-(6-Chloro-pyridazin-3-yl)-piperidin-4-yl]-ethoxy}-3-methoxy-benzaldehyde O-ethyl-oxime;
1-(4-{2-[1-(6-Chloro-pyridazin-3-yl)-piperidin-4-yl]-ethoxy}-3,5-dimethoxy-phenyl)-ethanone O-ethyl-oxime;
4-{2-[1-(6-Methyl-pyridazin-3-yl)-piperidin-4-yl]-ethoxy}-benzaldehyde O-methyl-oxime;
4-{2-[1-(6-Chloro-pyridazin-3-yl)-piperidin-4-yl]-ethoxy}-benzaldehyde O-methyl-oxime;
1-(4-{2-[1-(6-Methyl-pyridazin-3-yl]-piperidin-4-yl]-ethoxy}-phenyl)-ethanone O-methyl-oxime;
1-(4-{2-[1-(6-Chloro-pyridazin-3-yl)-piperidin-4-yl]-ethoxy}-phenyl)-propan-1-one O-methyl-oxime;
4-{2-[1-(6-Chloro-pyridazin-3-yl)-piperidin-4-yl]-ethoxy}-benzaldehyde O-propyl-oxime;
4-{2-[1-(6-Chloro-pyridazin-3-yl)-piperidin-4-yl]-ethoxy}-benzaldehyde O-isopropyl-oxime;
4-{2-[1-(6-Chloro-pyridazin-3-yl)-piperidin-4-yl]-ethoxy}-benzaldehyde O-allyl-oxime;
[1-(4-{2-[1-(6-Chloro-pyridazin-3-yl)-piperidin-4-yl]-ethoxy}-phenyl)-meth-(E)-ylideneaminooxy]-acetonitrile;
4-{2-[1-(6-Chloro-pyridazin-3-yl)-piperidin-4-yl]-ethoxy}-benzaldehyde O-benzyl-oxime;
4-{2-[1-(6-Chloro-pyridazin-3-yl)-piperidin-4-yl]-ethoxy}-3,5-dimethyl-benzaldehyde O-methyl-oxime;
1-(4-{2-[1-(6-Chloro-pyridazin-3-yl)-piperidin-4-yl]-ethoxy}-3-methoxy-phenyl)-ethanone O-methyl-oxime;
4-{2-[1-(6-Chloro-pyridazin-3-yl)-piperidin-4-yl]-ethoxy}-benzaldehyde O-[2-2-ethoxy-ethoxy)-ethyl]-oxime;
4-(2-{1-[6-(2,2,2-Trifluoro-ethoxy)-pyridazin-3-yl]-piperidin-4-yl}-ethoxy)-benzaldehyde O-ethyl-oxime;
4-(2-[1-(6-Methoxy-pyridazin-3-yl)-piperidin-4-yl]-ethoxy}-benzaldehyde O-ethyl-oxime;
4-[1-(6-Chloro-pyridazin-3-yl)-piperidin-4-ylmethoxy]-benzaldehyde O-benzyl-oxime;
4-[1-(6-Chloro-pyridazin-3-yl)-piperidin-4-ylmethoxy]-benzaldehyde O-allyl-oxime;
4-[1-(6-Chloro-pyridazin-3-yl)-piperidin-4-ylmethoxy]-benzaldehyde O-ethyl-oxime;
4-(3-[1-(6-Chloro-pyridazin-3-yl)-piperidin-4-yl]-propoxy}-benzaldehyde O-ethyl-oxime;
4-{2-[1-(6-Chloro-pyridazin-3-yl)-piperidin-4-yl]-ethoxy)-3-methoxy-benzaldehyde O-methyl-oxime;
1-(4-{2-[1-(6-Chloro-pyridazin-3-yl)-piperidin-4-yl]-ethoxy}-phenyl)-propan-1-one O-ethyl-oxime;
1-(4-{2-[1-Chloro-pyridazin-3-yl)-piperidin-4-yl]-ethoxy}-phenyl)-propan-1-one O-allyl-oxime;
4-{2-[1-(6-Chloro-pyridazin-3-yl)-piperidin-4-yl]-ethoxy}-3-nitro-benzaldehyde O-ethyl-oxime;
4-{2-[1-(6-Chloro-pyridazin-3-yl)-piperidin-4-yl]-ethoxy}-2-hydroxy-benzaldehyde O-ethyl oxime;

4-{2-[1-(6-Chloro-pyridazin-3-yl)-piperidin-4-yl]-ethoxy}-3-methyl-benzaldehyde O-ethyl-oxime;
4-{2-[1-(6-Chloro-pyridazin-3-yl)-piperidin-4-yl]-ethoxy}-3-methyl-benzaldehyde O-allyl-oxime;
4-{2-[1-(6-Chloro-pyridazin-3-yl)-piperidin-4-yl]-ethoxy}-3-methyl-benzaldehyde O-methyl-oxime;
4-{2-[1-(6-Chloro-pyridazin-3-yl)-piperidin-4-yl]-ethoxy}-3-dimethyl-benzaldehyde O-ethyl-oxime;
4-{2-[1-Pyridazin-3-yl-piperidin-4-yl)-ethoxy]-benzaldehyde O-ethyl-oxime;
4-{2-[1-(6-Chloro-pyridazin-3-yl)-piperidin-4-yl]-ethoxy}-2-methoxy-benzaldehyde O-ethyl-oxime;
3-Methyl-4-{2-[1-(6-methyl-pyridazin-3-yl)-piperidin-4-yl]-ethoxy}-benzaldehyde O-ethyl-oxime;
3-Methyl-4-{2-[1-(methyl-pyridazin-3-yl)-piperidin-4-yl-ethoxy}-benzaldehyde O-methyl-oxime;
3-Methyl-4-{2-[1-(6-methyl-pyridazin-3-yl)-piperidin-4-yl]-ethoxy}-benzaldehyde O-allyl-oxime;
3-Methyl-4-{2-[1-(6-methyl-pyridazin-3-yl)-piperidin-4-yl]-ethoxy}-benzaldehyde O-propyl-oxime;
4-[1-(6-Chloro-pyridazin-3-yl)-piperidin-4-yloxy]-benzaldehyde O-ethyl-oxime;
4-{2-[1-(6-Phenyl-pyridazin-3-yl)-piperidin-4-yl]-ethoxy}-benzaldehyde O-ethyl-oxime;
(Z)-4-{2-(1-(6-Chloro-pyridazin-3-yl)-piperidin-4-yl]-ethoxy}-benzaldehyde O-ethyl-oxime;
4-{2-[1-(6-Trifluoromethyl-pyridazin-3-yl)-piperidin-4-yl]-ethoxy}-benzaldehyde O-ethyl-oxime;
4-{2-[1-(6-Methyl-pyridazin-3-yl)-piperidin-4-yl]-ethoxy}-benzaldehyde O-(2,2,2-trifluoro-ethyl)-oxime;
4-{2-[1-(6-Methoxy-pyridazin-3-yl)-piperidin-4-yl]-ethoxy}-benzaldehyde O-allyl-oxime;
4-{2-[1-(6-Methyl-pyridazin-3-yl)-piperidin-4-yl]-ethoxy}-benzaldehyde O-propyl-oxime;
4-{2-[1-(6-Methyl-pyridazin-3-yl)-piperidin-4-yl]-ethoxy}-benzaldehyde O-(2-methoxy-ethyl)-oxime;
4-{2-[1-(6-Methyl-pyridazin-3-yl)-piperidin-4-yl]-ethoxy}-benzaldehyde O-allyl-oxime;
4-{2-[1-(6-Methyl-pyridazin-3-yl)-piperidin-4-yl]-ethoxy}-benzaldehyde O-prop-2-ynyl-oxime;
4-{3-[1-(6-Chloro-pyridazin-3-yl)-piperidin-4-yl]-propoxy}-benzaldehyde O-methyl-oxime;
4-{3-[1-(6-Chloro-pyridazin-3-yl)-piperidin-4-yl]-propoxy}-benzaldehyde O-allyl-oxime;
4-{3-[1-(6-Methyl-pyridazin-3-yl)-piperidin-4-yl]-propoxy}-benzaldehyde O-methyl-oxime;
4-{3-[1-(6-Methyl-pyridazin-3-yl)-piperidin-4-yl]-propoxy}-benzaldehyde O-ethyl-oxime;
4-{3-[1-(6-Methyl-pyridazin-3-yl)-piperidin-4-yl]-propoxy}-benzaldehyde O-allyl-oxime;
4-{3-[1-(6-Trifluoromethyl-pyridazin-3-yl)-piperidin-4-yl]-propoxy}-benzaldehyde O-methyl-oxime;
4-[3-(1-Pyridazin-3-yl-piperidin-4-yl)-propoxy]-benzaldehyde O-methyl-oxime;
4-[3-(1-Pyridazin-3-yl-piperidin-4-yl)-propoxy]-benzaldehyde O-ethyl-oxime;
4-[3-(1-Pyridazin-3-yl-piperidin-4-yl)-propoxy]-benzaldehyde O-allyl-oxime;
6-(4-{2-[4-(Ethoxyimino-methyl)-phenoxy]-ethyl}-piperidin-1-yl)-pyridazine-3carbaldehyde;
4-{2-[1-(6-Hydroxymethyl-pyridazin-3-yl)-piperidin-4-yl]-ethoxy}-benzaldehyde O-ethyl-oxime;
4-{2-[1-(6-Methyl-pyridazin-3-yl)-piperidin-4-yl]-ethoxy}-benzaldehyde O-(2-fluoro-ethyl)-oxime;
4-{2-[1-(6-Methyl-2-oxy-pyridazin-3-yl)-piperidin-4-yl]-ethoxy}-benzaldehyde O-ethyl-oxime;
4-{2-[1-(6-Methyl-pyridazin-3-yl)-piperidin-4-yl]-ethoxy}-benzaldehyde O-ethyl-oxime;
3-Hydroxy-4-{2-[1-(6-methyl-pyridazin-3-yl)-piperidin-4-yl]-ethoxy}-benzaldehyde O-ethyl-oxime;
2,6-Dimethyl-4-{2-[1-(6-methyl-pyridazin-3-yl)-piperidin-4-yl]-ethoxy}-benzaldehyde O-ethyl-oxime;
2,6-Dimethyl-4-{2-[1-(6-methyl-pyridazin-3-yl)-piperidin-4-yl]-ethoxy}-benzaldehyde O-methyl-oxime;
2-Methoxy-4-(2-[1-(6-methyl-pyridazin-3-yl)-piperidin-4-yl]-ethoxy}-benzaldehyde O-ethyl-oxime;
2-Methyl-4-{2-[1-(6-methyl-pyridazin-3-yl)-piperidin-4-yl]-ethoxy}-benzaldehyde O-ethyl-oxime;
2-Methyl-4-{2-[1-(6-methyl-pyridazin-3-yl)-piperidin-4-yl]-ethoxy}-benzaldehyde O-methyl-oxime;
2,5-Dimethyl-4-(2-[1-(6-methyl-pyridazin-3-yl)-piperidin-4-yl]-ethoxy}-benzaldehyde O-ethyl-oxime;
2,5-Dimethyl-4-{2-[1-(6-methyl-pyridazin-3-yl)-piperidin-4-yl]-ethoxy}-benzaldehyde O-methyl-oxime;
2,3-Dimethyl-4-{2-[1-(6-methyl-pyridazin-3-yl)-piperidin-4-yl]-ethoxy}-benzaldehyde O-ethyl-oxime;
2,3-Dimethyl-4-{2-[1-(6-methyl-pyridazin-3-yl)-piperidin-4-yl]-ethoxy}-benzaldehyde O-methyl-oxime, and
6-(4-{2-[4-(Ethoxyimino-methyl)-phenoxy]-ethyl}-piperidin-1-yl)-pyridazine-3-carbaldehyde O-methyl-oxime.

28. A compound selected from the group consisting of the following:
3-{2-[1-(6-Chloro-pyridazin-3-yl)-piperidin-4-yl]-ethoxy}-benzaldehyde O-methyl-oxime;
3-{2-[1-(6-Chloro-pyridazin-3-yl)-piperidin-4-yl]-ethoxy}-4-methoxy-benzaldehyde O-methyl-oxime;
3-{2-[1-(6-Chloro-pyridazin-3-yl)-piperidin-4-yl]-ethoxy}-5-hydroxy-benzaldehyde O-methyl-oxime;
3-{2-[1-(6-Chloro-pyridazin-3-yl)-piperidin-4-yl]-ethoxy}-5-hydroxy-benzaldehyde O-ethyl-oxime;
3-{2-[1-(6-Chloro-pyridazin-3-yl)-piperidin-4-yl]-ethoxy}-5-hydroxy-benzaldehyde O-allyl-oxime;
3-{2-[1-(6-Chloro-pyridazin-3-yl)-piperidin-4-yl]-ethoxy}-benzaldehyde O-ethyl-oxime;
3-{2-[1-(6-Methyl-pyridazin-3-yl)-piperidin-4-yl]-ethoxy}-benzaldehyde O-ethyl-oxime;
3-{2-[1-(6-Methyl-pyridazin-3-yl)-piperidin-4-yl]-ethoxy}-benzaldehyde O-allyl-oxime;
3-{2-[1-(6-Methyl-pyridazin-3-yl)-piperidin-4-yl]-ethoxy}-benzaldehyde O-methyl-oxime;
3-[1-(6-Chloro-pyridazin-3-yl)-piperidin-4-ylmethoxy]-benzaldehyde O-methyl-oxime;
3-[1-(6-Chloro-pyridazin-3-yl)-piperidin-4-ylmethoxy]-benzaldehyde O-ethyl-oxime;
3-[1-(Chloro-pyridazin-3-yl)-piperidin-4-ylmethoxy]-benzaldehyde O-allyl-oxime;
3-{3-[1-(6-Chloro-pyridazin-3-yl)-piperidin-4-yl]-propoxy}-benzaldehyde O-methyl-oxime;
3-{3-[1-(6-Chloro-pyridazin-3-yl)-piperidin-4-yl]-propoxy}-benzaldehyde O-ethyl-oxime;

3-{3-[1-(6-Chloro-pyridazin-3-yl)-piperidin-4-yl]-propoxy}-benzaldehyde O-allyl-oxime;
3-{3-[1-(6-Methyl-pyridazin-3-yl)-piperidin-4-yl]-propoxy}-benzaldehyde O-methyl-oxime;
3-{3-[1-(6-Methyl-pyridazin-3-yl)-piperidin-4-yl]-propoxy}-benzaldehyde O-ethyl-oxime;
3-{3-[1-(6-Methyl-pyridazin-3-yl)-piperidin-4-yl]-propoxy}-benzaldehyde O-allyl-oxime;
3-{3-[1-(6-Trifluoromethyl-pyridazin-3-yl)-piperidin-4-yl]-propoxy}-benzaldehyde O-methyl-oxime;
3-[3-(1-Pyridazin-3-yl-piperidin-4-yl)-propoxy]-benzaldehyde O-methyl-oxime;
3-[3-(1-Pyridazin-3-yl-piperidin-4-yl)-propoxy]-benzaldehyde O-ethyl-oxime;
3-[3-(1-Pyridazin-3-yl-piperidin-4-yl)-propoxy]-benzaldehyde O-allyl-oxime; and
4-{2-[1-(6-Methyl-pyridazin-3-yl)-piperidin-4yl]-ethoxy}-indan-1-one O-ethyl-oxime.

29. A compound selected from the group consisting of the following:
3,5-Dimethyl-4-[3-(3-methyl-isoxazol-5-yl)-propoxy]-benzaldehyde O-methyl-oxime;
3,5-Dimethyl-4-[3-(3-methyl-isoxazol-5-yl)-propoxy]-benzaldehyde O-allyl-oxime;
3,5-Dimethyl-4-[3-(3-methyl-isoxazol-5-yl)-propoxy]-benzaldehyde O-ethyl-oxime;
3,5-Dimethyl-4-[3-(3-methyl-isoxazol-5-yl)-propoxy]-benzaldehyde O-benzyl-oxime;
4-[3-(3-Methyl-isoxazol-5-yl)-propoxy]-benzaldehyde O-ethyl-oxime;
1-{3,5-Dimethyl-4-[3-(3-methyl-isoxazol-5-yl)-propoxy]-phenyl}-ethanone O-methyl-oxime;
1-{3,5-Dimethyl-4-[3-(3-methyl-isoxazol-5-yl)-propoxy]-phenyl}-ethanone O-allyl-oxime;
1-{3,5-Dimethyl-4-[3-(3-methyl-isoxazol-5-yl)-propoxy]-phenyl}-ethanone O-allyl-oxime;
3,5-Dimethyl-4-[3-(3-methyl-isoxazol-5-yl)-propoxy]-benzaldehyde O-propyl-oxime;
1-{3,5-Dimethyl-4-[3-(3-methyl-isoxazol-5-yl)-propoxy]-phenyl}-propan-1-one O-methyl-oxime;
1-{3,5-Dimethyl-4-[3-(3-methyl-isoxazol-5-yl)-propoxy]-phenyl}-propan-1-one O-ethyl-oxime;
1-{3,5-Dimethyl-4-[3-(3-methyl-isoxazol-5-yl)-propoxy]-phenyl}-propan-1-one O-allyl-oxime;
1-{3,5-Dimethyl-4-[3-(3-methyl-isoxazol-5-yl)-propoxy]-phenyl}-ethanone O-ethyl-oxime;
3,5-Dimethyl-4-[3-(3-methyl-isoxazol-5-yl)-propoxy]-benzaldehyde O-isopropyl-oxime;
[1-{3,5-Dimethyl-4-[3-(3-methyl-isoxazol-5-yl)-propoxy]-phenyl}-meth-(E)-ylideneaminooxy]-acetonitrile;
3,5-Dimethyl-4-[3-(3-methyl-isoxazol-5-yl)-propoxy]-benzaldehyde O-prop-2-ynyl-oxime;
3,5-Dimethyl-4-[6-(3-methyl-isoxazol-5-yl)-hexyloxy]-benzaldehyde O-ethyl-oxime;
3,5-Dimethyl-4-[7-(3-methyl-isoxazol-5-yl)-heptyloxy]-benzaldehyde O-ethyl-oxime;
3,5-Dimethyl-4-[5-(3-methyl-isoxazol-5-yl)-pentyloxy]-benzaldehyde O-ethyl-oxime;
3,5-Dimethyl-4-[4-(3-methyl-isoxazol-5-yl)-butoxy]-benzaldehyde O-ethyl-oxime;
3,5-Dimethyl-4-[3-(3-methyl-isoxazol-5-yl)-propoxy]-benzaldehyde O-(2,2,2-trifluoro-ethyl)-oxime;
3,5-Dimethyl-4-[3-(3-methyl-isoxazol-5-yl)-propoxy]-benzaldehyde O-(2-ethoxy-ethyl)-oxime;
3,5-Dimethyl-4-[3-(3-methyl-isoxazol-5-yl)-propoxy]-benzaldehyde O-2-oxo-propyl)-oxime;
3,5-Dimethyl-4-[3-(3-phenyl-isoxazol-5-yl)-propoxy]-benzaldehyde O-ethyl-oxime;
4-[3-(3-Ethyl-isoxazol-5-yl)-propoxy]-3,5-dimethyl-benzaldehyde O-ethyl-oxime;
3,5-Dimethyl-4-[3-(3-propyl-isoxazol-5-yl)-propoxy]-benzaldehyde O-ethyl-oxime;
4-[2-(3-Ethyl-isoxazol-5-yl)-ethoxy]-3,5-dimethyl-benzaldehyde O-ethyl-oxime;
3-Methyl-4-[2-(3-propyl-isoxazol-5-yl)-ethoxy]-benzaldehyde O-ethyl-oxime;
3,5-Dimethyl-4-[3-(3-methyl-isoxazol-5-yl)-propoxy]-3,5-dimethyl-benzaldehyde O-(2-fluoro-ethyl)-oxime;
4-[3-(3-Cyclopropyl-isoxazol-5-yl)-propoxy]-3,5-dimethyl-benzaldehyde O-ethyl-oxime;
4-[4-(3-Ethyl-isoxazol-5-yl)-butoxy]-3,5-dimethyl-benzaldehyde O-ethyl-oxime; and
3,5-Dimethyl-4-[4-3-propyl-isoxazol-5-yl)-butoxy]-benzaldehyde O-ethyl-oxime.

30. A compound selected from the group consisting of the following:
4-{2-[4-(6-Chloro-pyridazin-3-yl)-piperazin-1-yl]-ethoxy}-benzaldehyde O-ethyl-oxime;
4-[2-(4-Pyridazin-3-yl-piperazin-1-yl)-ethoxy]-benzaldehyde O-ethyl-oxime;
3-[2-(4-Pyridazin-3-yl-piperazin-1-yl)-ethoxy]-benzaldehyde O-ethyl-oxime;
4-[2-(4-Pyridazin-3-yl-piperazin-1-yl)-ethoxy]-benzaldehyde O-allyl-oxime;
4-{2-[4-(6-Methyl-pyridazin-3-yl)-piperazin-1-yl]-ethoxy}-benzaldehyde O-methyl-oxime;
4-{2-[4-(6-Methyl-pyridazin-3-yl)-piperazin-1-yl]-ethoxy}-benzaldehyde O-ethyl-oxime;
4-{2-[4-(6-Methyl-pyridazin-3-yl)-piperazin-1-yl]-ethoxy}-benzaldehyde O-allyl-oxime;
3-{2-[4-(6-Methyl-pyridazin-3-yl)-piperazin-1-yl]-ethoxy}-benzaldehyde O-methyl-oxime;
3-{2-[4-(6-Methyl-pyridazin-3-yl)-piperazin-1-yl]-ethoxy}-benzaldehyde O-ethyl-oxime;
3-{2-[4-(6-Methyl-pyridazin-3-yl)-piperazin-1-yl]-ethoxy}-benzaldehyde O-allyl-oxime;
4-{2-[4-(6-Chloro-pyridazin-3-yl)-piperazin-1-yl]-ethoxy}-benzaldehyde O-methyl-oxime;
4-{2-[4-(6-Chloro-pyridazin-3-yl)-piperazin-1-yl]-ethoxy}-benzaldehyde O-allyl-oxime;
3-{2-[4-(6-Chloro-pyridazin-3-yl)-piperazin-1-yl]-ethoxy}-benzaldehyde O-methyl-oxime;
3-{2-[4-(6-Chloro-pyridazin-3-yl)-piperazin-1-yl]-ethoxy}-benzaldehyde O-ethyl-oxime;
3-{2-[4-(6-Chloro-pyridazin-3-yl)-piperazin-1-yl]-ethoxy}-benzaldehyde O-allyl-oxime;
4-{2-[4-(6-Trifluoromethyl-pyridazin-3-yl)-piperazin-1-yl]-ethoxy}-benzaldehyde O-methyl-oxime;
4-{2-[4-(6-Trifluoromethyl-pyridazin-3-yl)-piperazin-1-yl]-ethoxy}-benzaldehyde O-ethyl-oxime;
4-{2-[4-(6-Trifluoromethyl-pyridazin-3-yl)-piperazin-1-yl]-ethoxy}-benzaldehyde O-allyl-oxime;
3-{2-[4-(6-Trifluoromethyl-pyridazin-3-yl)-piperazin-1-yl]-ethoxy}-benzaldehyde O-methyl-oxime;

3-{2-[4-(6-Trifluoromethyl-pyridazin-3-yl)-piperazin-1-yl]-ethoxy}-benzaldehyde O-ethyl-oxime;

3-{2-[4-(6-Trifluoromethyl-pyridazin-3-yl)-piperazin-1-yl]-ethoxy}-benzaldehyde O-allyl-oxime, 4-{2-[4-(6-Methyl-pyridazin-3-yl)-piperazin-1-yl]-ethoxy}-benzaldehyde O-propyl-oxime;

3-{2-[4-(6-Methyl-pyridazin-3-yl)-piperazin-1-yl]-ethoxy}-benzaldehyde O-propyl-oxime;

4-{2-[4-(6-Chloro-pyridazin-3-yl)-piperazin-1-yl]-ethoxy}-benzaldehyde O-propyl-oxime; and 3-{2-[4-(6-Chloro-pyridazin-3-yl)-piperazin-1-yl]-ethoxy}-benzaldehyde O-propyl-oxime.

31. A compound selected from the group consisting of the following;

4-[1-(6-Chloro-pyridazin-3-yl)-piperidin-3-ylmethoxy]-benzaldehyde O-ethyl-oxime;

4-{2-[1-(6-Chloro-pyridazin-3-yl)-piperidin-3-yl]-ethoxy}-benzaldehyde O-methyl-oxime;

4-{2-[1-(6-Chloro-pyridazin-3-yl)-piperidin-3-yl]-ethoxy}-benzaldehyde O-allyl-oxime;

4-{2-[1-(6-Chloro-pyridazin-3-yl)-piperidin-3-yl]-ethoxy}-benzaldehyde O-ethyl-oxime;

4-{3-[1-(6-Chloro-pyridazin-3-yl)-piperidin-3-yl]-propoxy}-benzaldehyde O-ethyl-oxime;

4-{3-[1-(6-Chloro-pyridazin-3-yl)-piperidin-3-yl]-propoxy}-benzaldehyde O-allyl-oxime;

4-{3-[1-(6-Trifluoromethyl-pyridazin-3-yl)-piperidin-3-yl]-propoxy}-benzaldehyde O-methyl-oxime;

4-{3-[1-(6-Trifluoromethyl-pyridazin-3-yl)-piperidin-3-yl]-propoxy}-benzaldehyde O-ethyl-oxime;

4-{3-[1-(6-Trifluoromethyl-pyridazin-3-yl)-piperidin-3-yl]-propoxy}-benzaldehyde O-allyl-oxime;

3-{3-[1-(6-Trifluoromethyl-pyridazin-3-yl)-piperidin-3-yl]-propoxy}-benzaldehyde O-methyl-oxime;

3-{3-[1-(6-Trifluoromethyl-pyridazin-3-yl)-piperidin-3-yl]-propoxy}-benzaldehyde O-ethyl-oxime;

3-{3-[1-(6-Trifluoromethyl-pyridazin-3-yl)-piperidin-3-yl]-propoxy}-benzaldehyde O-allyl-oxime;

4-{3-[1-(6-Methyl-pyridazin-3-yl)-piperidin-3-yl]-propoxy}-benzaldehyde O-allyl-oxime;

3-{3-[1-(6-Methyl-pyridazin-3-yl)-piperidin-3-yl]-propoxy}-benzaldehyde O-methyl-oxime;

3-{3-[1-(6-Methyl-pyridazin-3-yl)-piperidin-3-yl]-propoxy}-benzaldehyde O-ethyl-oxime;

3-{3-[1-(6-Methyl-pyridazin-3-yl)-piperidin-3-yl]-propoxy}-benzaldehyde O-allyl-oxime;

4-[1-(6-Chloro-pyridazin-3-yl)-piperidin-3-ylmethoxy]-benzaldehyde O-methyl-oxime;

4-[1-(6-Chloro-pyridazin-3-yl)-piperidin-3-ylmethoxy]-benzaldehyde O-allyl-oxime;

3-[1-(6-Chloro-pyridazin-3-yl)-piperidin-3-ylmethoxy]-benzaldehyde O-methyl-oxime;

3-[1-(6-Chloro-pyridazin-3-yl)-piperidin-3-ylmethoxy]-benzaldehyde O-ethyl-oxime;

3-[1-(6-Chloro-pyridazin-3-yl)-piperidin-3-ylmethoxy]-benzaldehyde O-allyl-oxime;

4-[1-(6-Trifluoromethyl-pyridazin-3-yl)-piperidin-3-ylmethoxy]-benzaldehyde O-methyl-oxime;

4-[1-(6-Trifluoromethyl-pyridazin-3-yl)-piperidin-3-ylmethoxy]-benzaldehyde O-ethyl-oxime;

4-[1-(6-Trifluoromethyl-pyridazin-3-yl)-piperidin-3-ylmethoxy]-benzaldehyde O-allyl-oxime;

3-[1-(6-Trifluoromethyl-pyridazin-3-yl)-piperidin-3-ylmethoxy]-benzaldehyde O-methyl-oxime;

3-[1-(6-Trifluoromethyl-pyridazin-3-yl)-piperidin-3-ylmethoxy]-benzaldehyde O-ethyl-oxime; and 3-[1-(6-Trifluoromethyl-pyridazin-3-yl)-piperidin-3-ylmethoxy]-benzaldehyde O-allyl-oxime.

32. A compound selected from the group consisting of the following:

4-[2-(5'-Trifluoromethyl-3,4,5,6-tetrahydro-2H-[1,2']bipyridinyl-4-yl)ethoxy]-benzaldehyde O-ethyl-oxime;

4-[2-(5'-Chloro-2,3,5,6-tetrahydro-[1,2']bipyrazinyl-4-yl)-ethoxy]-benzaldehyde O-ethyl-oxime;

4-{2-[1-(5-Trifluoromethyl-[1,3,4]thiadiazol-2-yl)-piperidin-4-yl]-ethoxy}-benzaldehyde O-methyl-oxime;

4-{2-[1-(5-Trifluoromethyl-[1,3,4]thiadiazol-2-yl)-piperidin-4-yl]-ethoxy}-benzaldehyde O-ethyl-oxime;

4-{2-[1-(5-Methyl-[1,3,4]thiadiazol-2-yl)-piperidin-4-yl]-ethoxy}-benzaldehyde O-methyl-oxime;

4-{2-[1-(5-Methyl-[1,3,4]thiadiazol-2-yl)-piperidin-4-yl]-ethoxy}-benzaldehyde O-ethyl-oxime;

4-{2-[1-(5-Chloro-pyrazin-2-yl)-piperidin-4-yl]-ethoxy}-benzaldehyde O-methyl-oxime;

4-{2-[1-(5-Chloro-pyrazin-2-yl)-piperidin-4-yl]-ethoxy}-benzaldehyde O-ethyl-oxime;

4-[2-(6'-Methyl-3,4,5,6-tetrahydro-2H-[1,2']bipyridinyl-4-yl)-ethoxy]-benzaldehyde O-ethyl-oxime;

2-(4-{2-[4-(Methoxyimino-methyl)-phenoxy]-ethyl}-piperidin-1-yl)-thiazole-4-carboxylic acid ethyl ester;

2-(4-{2-[4-(Ethoxyimino-methyl)-phenoxy]-ethyl}-piperidin-1-yl)-thiazole-4-carboxylic acid ethyl ester;

4-{2-[1-(6-Chloro-pyrazin-2-yl)-piperidin-4-yl]-ethoxy}-benzaldehyde O-methyl-oxime;

4-[2-(1-Benzooxazol-2-yl-piperidin-4-yl)-ethoxy]-benzaldehyde O-methyl-oxime;

4-[2-(1-Benzooxazol-2-yl-piperidin-4-yl)-ethoxy]-benzaldehyde O-ethyl-oxime;

4-{2-[1-(4,6-Dimethoxy-[1,3,5]triazin-2-yl)-piperidin-4-yl]-ethoxy}-benzaldehyde O-methyl-oxime;

4-{2-[1-(4,6-Dimethoxy-[1,3,5]triazin-2-yl)-piperidin-4-yl]-ethoxy}-benzaldehyde O-ethyl-oxime;

4-{2-[1-(5-Ethyl-pyrimidin-2-yl)-piperidin-4-yl]-ethoxy}-benzaldehyde O-methyl-oxime;

4-{2-[1-(5-Ethyl-pyrimidin-2-yl)-piperidin-4-yl]-ethoxy}-benzaldehyde O-ethyl-oxime;

4-[2-(1-Benzothiazol-2-yl-piperidin-4-yl)-ethoxy]-benzaldehyde O-methyl-oxime;

4-[2-(1-Benzothiazol-2-yl-piperidin-4-yl)-ethoxy]-benzaldehyde O-ethyl-oxime;

4-{2-[1-(6-Chloro-quinoxalin-2-yl)-piperidin-4-yl]-ethoxy}-benzaldehyde O-ethyl-oxime; and 4-{2-[1-(6-Chloro-5-methyl-pyridazin-3-yl)-piperidin-4-yl]-ethoxy}-benzaldehyde O-ethyl-oxime.

33. A compound selected from the group consisting of the following:

4-[5-(6-Chloro-pyridazin-3-ylamino)-pentyloxy]-benzaldehyde O-ethyl-oxime;

4-{5-[(6-Chloro-pyridazin-3-yl)-methyl-amino]-pentyloxy}-benzaldehyde O-ethyl-oxime;

4-[6-(6-Chloro-pyridazin-3-ylamino)-hexyloxy]-benzaldehyde O-ethyl-oxime;

4-[4-(6-Chloro-pyridazin-3-ylamino)-butoxy]-benzaldehyde O-ethyl-oxime;

4-{6-[(6-Chloro-pyridazin-3-yl)-methyl-amino]-hexyloxy}-benzaldehyde O-methyl-oxime;

4-{4-[(6-Chloro-pyridazin-3-yl)-methyl-amino]-butoxy}-benzaldehyde O-ethyl-oxime;

4-[5-(6-Chloro-pyridazin-3-yloxy)-pentyloxy]-benzaldehyde O-ethyl-oxime; and 4-(6-(Chloro-quinoxalin-2-yloxy)-benzaldehyde O-ethyl-oxime.

34. A compound selected from the group consisting of the following:

2-{2-[1-(6-Methyl-pyridazin-3-yl)-piperidin-4-yl]-ethoxy}-thiazole-4-carbaldehyde O-ethyl-oxime; and 2-{2-[1-(6-Methyl-pyridazin-3-yl)-piperidin-4-yl]-ethoxy}-thiazole-4-carbaldehyde O-methyl-oxime.

* * * * *

UNITED STATES PATENT AND TRADEMARK OFFICE
CERTIFICATE OF CORRECTION

PATENT NO. : 7,078,403 B1
APPLICATION NO. : 10/018963
DATED : July 18, 2006
INVENTOR(S) : Wen-Yang Wu et al.

It is certified that error appears in the above-identified patent and that said Letters Patent is hereby corrected as shown below:

Column 42
Line 67, the phrase "hydrogen, di($C_{1-6}$alkylamino, cyano, formyl" should read as --hydrogen, $C_{1-6}$alkyl, halo, hydroxyl, mercapto, halo$C_{1-4}$alkyl, amino, mono ($C_{1-6}$alkylamino), di($C_{1-6}$alkyl)amino, cyano, formyl--.

Column 43
Line 14, the phrase "is O, SO or $SO_2$" should read as --is O, S, SO or $SO_2$ --.

Column 44
Line 47, the term "-$CH_2$)$_2$-" should read as -- -$(CH_2)_2$- --.

Column 44
Line 48, the term "-$CH_2$)$_2$O-" should read as -- -$CH_2$O- --.

Column 45
Lines 17-25, the formula
"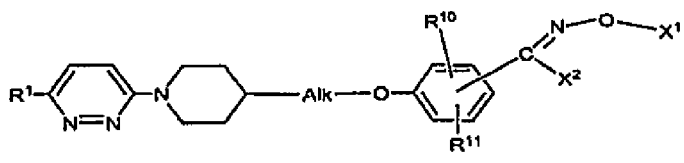" should read as
--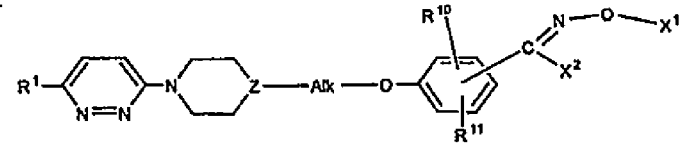--.

Column 45
Line 35, the term "$C_{1-6}$-alkyl" should read as --$C_{1-6}$alkyl--.
Line 36, the term "cashe" should read as --each--.
Lines 47-55, the formula
"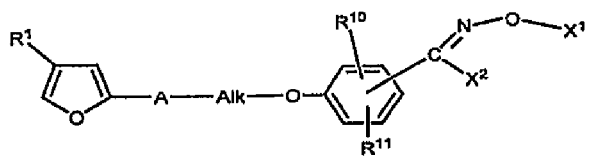" should read as
--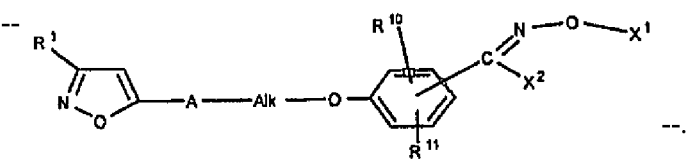--.

UNITED STATES PATENT AND TRADEMARK OFFICE
CERTIFICATE OF CORRECTION

PATENT NO. : 7,078,403 B1
APPLICATION NO. : 10/018963
DATED : July 18, 2006
INVENTOR(S) : Wen-Yang Wu et al.

It is certified that error appears in the above-identified patent and that said Letters Patent is hereby corrected as shown below:

Column 48
Line 62-63, the compound name "1-(4-{2-[1-Chloro-pyridazin-3-yl)-piperidin-4yl]-ethoxy}-phenyl)-propan-1-one O-allyl-oxime" should read as --1-(4-{2-[1-(6-Chloro-pyridazin-3-yl)-piperidin-4y1]-ethoxy}-phenyl)-propan-1-one O-allyl-oxime--.

Column 49
Line 16-17, the compound name "3-Methly-4-{2-1-(methyl-pyridazin-3-yl)-piperidin-4-yl-ethoxy}-benzaldehyde O-methyl oxime" should read as --3-Methly-4-{2-[1-(6-methyl-pyridazin-3-yl)-piperidin-4-yl-ethoxy}-benzaldehyde O-methyl oxime--.

Column 50
Line 62-63, the compound name "3-[1-(Chloro-pyridazin-3-yl)-piperidin-4-ylmethoxy]-benzaldehyde O-allyl-oxime" should read as --3-[1-(6-Chloro-pyridazin-3-yl)-piperidin-4-ylmethoxy]-benzaldehyde O-allyl-oxime--.

Column 51
Line 18-19, the compound name "4-{2-[1-(6-Methyl-pyridazin-3-yl)-piperidin-4yl]-ethoxy}-indan-1-one O-ethyl-oxime" should read as --4-{2-[1-(6-Methyl-pyridazin-3-yl)-piperidin-4-yl]-ethoxy}-indan-1-one O-ethyl-oxime--.

UNITED STATES PATENT AND TRADEMARK OFFICE
CERTIFICATE OF CORRECTION

PATENT NO. : 7,078,403 B1
APPLICATION NO. : 10/018963
DATED : July 18, 2006
INVENTOR(S) : Wen-Yang Wu et al.

It is certified that error appears in the above-identified patent and that said Letters Patent is hereby corrected as shown below:

<u>Column 52</u>
Line 4-5, the compound name "3,5-Dimethyl-4-[3-(3-methyl-isoxazol-5-yl)-propoxy]-benzaldehyde O-2-oxo-propyl)-oxime" should read as --3,5-Dimethyl-4-[3-(3-methyl-isoxazol-5-yl)-propoxy-benzaldehyde O-(2-oxo-propyl)-oxime--.

Lines 16-17, the compound name "3,5-Dimethyl-4-[3-(3-methyl-isoxazol-5-yl)-propoxy]-3,5-dimethyl-benzaldehyde O-(2-fluoro-ethyl)-oxlme" should read as --3,5-Dimethyl-4-[3-(3-methyl-isoxazol-5-yl)- propoxy]-benzaldehyde O-(2-fluoro-ethyl)-oxime--.

Signed and Sealed this

Twentieth Day of November, 2007

JON W. DUDAS
*Director of the United States Patent and Trademark Office*